US012746301B2

(12) United States Patent
Shodder et al.

(10) Patent No.: US 12,746,301 B2
(45) Date of Patent: Sep. 29, 2026

(54) METHODS AND SYSTEMS FOR STERILIZATION

(71) Applicant: Regeneron Pharmaceuticals, Inc., Tarrytown, NY (US)

(72) Inventors: Philip Shodder, East Greenbush, NY (US); Dustin Blodgett, Altamont, NY (US); Dakota Bolt, Tewksbury, MA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 687 days.

(21) Appl. No.: 17/657,254

(22) Filed: Mar. 30, 2022

(65) Prior Publication Data

US 2022/0331470 A1 Oct. 20, 2022

Related U.S. Application Data

(60) Provisional application No. 63/172,457, filed on Apr. 8, 2021.

(51) Int. Cl.

| | |
|---|---|
| ***A61L 2/26*** | (2006.01) |
| ***A61L 2/208*** | (2026.01) |
| *A61L 101/02* | (2006.01) |

(52) U.S. Cl.

CPC ................ *A61L 2/26* (2013.01); *A61L 2/208* (2013.01); *A61L 2101/02* (2020.08); *A61L 2202/122* (2013.01); *A61L 2202/14* (2013.01)

(58) Field of Classification Search

CPC ........ A61L 2/26; A61L 2/208; A61L 2101/02; A61L 2202/122; A61L 2202/14; A61L 2202/11; A61L 2202/23; A61L 2202/24; A61L 2/24

See application file for complete search history.

(56) References Cited

U.S. PATENT DOCUMENTS

| | | |
|---|---|---|
| 4,169,123 A | 9/1979 | Moore et al. |
| 4,512,951 A | 4/1985 | Koubek |
| 5,173,258 A | 12/1992 | Childers |

(Continued)

FOREIGN PATENT DOCUMENTS

| | | |
|---|---|---|
| CN | 101616696 A | 12/2009 |
| CN | 101810870 A | 8/2010 |

(Continued)

OTHER PUBLICATIONS

English Translation of Matsuo et al. (Year: 2020).*

(Continued)

*Primary Examiner* — Sean E Conley
*Assistant Examiner* — Aham Lee
(74) *Attorney, Agent, or Firm* — Bookoff McAndrews, PLLC

(57) ABSTRACT

Embodiments of the present disclosure relate to systems and methods for the application of vaporized chemicals in sterilization procedures, and systems and methods for controlling (e.g., distributing, moving, or exhausting) such chemicals. For example, embodiments of the present disclosure may relate to systems and methods for effecting terminal sterilization of medical products using vaporized hydrogen peroxide (VHP), and/or for the distribution of VHP to, or removal of VHP from, a sterilization system or parts thereof.

23 Claims, 14 Drawing Sheets

(56) References Cited

U.S. PATENT DOCUMENTS 5,364,590 A 11/1994 Hillebrenner
5,439,643 A 8/1995 Liebert
5,472,667 A * 12/1995 Karthaus ................ A61L 2/206 422/31
5,749,203 A 5/1998 McGowan, Jr.
5,779,973 A 7/1998 Edwards et al.
5,792,422 A 8/1998 Lin et al.
5,792,435 A 8/1998 Mueller et al.
5,807,343 A 9/1998 Tucker et al.
5,807,345 A 9/1998 Grabenkort
5,820,603 A 10/1998 Tucker et al.
5,834,313 A 11/1998 Lin
5,904,897 A 5/1999 Kendall et al.
5,911,950 A 6/1999 Chen et al.
5,919,418 A 7/1999 Kendall et al.
5,925,316 A 7/1999 Kendall et al.
5,961,921 A 10/1999 Addy et al.
5,976,113 A 11/1999 Morigi et al.
5,980,825 A 11/1999 Addy et al.
6,030,579 A 2/2000 Addy et al.
6,066,294 A 5/2000 Lin et al.
6,068,817 A 5/2000 Addy et al.
6,077,480 A 6/2000 Edwards et al.
6,096,266 A 8/2000 Duroselle
6,120,730 A 9/2000 Palaniappan et al.
6,126,640 A 10/2000 Tucker et al.
6,132,679 A 10/2000 Conviser
6,132,680 A 10/2000 Addy et al.
6,142,977 A 11/2000 Kolberg et al.
6,164,044 A 12/2000 Porfano et al.
6,174,502 B1 1/2001 Addy et al.
6,187,265 B1 2/2001 Wu et al.
6,189,195 B1 2/2001 Reilly et al.
6,189,292 B1 2/2001 Odell et al.
6,193,931 B1 2/2001 Lin et al.
6,203,756 B1 3/2001 Lin et al.
6,224,828 B1 5/2001 Lin et al.
6,228,324 B1 5/2001 Hasegawa et al.
6,250,052 B1 6/2001 Porfano et al.
6,263,641 B1 7/2001 Odell et al.
6,279,622 B1 8/2001 Nguyen et al.
6,319,480 B1 11/2001 Addy et al.
6,325,972 B1 12/2001 Jacobs et al.
6,390,155 B1 5/2002 Nguyen
6,394,111 B1 5/2002 Jacobs et al.
6,406,666 B1 6/2002 Cicha et al.
6,451,254 B1 9/2002 Wang et al.
6,451,255 B1 9/2002 Williams et al.
6,451,272 B1 9/2002 Fryer et al.
6,454,874 B1 9/2002 Jacobs et al.
6,491,881 B2 12/2002 Fryer et al.
6,494,964 B1 12/2002 Jacobs et al.
6,495,100 B1 12/2002 Lin et al.
6,516,817 B2 2/2003 Jacobs et al.
6,516,818 B2 2/2003 Jacobs et al.
6,528,015 B1 3/2003 Lin et al.
6,528,016 B1 3/2003 Kohler et al.
6,528,017 B2 3/2003 Jacobs et al.
6,530,399 B2 3/2003 Nguyen et al.
6,589,481 B1 7/2003 Lin et al.
6,627,150 B1 9/2003 Wang et al.
6,645,429 B1 11/2003 Raniwala
6,656,426 B1 12/2003 Wang et al.
6,656,427 B2 12/2003 Lin et al.
6,673,313 B2 1/2004 Wang et al.
6,682,696 B1 1/2004 Bjerborn
6,734,405 B2 5/2004 Centanni et al.
6,746,647 B2 6/2004 Kohler et al.
6,746,652 B2 6/2004 Khorzad et al.
6,790,410 B2 9/2004 Metzner et al.
6,792,743 B2 9/2004 Odell et al.
6,807,797 B2 10/2004 Forsberg et al.
6,808,681 B2 10/2004 Bjerborn
6,815,206 B2 11/2004 Lin et al.
6,852,279 B2 2/2005 Williams et al.
6,906,296 B2 6/2005 Centanni et al.
6,967,315 B2 11/2005 Centanni et al.
6,977,061 B2 12/2005 Lin et al.
6,996,952 B2 2/2006 Gupta et al.
7,014,813 B1 3/2006 Watling et al.
7,040,485 B2 5/2006 Gupta et al.
7,048,887 B2 5/2006 Frost et al.
7,108,832 B2 9/2006 Christensen et al.
7,146,746 B2 12/2006 Kawasaki
7,179,419 B2 2/2007 Lin et al.
7,186,373 B2 3/2007 Centanni
7,201,869 B2 4/2007 Williams et al.
7,229,590 B2 6/2007 Awakowicz et al.
7,229,591 B2 6/2007 Wu et al.
7,238,330 B2 7/2007 Hill et al.
7,246,627 B2 7/2007 Jacobs et al.
7,252,800 B2 8/2007 Jacobs et al.
7,267,806 B2 9/2007 Kendall et al.
7,273,594 B2 9/2007 Lin et al.
7,285,254 B2 10/2007 Lin et al.
7,294,305 B2 11/2007 Lin et al.
7,296,678 B2 11/2007 Raynal-Olive et al.
7,300,638 B2 11/2007 Williams et al.
7,303,073 B2 12/2007 Raynal-Olive et al.
7,371,345 B2 5/2008 Stewart et al.
7,431,900 B2 10/2008 Hill et al.
7,452,504 B2 11/2008 Wu et al.
7,459,028 B2 12/2008 Kral et al.
7,459,133 B2 12/2008 Swank
7,468,159 B2 12/2008 Lin et al.
7,481,974 B2 1/2009 Sizer
7,491,371 B2 2/2009 Moller et al.
7,550,122 B2 6/2009 Buczynski
7,556,767 B2 7/2009 Lin et al.
7,569,180 B2 8/2009 Kohler et al.
7,575,716 B2 8/2009 Wu et al.
7,578,969 B2 8/2009 Mielnik et al.
7,582,257 B2 9/2009 Bedard et al.
7,604,773 B2 10/2009 Ekstrom et al.
7,608,218 B2 10/2009 Fryer et al.
7,608,228 B2 10/2009 Horacek et al.
7,625,534 B2 12/2009 Horacek et al.
7,638,090 B2 12/2009 Hyde et al.
7,640,782 B2 1/2010 Hill
7,666,369 B2 2/2010 Bondar
7,670,550 B2 3/2010 Lin et al.
7,713,473 B2 5/2010 Kendall et al.
7,727,464 B2 6/2010 Frost
7,754,156 B2 7/2010 Hyde et al.
7,758,825 B2 7/2010 Kabrick
7,803,315 B2 9/2010 McDonnell et al.
7,803,316 B2 9/2010 Lin et al.
7,807,100 B2 10/2010 Choperena et al.
7,824,610 B2 11/2010 Ko
7,850,906 B2 12/2010 Watling et al.
7,870,959 B2 1/2011 Kuo et al.
7,871,565 B2 1/2011 Jethrow et al.
7,880,887 B2 2/2011 Olson et al.
7,892,486 B2 2/2011 Mizuno et al.
7,910,055 B2 3/2011 Bondar
7,919,059 B2 4/2011 Hill
7,954,521 B2 6/2011 Py et al.
7,981,361 B2 7/2011 Bacik
8,007,717 B2 8/2011 Hill
8,017,074 B2 9/2011 Arnold et al.
8,025,848 B2 9/2011 McVey et al.
8,029,725 B2 10/2011 Olsson et al.
8,034,288 B2 10/2011 Burns et al.
8,039,022 B2 10/2011 Minamikawa et al.
8,062,590 B1 11/2011 Ricciardi et al.
8,071,021 B2 12/2011 Hill
8,083,999 B2 12/2011 Busujima
8,110,156 B2 2/2012 Ricciardi et al.
8,114,342 B2 2/2012 Jung et al.
8,118,788 B2 2/2012 Frezza
8,124,127 B2 2/2012 Faucher et al.
8,129,579 B2 3/2012 McVey et al.
8,132,600 B2 3/2012 Py et al.
8,147,752 B2 4/2012 Iwashita et al.

(56) References Cited

U.S. PATENT DOCUMENTS

| | | | |
|---|---|---|---|
| 8,147,771 | B2 | 4/2012 | Yokoi et al. |
| 8,163,234 | B2 | 4/2012 | Fedegari |
| 8,178,042 | B2 | 5/2012 | Jung et al. |
| 8,196,741 | B2 | 6/2012 | Finke et al. |
| 8,205,416 | B2 | 6/2012 | Hansen |
| 8,221,679 | B2 | 7/2012 | Golkowski |
| 8,230,616 | B2 | 7/2012 | McLaren et al. |
| 8,252,229 | B2 | 8/2012 | Thomas et al. |
| 8,263,016 | B2 | 9/2012 | Kanner |
| 8,263,102 | B2 | 9/2012 | Labrecque et al. |
| 8,268,238 | B2 | 9/2012 | Bondar et al. |
| 8,268,257 | B2 | 9/2012 | Frost |
| 8,277,724 | B2 | 10/2012 | Jung et al. |
| 8,277,728 | B2 | 10/2012 | Lambert et al. |
| 8,293,174 | B2 | 10/2012 | Kaiser et al. |
| 8,312,836 | B2 | 11/2012 | Corbeil et al. |
| 8,323,582 | B2 | 12/2012 | Ko |
| 8,329,098 | B2 | 12/2012 | Kanner |
| 8,329,113 | B2 | 12/2012 | Kanner |
| 8,333,931 | B2 | 12/2012 | Kanner |
| 8,337,772 | B2 | 12/2012 | Laumer et al. |
| 8,343,435 | B2 | 1/2013 | Kanner |
| 8,349,272 | B2 | 1/2013 | Hill |
| 8,357,331 | B2 | 1/2013 | McVey et al. |
| 8,366,995 | B2 | 2/2013 | McLaren et al. |
| 8,367,099 | B2 | 2/2013 | Herweck et al. |
| 8,388,761 | B2 | 3/2013 | Iwashita et al. |
| 8,425,837 | B2 | 4/2013 | Carbone et al. |
| 8,425,852 | B2 | 4/2013 | Matsuuchi et al. |
| 8,428,447 | B2 | 4/2013 | Von Stenglin |
| 8,431,076 | B2 | 4/2013 | Fraundorfer |
| 8,431,077 | B2 | 4/2013 | Goncalves |
| 8,435,459 | B2 | 5/2013 | Reddy et al. |
| 8,435,460 | B2 | 5/2013 | Hirosawa et al. |
| 8,444,919 | B2 | 5/2013 | Erickson |
| 8,486,332 | B1 | 7/2013 | Ricciardi et al. |
| 8,497,004 | B2 | 7/2013 | Davis et al. |
| 8,501,291 | B2 | 8/2013 | Davis et al. |
| 8,506,900 | B1 | 8/2013 | Ricciardi et al. |
| 8,512,633 | B2 | 8/2013 | Cregger et al. |
| 8,529,832 | B2 | 9/2013 | Lee |
| 8,557,365 | B2 | 10/2013 | Maguire, Jr. et al. |
| 8,574,618 | B2 | 11/2013 | Herweck et al. |
| 8,574,627 | B2 | 11/2013 | Martakos et al. |
| 8,580,086 | B2 | 11/2013 | Matsuuchi et al. |
| 8,585,832 | B2 | 11/2013 | Lin et al. |
| 8,591,807 | B2 | 11/2013 | Berentsveig et al. |
| 8,591,808 | B2 | 11/2013 | Berentsveig et al. |
| 8,621,824 | B2 | 1/2014 | Mielnik et al. |
| 8,628,501 | B2 | 1/2014 | Hadden |
| 8,641,982 | B2 | 2/2014 | Burgmeier et al. |
| 8,652,403 | B2 | 2/2014 | Reddy et al. |
| 8,658,089 | B2 | 2/2014 | Berentsveig et al. |
| 8,658,092 | B2 | 2/2014 | Kohler et al. |
| 8,663,555 | B2 | 3/2014 | Shiosawa |
| 8,668,881 | B2 | 3/2014 | Hill et al. |
| 8,685,336 | B2 | 4/2014 | Bondar |
| 8,685,337 | B2 | 4/2014 | Beckmann et al. |
| 8,696,986 | B2 | 4/2014 | Rovison, Jr. et al. |
| 8,703,066 | B2 | 4/2014 | Vaughn et al. |
| 8,715,570 | B2 | 5/2014 | Lindblad et al. |
| 8,721,983 | B2 | 5/2014 | Yokoi et al. |
| 8,721,984 | B2 | 5/2014 | Carbone et al. |
| 8,722,077 | B2 | 5/2014 | Labrecque et al. |
| 8,722,132 | B2 | 5/2014 | Labrecque et al. |
| 8,733,551 | B2 | 5/2014 | Parker et al. |
| 8,741,227 | B2 | 6/2014 | Yokoi et al. |
| 8,747,739 | B2 | 6/2014 | Parker et al. |
| 8,758,679 | B2 | 6/2014 | Hyde et al. |
| 8,758,681 | B2 | 6/2014 | Golkowski |
| 8,765,064 | B2 | 7/2014 | Yokoi et al. |
| 8,771,595 | B2 | 7/2014 | Paskalov |
| 8,790,576 | B2 | 7/2014 | Bauer et al. |
| 8,802,006 | B2 | 8/2014 | Thomas et al. |
| 8,808,622 | B2 | 8/2014 | Arnold et al. |
| 8,808,631 | B2 | 8/2014 | Hill et al. |
| 8,821,807 | B2 | 9/2014 | Schwartz et al. |
| 8,834,790 | B2 | 9/2014 | Boschi et al. |
| 8,834,808 | B2 | 9/2014 | Drenguis |
| 8,840,836 | B2 | 9/2014 | Olson |
| 8,858,611 | B2 | 10/2014 | Ramzipoor et al. |
| 8,858,978 | B2 | 10/2014 | Labrecque et al. |
| 8,865,066 | B2 | 10/2014 | Rovison et al. |
| 8,871,145 | B2 | 10/2014 | Paskalov |
| 8,894,926 | B2 | 11/2014 | Hanada et al. |
| 8,895,239 | B2 | 11/2014 | Franciskovich et al. |
| 8,919,359 | B2 | 12/2014 | Iwashita et al. |
| 8,932,535 | B2 | 1/2015 | Hyde et al. |
| 8,940,245 | B2 | 1/2015 | Reddy et al. |
| 8,945,468 | B2 | 2/2015 | Reddy et al. |
| 8,961,872 | B2 | 2/2015 | Fehr et al. |
| 8,962,023 | B2 | 2/2015 | Labrecque et al. |
| 8,968,651 | B2 | 3/2015 | Hayashi et al. |
| 8,974,730 | B2 | 3/2015 | Burns et al. |
| 8,974,737 | B2 | 3/2015 | Erickson |
| 8,992,837 | B2 | 3/2015 | Jung et al. |
| 8,992,853 | B2 | 3/2015 | Stratman et al. |
| 9,011,767 | B2 | 4/2015 | Wiget |
| 9,022,079 | B2 | 5/2015 | Py et al. |
| 9,028,749 | B2 | 5/2015 | Ryu et al. |
| 9,034,249 | B2 | 5/2015 | Foreman et al. |
| 9,050,385 | B2 | 6/2015 | Weinberger et al. |
| 9,078,435 | B2 | 7/2015 | Dunn |
| 9,078,943 | B2 | 7/2015 | Herold et al. |
| 9,101,679 | B2 | 8/2015 | Robitaille et al. |
| 9,108,835 | B2 | 8/2015 | Hayakawa et al. |
| 9,120,660 | B2 | 9/2015 | Sangi et al. |
| 9,120,661 | B2 | 9/2015 | Sangi et al. |
| 9,125,960 | B2 | 9/2015 | Stratman et al. |
| 9,138,005 | B2 | 9/2015 | Berentsveig et al. |
| 9,156,576 | B2 | 10/2015 | Pjanic et al. |
| 9,173,968 | B2 | 11/2015 | Hanada |
| 9,180,217 | B2 | 11/2015 | Arnold et al. |
| 9,192,164 | B2 | 11/2015 | Berentsveig et al. |
| 9,213,341 | B2 | 12/2015 | Hill |
| 9,220,631 | B2 | 12/2015 | Sigg et al. |
| 9,220,820 | B2 | 12/2015 | Faucher et al. |
| 9,226,495 | B2 | 1/2016 | Berentsveig et al. |
| 9,241,491 | B2 | 1/2016 | Berentsveig et al. |
| 9,242,753 | B2 | 1/2016 | Gay et al. |
| 9,254,343 | B2 | 2/2016 | Herold et al. |
| 9,295,744 | B2 | 3/2016 | Rovison et al. |
| 9,302,021 | B2 | 4/2016 | Klobusnik |
| 9,320,819 | B2 | 4/2016 | Koyama |
| 9,320,820 | B2 | 4/2016 | Rovison, Jr. et al. |
| 9,339,573 | B2 | 5/2016 | Seidenberg et al. |
| 9,339,575 | B2 | 5/2016 | Crawford et al. |
| 9,364,571 | B2 | 6/2016 | Ahiska |
| 9,402,928 | B2 | 8/2016 | Tremblay et al. |
| 9,403,330 | B2 | 8/2016 | Laumer et al. |
| 9,408,931 | B1 | 8/2016 | Ricciardi et al. |
| 9,408,965 | B2 | 8/2016 | Christensen |
| 9,410,191 | B2 | 8/2016 | Alvarez, Jr. et al. |
| 9,427,485 | B2 | 8/2016 | Tremblay et al. |
| 9,439,991 | B2 | 9/2016 | Schwartz et al. |
| 9,452,231 | B2 | 9/2016 | Nonnenmacher |
| 9,457,114 | B2 | 10/2016 | Loy |
| 9,463,259 | B2 | 10/2016 | Hanada |
| 9,474,815 | B2 | 10/2016 | Dufresne et al. |
| 9,480,763 | B2 | 11/2016 | Dufresne et al. |
| 9,480,764 | B2 | 11/2016 | Tremblay et al. |
| 9,480,765 | B2 | 11/2016 | Tremblay et al. |
| 9,498,549 | B2 | 11/2016 | Kanno et al. |
| 9,505,598 | B2 | 11/2016 | Niehr et al. |
| 9,522,202 | B1 | 12/2016 | Ahiska et al. |
| 9,522,205 | B2 | 12/2016 | Ahiska |
| 9,533,065 | B2 | 1/2017 | Foreman et al. |
| 9,539,352 | B2 | 1/2017 | Keener et al. |
| 9,541,487 | B2 | 1/2017 | Saito et al. |
| 9,555,146 | B2 | 1/2017 | Fehr et al. |
| 9,561,297 | B2 | 2/2017 | Kreber |
| 9,566,360 | B2 | 2/2017 | Morikawa et al. |
| 9,566,361 | B2 | 2/2017 | Morikawa et al. |
| 9,592,324 | B2 | 3/2017 | Herweck et al. |

(56) References Cited

U.S. PATENT DOCUMENTS

| | | | |
|---|---|---|---|
| 9,593,004 | B2 | 3/2017 | Hayakawa et al. |
| 9,597,377 | B2 | 3/2017 | Fan |
| 9,603,739 | B2 | 3/2017 | Lerner |
| 9,604,740 | B2 | 3/2017 | Py |
| 9,610,559 | B2 | 4/2017 | Riskin et al. |
| 9,616,148 | B2 | 4/2017 | Klaassen et al. |
| 9,616,368 | B2 | 4/2017 | Turbett et al. |
| 9,617,135 | B2 | 4/2017 | Hayakawa et al. |
| 9,617,136 | B2 | 4/2017 | Hayakawa et al. |
| 9,629,936 | B2 | 4/2017 | Salmisuo |
| 9,637,604 | B2 | 5/2017 | Ito et al. |
| 9,655,987 | B2 | 5/2017 | Hayashi et al. |
| 9,662,412 | B2 | 5/2017 | Ferrell et al. |
| 9,662,450 | B2 | 5/2017 | Jones et al. |
| 9,675,763 | B2 | 6/2017 | Huet |
| 9,682,163 | B2 | 6/2017 | Loy et al. |
| 9,682,175 | B2 | 6/2017 | Labrecque et al. |
| 9,694,095 | B2 | 7/2017 | Paskalov |
| RE46,510 | E | 8/2017 | Odell et al. |
| 9,724,438 | B2 | 8/2017 | Turbett |
| 9,731,041 | B2 | 8/2017 | Akutsu |
| 9,750,832 | B2 | 9/2017 | Paver, Jr. |
| 9,766,012 | B2 | 9/2017 | McLaren et al. |
| 9,775,924 | B2 | 10/2017 | Tanimoto et al. |
| 9,776,161 | B2 | 10/2017 | Igney et al. |
| 9,801,967 | B2 | 10/2017 | Wiget et al. |
| 9,802,726 | B2 | 10/2017 | Mielnik et al. |
| 9,808,548 | B2 | 11/2017 | Toreki et al. |
| 9,814,795 | B2 | 11/2017 | Dufresne et al. |
| 9,814,796 | B2 | 11/2017 | Dunn |
| 9,827,341 | B2 | 11/2017 | Fehr et al. |
| 9,849,203 | B2 | 12/2017 | Rovison, Jr. et al. |
| 9,849,323 | B2 | 12/2017 | Park et al. |
| 9,855,354 | B2 | 1/2018 | Lho et al. |
| 9,861,715 | B2 | 1/2018 | Charlez et al. |
| 9,995,706 | B2 | 6/2018 | Schenk et al. |
| 10,039,850 | B2 | 8/2018 | Taggart et al. |
| 10,058,106 | B2 | 8/2018 | Itarashiki et al. |
| 10,111,975 | B2 | 10/2018 | Laflamme et al. |
| 10,182,969 | B2 | 1/2019 | Arnott et al. |
| 10,214,827 | B2 | 2/2019 | Cabot et al. |
| 10,279,060 | B2 | 5/2019 | Deprey et al. |
| 10,293,068 | B2 | 5/2019 | Ruley et al. |
| 10,293,965 | B2 | 5/2019 | Lu et al. |
| 10,314,929 | B2 | 6/2019 | Nowruzi et al. |
| 10,350,318 | B2 | 7/2019 | Sharma |
| 10,369,241 | B2 | 8/2019 | Min et al. |
| 10,383,966 | B2 | 8/2019 | Dufresne et al. |
| 10,398,796 | B2 | 9/2019 | Shomali et al. |
| 10,576,178 | B2 | 3/2020 | Goncalves |
| 10,617,778 | B2 | 4/2020 | Roberts et al. |
| 10,647,461 | B2 | 5/2020 | Altmann et al. |
| 10,709,313 | B2 | 7/2020 | Stephenson |
| 10,709,803 | B2 | 7/2020 | Laflamme et al. |
| 10,710,759 | B2 | 7/2020 | Lu et al. |
| 10,729,799 | B2 | 8/2020 | Zydowicz et al. |
| 10,792,312 | B2 | 10/2020 | Ferraro et al. |
| 10,793,307 | B2 | 10/2020 | Nohara et al. |
| 10,806,850 | B2 | 10/2020 | Patel et al. |
| 10,823,715 | B2 | 11/2020 | Cregger et al. |
| 10,828,122 | B2 | 11/2020 | Takken et al. |
| 10,828,392 | B2 | 11/2020 | Baer |
| 10,864,291 | B2 | 12/2020 | Fox, III |
| 10,876,144 | B2 | 12/2020 | Centanni et al. |
| 10,889,848 | B2 | 1/2021 | Franciskovich et al. |
| 10,900,062 | B2 | 1/2021 | Franciskovich et al. |
| 10,905,786 | B2 | 2/2021 | Shodder |
| 10,912,623 | B2 | 2/2021 | Takken et al. |
| 10,918,754 | B2 | 2/2021 | Shodder |
| 10,961,350 | B2 | 3/2021 | Momtaz et al. |
| 10,994,914 | B2 | 5/2021 | Erickson |
| 11,000,607 | B2 | 5/2021 | Sharma |
| 11,020,530 | B2 | 6/2021 | Takeuchi et al. |
| 11,077,219 | B2 | 8/2021 | Lim et al. |
| 11,097,029 | B2 | 8/2021 | Dufresne et al. |
| 11,103,644 | B2 | 8/2021 | Bryant et al. |
| 11,110,226 | B2 | 9/2021 | Bryant et al. |
| 11,124,324 | B2 | 9/2021 | Meoni |
| 11,147,925 | B2 | 10/2021 | Bryant et al. |
| 11,160,918 | B2 | 11/2021 | Cook et al. |
| 11,160,951 | B2 | 11/2021 | Mottola et al. |
| 11,179,521 | B2 | 11/2021 | Bryant et al. |
| 11,185,383 | B2 | 11/2021 | Turbett |
| 11,185,635 | B2 | 11/2021 | Bryant et al. |
| 11,191,860 | B2 | 12/2021 | Lim et al. |
| 11,224,555 | B2 | 1/2022 | Chudek et al. |
| 11,253,620 | B2 | 2/2022 | Golkowski et al. |
| 11,253,622 | B2 | 2/2022 | Lim |
| 11,273,230 | B1 | 3/2022 | Baumgartner et al. |
| 11,279,075 | B2 | 3/2022 | Hannafin et al. |
| 11,298,437 | B2 | 4/2022 | Conseil et al. |
| 11,298,463 | B2 | 4/2022 | Tan-Malecki et al. |
| 11,324,845 | B1 | 5/2022 | Ricciardi et al. |
| 11,344,643 | B2 | 5/2022 | Golkowski et al. |
| 11,351,282 | B2 | 6/2022 | Lim et al. |
| 11,357,877 | B2 | 6/2022 | Henniges et al. |
| 11,369,708 | B2 | 6/2022 | Spallek et al. |
| 11,389,556 | B2 | 7/2022 | Henniges et al. |
| 11,534,517 | B2 | 12/2022 | Herrig et al. |
| 11,541,139 | B2 | 1/2023 | Eveland |
| 11,554,886 | B2 | 1/2023 | Procyshyn et al. |
| RE49,474 | E | 3/2023 | Golkowski |
| 11,607,468 | B2 | 3/2023 | Kleinmann et al. |
| 11,638,631 | B2 | 5/2023 | Berner |
| 11,642,487 | B2 | 5/2023 | Heimbuch et al. |
| 11,672,880 | B2 | 6/2023 | Bohnert et al. |
| 11,696,967 | B2 | 7/2023 | Nowruzi et al. |
| 11,707,577 | B2 | 7/2023 | Shetty et al. |
| 11,712,490 | B2 | 8/2023 | Lim et al. |
| 11,712,491 | B2 | 8/2023 | Truong et al. |
| 11,759,537 | B2 | 9/2023 | Matsuo et al. |
| 11,766,494 | B2 | 9/2023 | Takahashi et al. |
| 11,766,497 | B2 | 9/2023 | Takahashi et al. |
| 11,793,926 | B2 | 10/2023 | Cook et al. |
| 2001/0031221 | A1 | 10/2001 | Wu et al. |
| 2002/0081228 | A1 | 6/2002 | Hui et al. |
| 2002/0098111 | A1 | 7/2002 | Nguyen et al. |
| 2002/0119075 | A1 | 8/2002 | Jacobs et al. |
| 2002/0122744 | A1 | 9/2002 | Hui et al. |
| 2003/0049165 | A1 | 3/2003 | Yamamoto et al. |
| 2003/0063997 | A1 | 4/2003 | Fryer et al. |
| 2003/0138347 | A1 | 7/2003 | Lin |
| 2004/0028556 | A1 | 2/2004 | Frost et al. |
| 2004/0170527 | A1 | 9/2004 | Jacobs et al. |
| 2004/0191114 | A1 | 9/2004 | Frost et al. |
| 2005/0042130 | A1 | 2/2005 | Lin et al. |
| 2005/0163655 | A1 | 7/2005 | Lin et al. |
| 2006/0008378 | A1 | 1/2006 | Imai et al. |
| 2006/0067856 | A1 | 3/2006 | Martensson et al. |
| 2006/0067976 | A1 | 3/2006 | Ferraro et al. |
| 2006/0088596 | A1 | 4/2006 | Labrecque et al. |
| 2006/0280646 | A1 | 12/2006 | Shiosawa |
| 2007/0003432 | A1 | 1/2007 | Christensen et al. |
| 2007/0006551 | A1 | 1/2007 | Sizer |
| 2007/0014691 | A1 | 1/2007 | Lin et al. |
| 2007/0048177 | A1 | 3/2007 | Lin et al. |
| 2007/0084144 | A1 | 4/2007 | Labrecque et al. |
| 2007/0092398 | A1 | 4/2007 | McDonald |
| 2007/0098591 | A1 | 5/2007 | Frinke et al. |
| 2007/0098592 | A1 | 5/2007 | Buczynski et al. |
| 2007/0154570 | A1 | 7/2007 | Miller et al. |
| 2007/0172383 | A1 | 7/2007 | Williams et al. |
| 2007/0231188 | A1 | 10/2007 | Jung et al. |
| 2007/0231192 | A1 | 10/2007 | Jung et al. |
| 2007/0231193 | A1 | 10/2007 | Jung et al. |
| 2007/0231194 | A1 | 10/2007 | Jung et al. |
| 2007/0231201 | A1 | 10/2007 | Roberts et al. |
| 2007/0231202 | A1 | 10/2007 | Roberts et al. |
| 2007/0258873 | A1 | 11/2007 | Wu et al. |
| 2007/0292305 | A1 | 12/2007 | Dempsey et al. |
| 2008/0025869 | A1 | 1/2008 | Kendall et al. |
| 2008/0085223 | A1 | 4/2008 | Jung et al. |
| 2008/0131342 | A1 | 6/2008 | Wu et al. |
| 2008/0202961 | A1 | 8/2008 | Sharp |

(56) References Cited

U.S. PATENT DOCUMENTS

| | | | |
|---|---|---|---|
| 2008/0226496 | A1 | 9/2008 | Rivkine et al. |
| 2008/0233251 | A1 | 9/2008 | Sizer |
| 2008/0279736 | A1 | 11/2008 | Frinke et al. |
| 2009/0071104 | A1 | 3/2009 | Fischer |
| 2009/0087921 | A1 | 4/2009 | Hill |
| 2009/0110596 | A1 | 4/2009 | Christensen et al. |
| 2009/0123330 | A1 | 5/2009 | Moller et al. |
| 2009/0208378 | A1 | 8/2009 | Jung et al. |
| 2009/0232697 | A1 | 9/2009 | Martensson et al. |
| 2009/0232703 | A1 | 9/2009 | Jung et al. |
| 2009/0324445 | A1 | 12/2009 | Kohler et al. |
| 2010/0034697 | A1 | 2/2010 | Weinberger et al. |
| 2010/0086447 | A1 | 4/2010 | Jung et al. |
| 2010/0090837 | A1 | 4/2010 | Jung et al. |
| 2010/0166603 | A1 | 7/2010 | Opie |
| 2010/0172795 | A1 | 7/2010 | Lothar |
| 2011/0076192 | A1 | 3/2011 | Robitaille et al. |
| 2011/0176959 | A1 | 7/2011 | Ko |
| 2011/0217204 | A1 | 9/2011 | Franciskovich et al. |
| 2011/0280765 | A1 | 11/2011 | Hirose et al. |
| 2012/0009085 | A1 | 1/2012 | Burger |
| 2012/0114524 | A1 | 5/2012 | Sigg |
| 2012/0189495 | A1 | 7/2012 | Franciskovich et al. |
| 2012/0213672 | A1 | 8/2012 | Adams et al. |
| 2012/0230870 | A1 | 9/2012 | Franciskovich et al. |
| 2013/0004380 | A1 | 1/2013 | Yoo |
| 2013/0004384 | A1 | 1/2013 | Yoo |
| 2013/0028794 | A1 | 1/2013 | Silvestri et al. |
| 2013/0084215 | A1 | 4/2013 | Fukui et al. |
| 2013/0105025 | A1 | 5/2013 | Fehr et al. |
| 2013/0156641 | A1 | 6/2013 | Paskalov |
| 2013/0236359 | A1 | 9/2013 | Burger |
| 2013/0296779 | A1 | 11/2013 | Kuehne et al. |
| 2014/0020331 | A1 | 1/2014 | Chin et al. |
| 2014/0109519 | A1 | 4/2014 | Hayakawa et al. |
| 2014/0109529 | A1 | 4/2014 | Hayakawa et al. |
| 2014/0154132 | A1 | 6/2014 | Frieze et al. |
| 2014/0170020 | A1 | 6/2014 | Hiruta |
| 2014/0193299 | A1 | 7/2014 | Leamy et al. |
| 2014/0205507 | A1 | 7/2014 | Yokoi et al. |
| 2014/0223862 | A1 | 8/2014 | Nicoletti et al. |
| 2014/0241953 | A1 | 8/2014 | Lho et al. |
| 2014/0288511 | A1 | 9/2014 | Tan-Malecki et al. |
| 2014/0301895 | A1 | 10/2014 | Opie et al. |
| 2014/0348703 | A1 | 11/2014 | Thomas et al. |
| 2015/0010432 | A1 | 1/2015 | Olson |
| 2015/0037204 | A1 | 2/2015 | Geiger et al. |
| 2015/0037205 | A1 | 2/2015 | Miyahara et al. |
| 2015/0044094 | A1 | 2/2015 | Cadieux et al. |
| 2015/0078961 | A1 | 3/2015 | Opie |
| 2015/0105734 | A1 | 4/2015 | Bryant et al. |
| 2015/0110670 | A1 | 4/2015 | Opie et al. |
| 2015/0182651 | A1 | 7/2015 | Tanimoto et al. |
| 2015/0183540 | A1 | 7/2015 | Lothar |
| 2015/0190566 | A1 | 7/2015 | Okihara |
| 2015/0197359 | A1 | 7/2015 | Nohara et al. |
| 2015/0205985 | A1 | 7/2015 | Jinadatha |
| 2015/0208648 | A1 | 7/2015 | Iwashita et al. |
| 2015/0209455 | A1 | 7/2015 | Turbett et al. |
| 2015/0239594 | A1 | 8/2015 | Batema |
| 2015/0273097 | A1 | 10/2015 | Murayama et al. |
| 2015/0274397 | A1 | 10/2015 | Dunn |
| 2015/0305342 | A1 | 10/2015 | Burke et al. |
| 2015/0305343 | A1 | 10/2015 | Burke et al. |
| 2015/0305344 | A1 | 10/2015 | Burke et al. |
| 2015/0306259 | A1 | 10/2015 | Deutschle et al. |
| 2015/0306266 | A1 | 10/2015 | Burke et al. |
| 2015/0313250 | A1 | 11/2015 | Itarashiki et al. |
| 2015/0320503 | A1 | 11/2015 | Bezdikian |
| 2015/0335826 | A1 | 11/2015 | Huet |
| 2015/0352238 | A1 | 12/2015 | Dufresne et al. |
| 2015/0373986 | A1 | 12/2015 | Burke et al. |
| 2016/0009433 | A1 | 1/2016 | Tanaka et al. |
| 2016/0090205 | A1 | 3/2016 | Py et al. |
| 2016/0114065 | A1 | 4/2016 | Thomas et al. |
| 2016/0121010 | A1 | 5/2016 | Harada et al. |
| 2016/0166765 | A1 | 6/2016 | Tan-Malecki et al. |
| 2016/0183522 | A1 | 6/2016 | Rovison et al. |
| 2016/0185474 | A1 | 6/2016 | Bronner et al. |
| 2016/0193375 | A1 | 7/2016 | Laflamme et al. |
| 2016/0199578 | A1 | 7/2016 | Tan-Malecki et al. |
| 2016/0199582 | A1 | 7/2016 | Tan-Malecki et al. |
| 2016/0199583 | A1 | 7/2016 | Tan-Malecki et al. |
| 2016/0200461 | A1 | 7/2016 | Broadbent et al. |
| 2016/0206767 | A1 | 7/2016 | Park et al. |
| 2016/0235873 | A1 | 8/2016 | Rovison, Jr. et al. |
| 2016/0235877 | A1 | 8/2016 | Ruley |
| 2016/0250367 | A1 | 9/2016 | Hijikata et al. |
| 2016/0257054 | A1 | 9/2016 | Hayakawa et al. |
| 2016/0257055 | A1 | 9/2016 | Hayakawa et al. |
| 2016/0263269 | A1 | 9/2016 | Hayakawa et al. |
| 2016/0272347 | A1 | 9/2016 | Procyshyn et al. |
| 2016/0296652 | A1 | 10/2016 | Leamy et al. |
| 2016/0303791 | A1 | 10/2016 | Hannafin et al. |
| 2016/0317688 | A1 | 11/2016 | Deprey et al. |
| 2016/0324998 | A1 | 11/2016 | Reed et al. |
| 2016/0325482 | A1 | 11/2016 | Hayakawa et al. |
| 2016/0347492 | A1 | 12/2016 | Lu et al. |
| 2016/0348160 | A1 | 12/2016 | Alvarez, Jr. et al. |
| 2016/0361450 | A1 | 12/2016 | Dufresne et al. |
| 2016/0375160 | A1 | 12/2016 | Hayakawa |
| 2016/0375167 | A1 | 12/2016 | Min et al. |
| 2017/0001744 | A1 | 1/2017 | Konze et al. |
| 2017/0007729 | A1 | 1/2017 | Bertomeu Asategui |
| 2017/0014539 | A1 | 1/2017 | Min et al. |
| 2017/0027175 | A1 | 2/2017 | Dunn |
| 2017/0035922 | A1 | 2/2017 | Stratman et al. |
| 2017/0035958 | A1 | 2/2017 | Thomas et al. |
| 2017/0049916 | A1 | 2/2017 | Ikeda |
| 2017/0056541 | A1 | 3/2017 | Sveningsson |
| 2017/0056923 | A1 | 3/2017 | Hioki et al. |
| 2017/0072081 | A1 | 3/2017 | Alvarez, Jr. et al. |
| 2017/0100284 | A1 | 4/2017 | Lerner |
| 2017/0100306 | A1 | 4/2017 | Weikart et al. |
| 2017/0100542 | A1 | 4/2017 | Norton et al. |
| 2017/0100543 | A1 | 4/2017 | Cabiri et al. |
| 2017/0106109 | A1 | 4/2017 | Morikawa et al. |
| 2017/0107008 | A1 | 4/2017 | Ichikawa |
| 2017/0129635 | A1 | 5/2017 | Hijikata et al. |
| 2017/0157316 | A1 | 6/2017 | Browne |
| 2017/0158365 | A1 | 6/2017 | Py |
| 2017/0166341 | A1 | 6/2017 | Hayakawa et al. |
| 2017/0166342 | A1 | 6/2017 | Hayakawa et al. |
| 2017/0173267 | A1 | 6/2017 | Ashmead et al. |
| 2017/0175069 | A1 | 6/2017 | Baker, Jr. et al. |
| 2017/0182259 | A1 | 6/2017 | Fukushi et al. |
| 2017/0189619 | A1 | 7/2017 | Constantineau et al. |
| 2017/0189843 | A1 | 7/2017 | Turbett et al. |
| 2017/0197003 | A1 | 7/2017 | Taggart |
| 2017/0197024 | A1 | 7/2017 | Kiminami et al. |
| 2017/0203043 | A1 | 7/2017 | Rusch et al. |
| 2017/0203052 | A1 | 7/2017 | Abe et al. |
| 2017/0203869 | A1 | 7/2017 | Lucani et al. |
| 2017/0208802 | A1 | 7/2017 | Franciskovich et al. |
| 2017/0217617 | A1 | 8/2017 | Sato et al. |
| 2017/0217661 | A1 | 8/2017 | Erickson |
| 2017/0224435 | A1 | 8/2017 | Godfrey et al. |
| 2017/0224858 | A1 | 8/2017 | Stibich |
| 2017/0258633 | A1 | 9/2017 | Vure et al. |
| 2017/0275581 | A1 | 9/2017 | Nishimura et al. |
| 2017/0281876 | A1 | 10/2017 | Odell et al. |
| 2017/0304476 | A1 | 10/2017 | Taggart et al. |
| 2017/0312378 | A1 | 11/2017 | Goncalves |
| 2017/0326262 | A1 | 11/2017 | Paver, Jr. |
| 2017/0348450 | A1 | 12/2017 | Akutsu |
| 2019/0105230 | A1 | 4/2019 | Arnott et al. |
| 2019/0106725 | A1 | 4/2019 | Cregger et al. |
| 2019/0106726 | A1 | 4/2019 | Cregger et al. |
| 2019/0224356 | A1 | 7/2019 | Nowruzi et al. |
| 2019/0231913 | A1 | 8/2019 | Ruley et al. |
| 2020/0101186 | A1 | 4/2020 | Shodder |
| 2020/0114029 | A1 | 4/2020 | Zhang et al. |
| 2020/0121817 | A1 | 4/2020 | Anraku et al. |
| 2020/0171244 | A1 | 6/2020 | Weikart et al. |

(56) References Cited

U.S. PATENT DOCUMENTS

2020/0230279 A1 7/2020 Nowruzi et al.
2020/0237997 A1 7/2020 Brockmeyer et al.
2020/0246510 A1 8/2020 Kobayashi et al.
2020/0246533 A1 8/2020 Patel et al.
2020/0297919 A1 9/2020 Hemminger et al.
2020/0306401 A1 10/2020 Cookson et al.
2020/0330634 A1* 10/2020 Herrig ........................ A61L 2/24
2020/0405898 A1 12/2020 Laflamme et al.
2021/0030946 A1 2/2021 Patel et al.
2021/0053165 A1 2/2021 Suzuki et al.
2021/0060258 A1 3/2021 Mismar et al.
2021/0077645 A1 3/2021 Mismar et al.
2021/0106707 A1 4/2021 Shodder
2021/0236236 A1 8/2021 Van Den Houdt et al.
2021/0261297 A1 8/2021 Bitong et al.
2021/0268145 A1 9/2021 Polo Martinez et al.
2021/0330826 A1 10/2021 Nayar
2021/0338871 A1 11/2021 Wallace et al.
2021/0346552 A1 11/2021 Eastep et al.
2021/0369899 A1 12/2021 Dufresne et al.
2021/0393830 A1 12/2021 Odim
2022/0001059 A1 1/2022 Beringer et al.
2022/0031438 A1 2/2022 Köhrer
2022/0111093 A1 4/2022 Storey et al.
2022/0133981 A1 5/2022 Dumont et al.
2022/0175979 A1 6/2022 Ryan et al.
2022/0241623 A1 8/2022 Ellison et al.
2022/0323681 A1 10/2022 Fujiwara et al.
2022/0355038 A1 11/2022 Matsumoto
2022/0371760 A1 11/2022 Redeker et al.
2022/0378962 A1 12/2022 Sias et al.
2023/0008104 A1 1/2023 Kwan et al.
2023/0020295 A1 1/2023 Fix
2023/0026520 A1 1/2023 Schutte et al.
2023/0048205 A1 2/2023 Lepschy et al.
2023/0056171 A1 2/2023 Krauss et al.
2023/0080971 A1 3/2023 Miller
2023/0113993 A1 4/2023 Bryant et al.
2023/0115895 A1 4/2023 Takahashi et al.
2023/0123589 A1 4/2023 Storey et al.
2023/0134454 A1 5/2023 Bush et al.
2023/0136536 A1 5/2023 Cardinali et al.
2023/0136844 A1 5/2023 Lindblad et al.
2023/0141766 A1 5/2023 Takahashi et al.
2023/0211026 A1 7/2023 Kawasaki et al.
2023/0240643 A1 8/2023 Cermak et al.
2023/0248898 A1 8/2023 Cook et al.
2023/0270903 A1 8/2023 Bohnert et al.
2023/0330287 A1 10/2023 Morrison
2023/0330323 A1 10/2023 Dominguez et al.
2023/0338599 A1 10/2023 Olson et al.
2023/0355818 A1 11/2023 Golkowski et al.
2023/0364289 A1 11/2023 Nowruzi et al.
2023/0398251 A1 12/2023 Nowruzi et al.
2023/0414859 A1 12/2023 Cook et al.

FOREIGN PATENT DOCUMENTS

CN 103083698 A 5/2013
CN 103491985 A 1/2014
CN 104174058 A 12/2014
CN 205515660 U 8/2016
CN 111467539 A 7/2020
EP 0302420 A2 2/1989
EP 0901380 A1 3/1999
EP 1019120 A1 7/2000
EP 1061974 A1 12/2000
EP 0846072 B1 5/2001
EP 1283061 A1 2/2003
EP 0774263 B1 3/2003
EP 1368066 A1 12/2003
EP 0880972 B1 2/2004
EP 1061975 B1 2/2004
EP 0971749 B1 7/2004
EP 0976415 B1 5/2005
EP 1759715 A1 3/2007
EP 1764115 A1 3/2007
EP 1675632 B1 9/2007
EP 1829577 A2 9/2007
EP 1884250 A1 2/2008
EP 1071487 B1 3/2008
EP 1924309 A1 5/2008
EP 1818069 B1 9/2008
EP 1973592 A2 10/2008
EP 1730999 B1 12/2008
EP 2121085 A1 11/2009
EP 1735014 B1 8/2010
EP 2094317 B1 9/2010
EP 2253548 A1 11/2010
EP 2253549 A1 11/2010
EP 2139527 B1 10/2011
EP 1819368 B1 3/2012
EP 2453928 A1 5/2012
EP 1839679 B1 8/2012
EP 1946075 B1 3/2013
EP 2593369 A1 5/2013
EP 2162652 B1 9/2013
EP 2125530 B1 12/2013
EP 2214724 B1 12/2013
EP 2730512 A1 5/2014
EP 2744523 A2 6/2014
EP 2846754 A1 3/2015
EP 2854762 A1 4/2015
EP 2862587 A1 4/2015
EP 1940476 B1 5/2015
EP 2869813 A1 5/2015
EP 2436407 B1 6/2015
EP 2436408 B1 6/2015
EP 1433705 B1 7/2015
EP 2687478 B1 8/2015
EP 2939649 A1 11/2015
EP 2604294 B1 12/2015
EP 2198790 B1 3/2016
EP 3009152 A1 4/2016
EP 2451489 B1 6/2016
EP 3037379 A1 6/2016
EP 1019120 B1 8/2016
EP 3056223 A1 8/2016
EP 3057633 A1 8/2016
EP 3070011 A1 9/2016
EP 2387422 B1 10/2016
EP 2949585 B1 12/2016
EP 3108902 A1 12/2016
EP 3116550 A1 1/2017
EP 3130359 A1 2/2017
EP 2394950 B1 4/2017
EP 2925392 B1 4/2017
EP 2407181 B1 5/2017
EP 3160471 A1 5/2017
EP 3162401 A2 5/2017
EP 3170756 A1 5/2017
EP 3192549 A1 7/2017
EP 2944583 B1 8/2017
EP 3017830 B1 8/2017
EP 3199189 A1 8/2017
EP 3202389 A1 8/2017
EP 3202447 A1 8/2017
EP 3202705 A1 8/2017
EP 3213786 A1 9/2017
EP 3170756 B1 9/2018
EP 1919777 B1 3/2019
EP 2858598 B1 4/2019
EP 2467084 B1 7/2019
EP 3558088 A2 10/2019
EP 3395374 B1 2/2020
EP 3630062 A2 4/2020
EP 3685860 A1 7/2020
EP 3512775 A4 9/2020
EP 3737426 A1 11/2020
EP 3369437 B1 2/2021
EP 3363470 B1 6/2021
EP 3782807 B1 6/2021
EP 3490732 B1 8/2022
EP 3875377 A4 8/2022

(56) References Cited

FOREIGN PATENT DOCUMENTS

| | | | |
|---|---|---|---|
| EP | 2604295 B2 | 9/2022 | |
| EP | 3116553 B1 | 9/2022 | |
| EP | 3918105 B1 | 1/2023 | |
| EP | 3934707 B1 | 1/2023 | |
| EP | 2817033 B1 | 2/2023 | |
| EP | 3600454 B1 | 6/2023 | |
| EP | 4188467 A1 | 6/2023 | |
| EP | 4249015 A1 | 9/2023 | |
| EP | 4262894 A1 | 10/2023 | |
| EP | 4281123 A1 | 11/2023 | |
| EP | 3746156 B1 | 12/2023 | |
| JP | 2009284951 A | 12/2009 | |
| JP | 2010201055 A | 9/2010 | |
| JP | 2010202448 A | 9/2010 | |
| JP | 2011050601 A | 3/2011 | |
| JP | 5074330 B2 | 11/2012 | |
| JP | 2016-120078 A | 7/2016 | |
| WO | 9107193 A1 | 5/1991 | |
| WO | WO-93/17726 A1 | 9/1993 | |
| WO | WO-1995012418 A1 | 5/1995 | |
| WO | WO-9708054 A1 | 3/1997 | |
| WO | WO-9744068 A1 | 11/1997 | |
| WO | WO-9807453 A1 | 2/1998 | |
| WO | WO-9819715 A1 | 5/1998 | |
| WO | WO-9848856 A1 | 11/1998 | |
| WO | WO-9856438 A1 | 12/1998 | |
| WO | WO-9915215 A1 | 4/1999 | |
| WO | WO-9927971 A2 | 6/1999 | |
| WO | WO-9945984 A1 | 9/1999 | |
| WO | WO-9945985 A1 | 9/1999 | |
| WO | WO-02072157 A1 | 9/2002 | |
| WO | WO-2005032627 A1 | 4/2005 | |
| WO | WO-2005067984 A1 | 7/2005 | |
| WO | WO-2006047325 A1 | 5/2006 | |
| WO | WO-2007024957 A1 | 3/2007 | |
| WO | WO-2007035621 A1 | 3/2007 | |
| WO | WO-2007083034 A2 | 7/2007 | |
| WO | 2007103278 A2 | 9/2007 | |
| WO | 2007130852 A2 | 11/2007 | |
| WO | WO-2008110890 A1 | 9/2008 | |
| WO | WO-2008111893 A1 | 9/2008 | |
| WO | WO-2009092430 A1 | 7/2009 | |
| WO | WO-2011006877 A1 | 1/2011 | |
| WO | WO-2011038487 A1 | 4/2011 | |
| WO | 2011069064 A1 | 6/2011 | |
| WO | WO-2011115428 A2 | 9/2011 | |
| WO | WO-2011117878 A1 | 9/2011 | |
| WO | WO-2011125133 A1 | 10/2011 | |
| WO | WO-2012007056 A1 | 1/2012 | |
| WO | 2012074768 A1 | 6/2012 | |
| WO | WO-2012075547 A1 | 6/2012 | |
| WO | WO-2012173562 A1 | 12/2012 | |
| WO | 2013008426 A1 | 1/2013 | |
| WO | WO-2013028537 A2 | 2/2013 | |
| WO | 2013126260 A1 | 8/2013 | |
| WO | 2013185776 A1 | 12/2013 | |
| WO | WO-2013178771 A1 | 12/2013 | |
| WO | WO-2013184270 A1 | 12/2013 | |
| WO | WO-2014005728 A1 | 1/2014 | |
| WO | WO-2014049712 A1 | 4/2014 | |
| WO | WO-2014049714 A1 | 4/2014 | |
| WO | 2014/079779 A1 | 5/2014 | |
| WO | WO-2014102987 A1 | 7/2014 | |
| WO | WO-2014187779 A1 | 11/2014 | |
| WO | 2015031414 A2 | 3/2015 | |
| WO | WO-2015055608 A1 | 4/2015 | |
| WO | WO-2015135887 A1 | 9/2015 | |
| WO | WO-2016052037 A1 | 4/2016 | |
| WO | WO-2016064288 A1 | 4/2016 | |
| WO | WO-2016068333 A1 | 5/2016 | |
| WO | WO-2016094658 A1 | 6/2016 | |
| WO | WO-2016140449 A1 | 9/2016 | |
| WO | 2016168156 A1 | 10/2016 | |
| WO | WO-2016165976 A1 | 10/2016 | |
| WO | 2016187080 A1 | 11/2016 | |
| WO | WO-2016180855 A1 | 11/2016 | |
| WO | WO-2016186502 A2 | 11/2016 | |
| WO | WO-2016191535 A2 | 12/2016 | |
| WO | WO-2017027876 A1 | 2/2017 | |
| WO | WO-2017030195 A1 | 2/2017 | |
| WO | WO-2017055462 A1 | 4/2017 | |
| WO | WO-2017057477 A1 | 4/2017 | |
| WO | WO-2017062407 A1 | 4/2017 | |
| WO | WO-2017062930 A1 | 4/2017 | |
| WO | WO-2017062931 A1 | 4/2017 | |
| WO | WO-2017062933 A1 | 4/2017 | |
| WO | WO-2017087798 A1 | 5/2017 | |
| WO | WO-2017087871 A1 | 5/2017 | |
| WO | WO-2017089197 A1 | 6/2017 | |
| WO | WO-2017103954 A1 | 6/2017 | |
| WO | WO-2017119582 A1 | 7/2017 | |
| WO | WO-2017126550 A1 | 7/2017 | |
| WO | WO-2017129232 A1 | 8/2017 | |
| WO | WO-2017129685 A1 | 8/2017 | |
| WO | WO-2017137665 A1 | 8/2017 | |
| WO | WO-2017139375 A1 | 8/2017 | |
| WO | WO-2017139573 A1 | 8/2017 | |
| WO | WO-2017158805 A1 | 9/2017 | |
| WO | WO-2018182929 A1 * | 10/2018 | ............ A61L 2/208 |
| WO | 2018217995 A1 | 11/2018 | |
| WO | WO-2018215580 A1 | 11/2018 | |
| WO | 2019063785 A1 | 4/2019 | |
| WO | 2019063786 A1 | 4/2019 | |
| WO | 2019084203 A1 | 5/2019 | |
| WO | WO-2020183696 A1 * | 9/2020 | ............ A61L 2/208 |
| WO | 2021021925 A1 | 2/2021 | |
| WO | 2021056020 A1 | 3/2021 | |
| WO | 2022034395 A1 | 2/2022 | |
| WO | 2022081276 A1 | 4/2022 | |
| WO | 2022195029 A1 | 9/2022 | |
| WO | 2022202382 A1 | 9/2022 | |
| WO | 2022217192 A1 | 10/2022 | |
| WO | 2022229741 A1 | 11/2022 | |
| WO | 2022241048 A1 | 11/2022 | |
| WO | 2022272257 A1 | 12/2022 | |
| WO | 2023039458 A1 | 3/2023 | |
| WO | 2023041697 A1 | 3/2023 | |
| WO | 2023073622 A1 | 5/2023 | |
| WO | 2023097258 A1 | 6/2023 | |
| WO | 2023114123 A1 | 6/2023 | |
| WO | 2023117876 A1 | 6/2023 | |
| WO | 2023123799 A1 | 7/2023 | |
| WO | 2023148750 A1 | 8/2023 | |
| WO | 2023150685 A1 | 8/2023 | |
| WO | 2023157540 A1 | 8/2023 | |
| WO | 2023167982 A2 | 9/2023 | |
| WO | 2023228073 A1 | 11/2023 | |

OTHER PUBLICATIONS

International search report and Written opinion for the application PCT/US2018/021013 dated May 11, 2018 (9 pages).
Machine Translation of JP2009284951 (Year: 2009).
Fischer et al., "Specific Immune Response to Phospholipase B-Like 2 Protein, a Host Cell Impurity in Lebrikizumab Clinical Material," The AAPS Journal, vol. 19, No. 1, pp. 254-263, Oct. 13, 2016 (10 pages).
International Search Report in International Application No. PCT/US2022/071436, mailed Jul. 25, 2022 (7 pages).

* cited by examiner

METHODS AND SYSTEMS FOR STERILIZATION

CROSS-REFERENCE TO RELATED APPLICATIONS

This application claims priority to U.S. Provisional Patent Application No. 63/172,457, filed on Apr. 8, 2021, which is hereby incorporated by reference in its entirety.

FIELD OF THE DISCLOSURE

Various embodiments of the present disclosure relate to sterilization systems and methods for sterilization. More specifically, some embodiments of the present disclosure relate to systems and methods for chemical sterilization (e.g., moist chemical sterilization) of medical products, including terminal sterilization of drug delivery devices (e.g., pre-filled syringes) using vaporized sterilant, such as vaporized hydrogen peroxide. Additionally, embodiments of the present disclosure relate to systems and methods for monitoring and controlling environments and/or conditions within a sterilization apparatus or process.

INTRODUCTION

Chemical sterilization processes, such as processes using ethylene oxide, vaporized hydrogen peroxide, vaporized peracetic acid, and the like, offer many advantages, such as the ability to sterilize a load at relatively low temperatures (e.g., at less than 50° C.), and without the need to enter a deep vacuum (e.g., without decreasing a pressure to below 100 millibars). Such sterilization processes may be particularly useful in the sterilization of medical devices and medical products that are sensitive to extreme temperatures and/or pressures.

Processes using chemical sterilants include steps to ensure that the sterilant reaches all parts of a load that need to be sterilized, and that after sterilization has taken place, the sterilant is removed from the load to a degree that ensures the safety and efficacy of any products that were sterilized. Removing sterilant from the load may be referred to as aerating the load. Additionally, sterilization processes may benefit from improvements that reduce the time and resources required to sterilize and aerate/dry a load.

In particular, the use of vaporized chemicals, such as vaporized hydrogen peroxide, may raise certain challenges. The distribution of vaporized sterilant in a sterilization system, its behavior (e.g., condensation, evaporation, etc.), and its interaction with a sterilization load (e.g., adsorption to materials of the load), may affect its efficacy and how easily it may be removed from the load.

SUMMARY

Embodiments of the present disclosure may be directed to a sterilization method. The method may include pre-conditioning a sterilization apparatus including a sterilization chamber comprising a sterilization load. Pre-conditioning the sterilization apparatus may include increasing a temperature of a portion of the sterilization apparatus to a temperature greater than a maximum temperature of the sterilization load. The method may further include executing a sterilization phase and executing an aeration phase. The sterilization phase may include a plurality of sterilization pulses. The aeration phase may include a plurality of aeration pulses, wherein the plurality of aeration pulses includes a primary aeration pulse and a secondary aeration pulse. The primary aeration pulse may comprise achieving a first vacuum pressure within the sterilization chamber, wherein the first vacuum pressure is less than 650 millibar. The primary aeration pulse may further comprise, after a first vacuum hold, increasing the pressure of the sterilization chamber to a pressure greater than 700 millibar. The secondary aeration pulse may comprise achieving a second vacuum pressure within the sterilization chamber, wherein the second vacuum pressure is less than 650 millibar. The secondary aeration pulse may further comprise, after a second vacuum hold, adding air to the sterilization chamber while exhausting the sterilization apparatus.

In some embodiments, the method may further include, after the sterilization phase and prior to the aeration phase, adding a dry air to the sterilization chamber. The plurality of aeration pulses may include a first primary aeration pulse, followed by a first secondary aeration pulse, followed by a second primary aeration pulse, followed by a secondary aeration pulse. The portion of the sterilization apparatus may include an inlet and, optionally, a conduit connecting a VHP injector to the inlet. Each sterilization pulse may comprise achieving a sterilization pressure within the sterilization chamber, and, when the sterilization chamber is at the sterilization pressure, adding vaporized hydrogen peroxide to the sterilization chamber. The sterilization pressure may be less than or equal to 650 millibars. The sterilization chamber may include a piston or diaphragm configured to adjust the pressure of the sterilization chamber. The method may further comprise, after the sterilization pulse, creating a low frequency pressure wave with the piston or diaphragm. The low frequency pressure wave may move liquid hydrogen peroxide in contact with the sterilization load. The sterilization load may include a Tyvek envelope.

In some embodiments of the present disclosure, a sterilization method may include executing a sterilization phase and executing an aeration phase. The sterilization phase may include first, second, and third sterilization pulses. Each sterilization pulse may include achieving a sterilization pressure within the sterilization chamber, and, when the sterilization chamber is at the sterilization pressure, adding an amount of vaporized hydrogen peroxide to the sterilization chamber. The aeration phase may comprise achieving a vacuum pressure within the sterilization chamber, wherein the vacuum pressure is less than 650 millibar. The aeration phase may further comprise, after a vacuum hold, adding air to the sterilization chamber while exhausting the sterilization apparatus. The amount of vaporized hydrogen peroxide added to the sterilization chamber during the first sterilization pulse may be sufficient to establish a lethal concentration of hydrogen peroxide in the chamber. The amount of vaporized hydrogen peroxide added to the sterilization chamber during the second sterilization pulse may be less than the amount of vaporized hydrogen peroxide added to the sterilization chamber during the first sterilization pulse. The amount of vaporized hydrogen peroxide added to the sterilization chamber during the third sterilization pulse may be less than the amount of vaporized hydrogen peroxide added to the sterilization chamber during the second sterilization pulse.

In some embodiments, the method may further include repeating the first sterilization pulse at least once before the second sterilization pulse. The method may further include repeating the third sterilization pulse at least twice. The amount of vaporized hydrogen peroxide added to the sterilization chamber during the first sterilization pulse may include at least 0.1 moles of hydrogen peroxide per cubic meter of volume of the sterilization chamber. Each sterilization pulse may further include: (i) adding gas into the sterilization chamber to increase the pressure to a hold pressure, and (ii) decreasing the pressure of the sterilization chamber to the sterilization pressure. Step (i) may take more time than step (ii). The hold pressure may be greater than 700 millibar. Each sterilization pulse may further comprise maintaining the pressure of the sterilization chamber for a first hold time, before step (i). Each sterilization pulse may further comprise maintaining the pressure of the sterilization chamber for a second hold time, after step (ii). The second hold time may be longer than the first hold time. The sterilization chamber may include a distribution manifold, an inlet, and a chamber wall, and the method may further comprise maintaining a temperature of the chamber wall to be approximately the same as a temperature of the inlet or a temperature of the distribution manifold, during the first, second, and/or third sterilization pulses.

Further embodiments of the present disclosure may include a sterilization method comprising: a first sterilization pulse, a plurality of second sterilization pulses, and a plurality of third sterilization pulses. The first sterilization pulse may include adding a first amount of vaporized hydrogen peroxide to a sterilization chamber, wherein the first amount is sufficient to establish a lethal concentration of hydrogen peroxide in the sterilization chamber. Each second sterilization pulse may include adding a second amount of vaporized hydrogen peroxide to the sterilization chamber, wherein the second amount is less than the first amount. Each third sterilization pulse includes adding a third amount of vaporized hydrogen peroxide to the sterilization chamber, wherein the third amount is less than the second amount.

In some embodiments, the method may further comprise executing an aeration pulse. The aeration pulse may comprise (i) lowering the pressure of the sterilization chamber to a first aeration pressure, and (ii) increasing the pressure of the sterilization chamber to a second aeration pressure. A rate of pressure change in step (ii) may be at least 100 millibar per minute faster than a rate of pressure change in step (i). The first aeration pressure may be less than 650 millibar. The second aeration pressure may be greater than 700 millibar. The method may further comprise, prior to the aeration phase, removing moisture from the sterilization chamber by passing the contents of the sterilization chamber through a condenser. The sterilization chamber may comprise a load, where the load includes a Tyvek material defining an interior of the load and an exterior of the load. After the plurality of third sterilization pulses, a concentration of hydrogen peroxide in the interior of the load may be approximately equal to a concentration of hydrogen peroxide in the exterior of the load.

BRIEF DESCRIPTION OF THE DRAWINGS

The accompanying drawings, which are incorporated into and constitute a part of this specification, illustrate various exemplary embodiments and, together with the description, serve to explain the principles of the disclosed embodiments. The drawings show different aspects of the present disclosure. Where appropriate, reference numerals illustrating like structures, components, materials and/or elements in different figures are labeled similarly. It is understood that various combinations of the structures, components, and/or elements, other than those specifically shown, are contemplated and are within the scope of the present disclosure.

There are many inventions described and illustrated herein. The described inventions are neither limited to any single aspect nor embodiment thereof, nor to any particular combinations and/or permutations of such aspects and/or embodiments. Moreover, each of the aspects of the described inventions, and/or embodiments thereof, may be employed alone or in combination with one or more of the other aspects of the described inventions and/or embodiments thereof. For the sake of brevity, certain permutations and combinations are not discussed and/or illustrated separately herein. Notably, an embodiment or implementation described herein as "exemplary" is not to be construed as preferred or advantageous, for example, over other embodiments or implementations; rather, it is intended reflect or indicate the embodiment(s) is/are "example" embodiment(s).

DETAILED DESCRIPTION

Figure 1A:
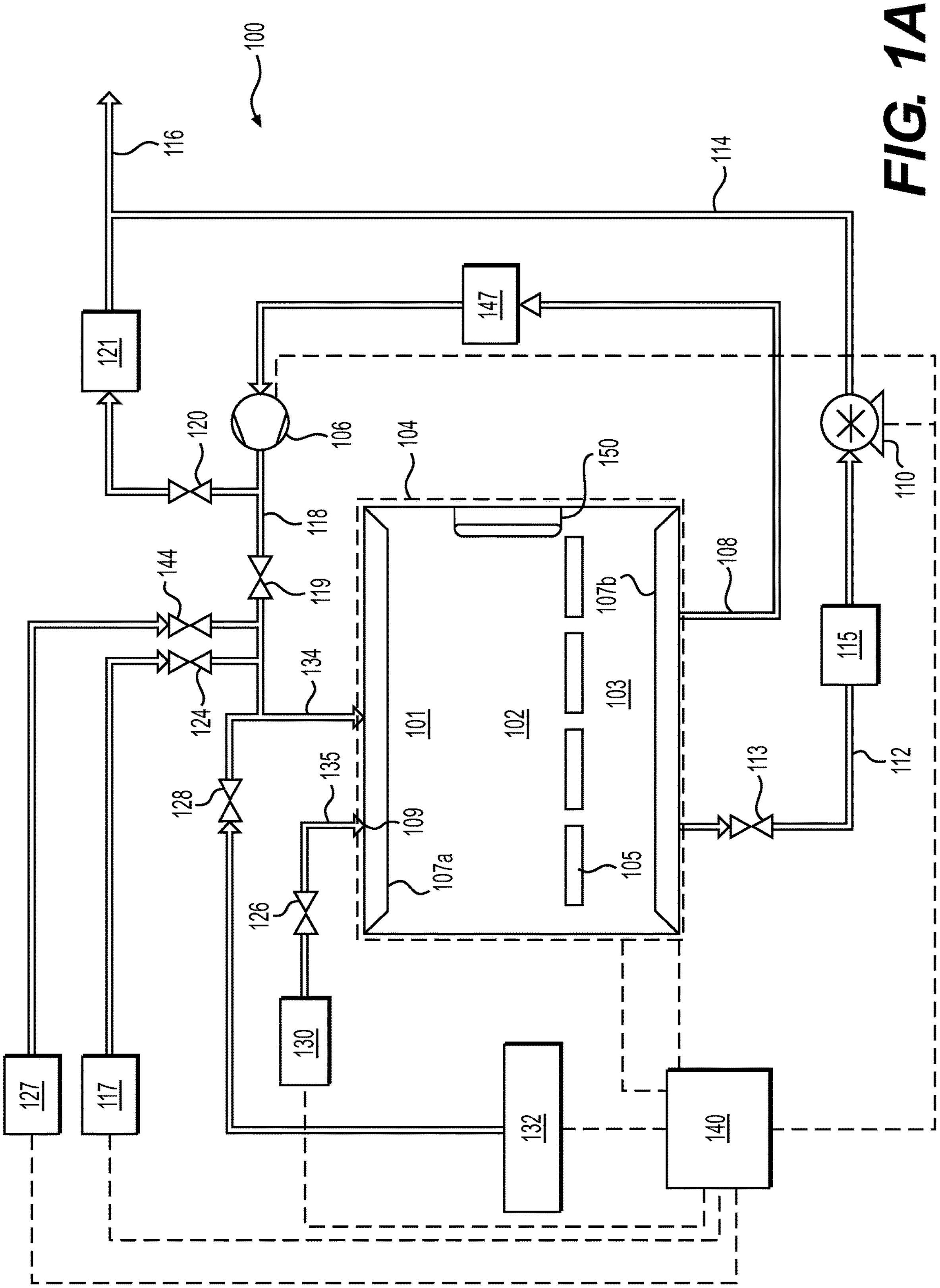
FIG. 1A is a schematic drawing of an exemplary sterilization system that may be used for sterilization of medical products.

As used herein, the terms "comprises," "comprising," "include," "have," "with," or any other variation thereof, are intended to cover a non-exclusive inclusion, such that a process, method, article, or apparatus that comprises a list of elements need not include only those elements, but may include other elements not expressly listed or inherent to such process, method, article, or apparatus. The term "exemplary" is used in the sense of "example," rather than "ideal." Any implementation described herein as exemplary is not to be construed as preferred or advantageous over other implementations. Further, the terms "first," "second," and the like, herein do not denote any order, quantity, or importance, but rather are used to distinguish one element from another. Similarly, terms of relative orientation, such as "front side, "top side," "back side," "bottom side," "upper," "lower," etc. are referenced relative to the described figures.

As used herein, the terms "about" and "approximately" are meant to account for possible variation of ±10% in a stated numeric value. All measurements reported herein are understood to be modified by the term "about," or the term "approximately," whether or not those terms are explicitly used, unless explicitly stated otherwise. As used herein, the singular forms "a," "an," and "the" include plural referents unless the context clearly dictates otherwise. Moreover, in the claims, values, limits, and/or ranges means the value, limit, and/or range +/−10%.

As used in the present disclosure, the term "sterilization" refers to achieving a level of sterility appropriate for a formulated drug substance or drug product for commercial distribution and use. Such a level of sterility may be defined in, for example, regulatory guidelines or regulations, such as guidelines released by the U.S. Food and Drug Administration. In some embodiments, such a level of sterility may include, for example, a 6-log reduction in microbial populations of biological indicators placed on an outside or inside surface of a drug product (e.g., an outside surface of a syringe or an inside surface of a blister pack). In other embodiments, such a level of sterility may include, for example, a 9-log or 12-log reduction in microbial populations of biological indicators. Sterilization refers to achieving such an appropriate level of sterility while also achieving a sufficiently low level of residual sterilizing chemicals (e.g., vaporized hydrogen peroxide, ethylene oxide, etc.) for commercial distribution and use. Such a low level of residual sterilizing chemical may also be defined in regulatory guidelines or regulations.

As used in the present disclosure, the term "terminal sterilization" refers to the sterilization of a drug product in a container or packaging, such as in a primary packaging component, or in both primary and secondary packaging components, suitable for commercial distribution and use.

As used in the present disclosure, the term "medical product" refers to a product for medical use on a living animal. The term "medical product" includes, for example, drug products, formulated drug substances, medical implants, medical instruments, or combinations thereof. For example, the term "medical product" may refer to a syringe containing a formulated drug substance, such as a parenteral or an ophthalmic syringe. Other exemplary medical products include, e.g., suppository applicators and medication, transdermal drug delivery devices, medical implants, needles, cannulas, medical instruments, and any other product requiring sterilization prior to an intended medical use.

As used in the present disclosure, the term "formulated drug substance" refers to a composition containing at least one active ingredient (e.g., a small molecule, a protein, a nucleic acid, or a gene therapy medicament) and an excipient, prepared for medical distribution and use. A formulated drug substance may include fillers, coloring agents, and other active or inactive ingredients.

As used in the present disclosure, the term "drug product" refers to a dosage form that contains a formulated drug substance, such as a finished dosage form for an active ingredient. A drug product may include packaging for commercial distribution or use, such as a bottle, vial, or syringe.

As used in the present disclosure, the term "vaporized chemical" refers to a chemical that has been converted into a substance that may be diffused or suspended in air. In some instances, a vaporized chemical may be a chemical that has been combined with water and then converted into a substance that may be diffused or suspended in air.

As used in the present disclosure, the term "fluid" refers to a liquid, semi-liquid, vapor, or gas including oxygen, hydrogen, nitrogen, or a combination thereof.

Embodiments of the present disclosure relate to systems and methods for the use of vaporized chemicals in sterilization processes, such as processes for sterilizing medical products. For example, embodiments of the present disclosure may relate to systems and methods for the terminal sterilization of medical products using vaporized hydrogen peroxide (VHP). More particularly, embodiments of the present disclosure may relate to, e.g., systems and methods for the terminal sterilization of medical products, such as pre-filled syringes (PFS).

It is generally desired that exposure to sterilization cycles be effective while having no adverse impact and minimized risk of damage or alteration to the load being sterilized. Medical products that undergo terminal sterilization, such as PFS, may thus require sterilization equipment, machinery, controls, cycle, and methods to address certain constraints and requirements in order to achieve appropriate sterilization and/or avoid damage to the medical products and/or devices, formulated drug substances, drug products, or other products. Such constraints and requirements may include, e.g.:

Medical products may be located within different parts of a sterilization chamber (e.g., quadrants or zones), which may, during a sterilization cycle, exhibit conditions that may differ from those in other parts of the chamber, such as temperature, pressure, water vapor concentration, humidity, or sterilant concentration. Such differing conditions may affect sterilization efficacy. Maintenance of a consistent environment throughout a sterilization chamber may be beneficial to ensuring sterilization efficacy is adequate as to all parts of a load.

An environment within a sterilization chamber may change during a sterilization cycle, in a way that affects the movement, state, or efficacy of sterilant and/or fluids in the chamber. For example, as sterilant is added to a chamber, a pressure within the chamber may increase. The pressure within the chamber may affect the ratio of condensed sterilant to vaporized sterilant. Changes in temperature, humidity, or other environmental characteristics may also affect how sterilant within the chamber and additional sterilant added to the chamber behaves. Sterilization systems and methods that adapt to changes in the environment or climate within the sterilization chamber during a sterilization phase, to maximize efficacy of sterilization, may be beneficial. Systems and methods that adapt to changes in the environment or climate of an area to maximize aeration and drying of that area may also be beneficial.

Medical products may be densely packed. For example, bulk packaged medical products may contain a large sum of fully assembled, packaged, and labeled medical products. In the case of terminal sterilization, sterilizing agents may need to traverse several layers of packaging materials, container materials, and/or labels, to effectively sterilize all aspects of a load, and to be appropriately removed from all aspects of the load. In some cases, packaging may include semi-permeable materials, which select for sterilizing agents in a particular phase (e.g., vapor).

In the case of some types of sterilization, such as terminal sterilization, sterilizing agents may need to traverse a semi-permeable membrane, either by heat or by mass, to sterilize the exterior of each medical product as well as the interior of packaging elements. Sterilizing agents may also need to be successfully removed through, e.g., a semi-permeable membrane, to avoid remaining as residue on a medical product. Traversal of a semi-permeable membrane may only be possible for sterilizing agent in a particular form, such as a vapor or gas.

Packaging for medical products may resist penetration of sterilization materials, and/or may be sensitive to temperature and pressure changes caused by sterilization. For example, a syringe may be packaged in a plastic 'blister' configured to house the syringe and restrict it from movement. Such a blister may be only somewhat permeable to sterilization materials, and/or may be sensitive to changes in pressure.

Using a combination of a vaporized chemical sterilant (e.g., VHP) and vaporized water in an environment in which temperature and pressure may be precisely controlled may allow for specific management of the environment to maximize the sterilant's contact with a sterilization load during a sterilization phase, and/or to maximize removal of the sterilant from a load during one or more subsequent aeration or drying phases. Some embodiments of the present disclosure are related to precisely controlling temperature, pressure, humidity, exposure times, and other environmental conditions. Environmental conditions may be adjusted in any portion of the sterilizing apparatus, before, during, and/or after a sterilization process is performed with the apparatus. For example, the environment of one or more portions of the apparatus where sterilant is introduced or removed, may be maintained or controlled to be within pre-determined conditions. As such, embodiments of the present disclosure may aid in improving the introduction and/or removal of a chemical sterilant in a sterilization apparatus (e.g., between the sterilization apparatus and an exterior of the apparatus, or between portions of the apparatus). Some embodiments of the present disclosure may be used in combination with disclosures of WIPO Publication No. WO 2018/182929, filed Mar. 6, 2018, which is herein incorporated by reference in its entirety.

Several characteristics of a vaporized chemical sterilant may (positively or negatively) affect the safety, efficacy, efficiency, and other aspects of sterilization processes for medical products. For example:

Chemical sterilant vapors and water vapors in an environment may adsorb to, and/or condense on, surfaces having relatively cooler temperatures within the environment. For example, during vapor sterilization of PFS loads, "cold spots" created by aqueous, high heat capacity, liquid product in each PFS, may serve to attract vapor adsorption and promote surface condensation. Moreover, changing the temperature of an environment (e.g., heating a sterilization chamber), may generate areas of relative warmth and coolness within the environment, which may in turn affect the relative temperature of a load in an area of relative warmth or coolness. For example, heating a sterilization chamber using a temperature control jacket may result in areas of the chamber closest to the jacket (e.g., a periphery of the chamber) becoming warmer than areas farther from the jacket (e.g., a middle of the chamber). The ambient heat in warmer areas may cause parts of a sterilization load in those areas to become relatively warmer as well. Chemical sterilant vapors and water vapors may preferentially adsorb to the surfaces of areas having relatively cooler temperatures as compared to the rest of the environment ("cold spots"); thus, vaporized chemical sterilant (e.g., VHP) may not distribute evenly between areas of relative warmth and coolness. While cooler areas may be subject to more thorough exposure to sterilant, warmer areas may experience more thorough aeration and drying.

VHP may preferentially adsorb onto surfaces as compared to water vapor, due to the fact that hydrogen peroxide is more dense and less volatile than water. In some instances, hydrogen peroxide and water vapor may be adsorbing and condensing on surfaces at the same time, with hydrogen peroxide adsorbing and condensing in greater quantities and percentages as compared to the water vapor, and in closer proximity to the surfaces of the sterilization load than the water vapor.

Multiple layers of adsorption may form on a single surface in a sterilization environment. In some instances, each layer of adsorption and/or condensation further away from the surface may contain less hydrogen peroxide and more water vapor, such that a gradient of hydrogen peroxide to water is formed on the surface. Hydrogen peroxide may preferentially adsorb and condense closer to the surface than water because of the thermodynamic behavior of binary mixtures of VHP and water vapor near or at saturation (e.g., a binary mixture of hydrogen peroxide and water at vapor/liquid equilibrium). Vapor/liquid equilibrium may be analogous to gas/adsorbate equilibrium for binary mixtures of VHP and water vapor in sterilization applications.

In some instances, condensed or adsorbed hydrogen peroxide may be difficult to remove from surfaces. For example, condensation of water vapor over the condensed/adsorbed hydrogen peroxide, or adsorption of water around the condensed/adsorbed hydrogen peroxide, may trap the hydrogen peroxide on the sterilized surface, or otherwise inhibit the removal of the hydrogen peroxide.

Differences in pressure throughout an environment, such as a sterilization chamber, may also affect efficacy of vaporized chemical sterilant. For example, sterilization efficacy may be greater at compressed air injection points of a sterilization chamber, compared to the rest of the chamber. Without being limited by theory, this may be due to the nature of gas within the chamber at a partial vacuum. Areas local to a compressed air injection point may experience a pressure wave or pulse having greater magnitude than areas farther from a compressed air injection point while the chamber is saturated with chemical sterilant. The pressure wave may cause greater condensation of chemical sterilant in areas local to compressed air injection points.

In some cases where it is desired that a sterilant traverse a semi-permeable membrane of a load to sterilize an interior area or volume covered by the membrane, a delay in migration of at least a portion of sterilant through the load has been observed. For example, in sterilization loads including a semi-permeable Tyvek membrane, the hydrogen peroxide concentration within the membrane lagged, or was slower to equilibrate with, the hydrogen peroxide concentration outside of the membrane. No such delay or lag was observed with respect to water concentration. Thus, the relative strength of a sterilant may be lower for loads or portions of a load within a semi-permeable membrane (either for part or for all of a sterilization cycle) as compared to the strength of the sterilant outside of the membrane.

The speed with which pressure increases during introduction of vaporized sterilant into a sterilization chamber may negatively affect sterilization efficacy. A pressure increase to some degree may benefit introduction of sterilant to a load, promoting adsorption of the sterilant to the load. However, excessive pressure increases when an environment is at or near a level of VHP saturation, for example, may result in aggressive condensation of the VHP, which may compromise sterilization efficacy or subsequent aeration or drying efficacy. Allowing the pressure of an environment to be held at a level where vaporized sterilant may condense over time may result in over-condensation of vaporized sterilant. Conversely, decreasing the pressure of an environment after introducing vaporized sterilant (e.g., VHP) may allow more sterilant to remain in a vapor phase, which may improve the sterilant's efficacy in migrating through semi-permeable membranes and effecting sterilization of the interior(s) of a sterilization load.

During a sterilization phase (e.g., a sterilization pulse) increases in pressure may be faster than decreases in pressure (e.g., the rate of pressure increase during a sterilization pulse may be 150 millibar/minute faster than the rate of pressure decrease during the same pulse). This may promote travel of the sterilant (e.g., promote travel of sterilant through one or more layers of packaging). During aeration, the reverse may be employed to promote travel of sterilant from within layers of packaging to exterior of the packaging, and through the exhaust of the sterilization apparatus. For example, the rate of pressure decrease during an aeration pulse may be 150 millibar faster than the rate of pressure increase during the same pulse. Increased chamber temperatures may also increase the efficiency of aeration.

The saturation level of the sterilization chamber may also factor into the rate or direction of pressure adjustment. For example, pressure increases near atmospheric pressure should be avoided while the sterilization chamber is near saturation. For example, greater pressure changes may be used a lower sterilant concentrations, while large pressure changes at high sterilant concentrations may cause excess condensation, decreasing the efficiency of the sterilization.

Sterilizing agents may also need to be successfully removed from the load to avoid remaining as residue on or in a medical product. For example, in embodiments utilizing packaging including a semi-permeable membrane, traversal of the semi-permeable membrane may only be possible for sterilizing agent in a particular form, such as a vapor or gas. In some cases, stimulating mechanical movement (e.g., rocking, rotation, agitation, etc.) of some or all of a load may dislodge sterilant molecules adhered to a load, and may promote aeration and removal of a sterilant from the load. Low frequency pressure waves or acoustics generated within the sterilization chamber (for example, via a diaphragm or piston located within the chamber) may dislodge sterilant adhered to the load.

Immediately increasing the pressure following a sterilization pulse can cause unnecessary condensation and result in less efficacious aeration. Prior to aeration, the humidity of the sterilization chamber may be reduced to prevent excessive condensation. For example, the contents of the closed system may be passed through a condenser (e.g., a desiccant wheel) to reduce the humidity of the environment. In addition or alternatively, dry air may be injected, prior to, or during exhaustion, to reduce the overall humidity of the system.

Systems and methods disclosed herein may advantageously be used in improving the efficacy of sterilization, aeration, and/or drying cycles involving vaporized chemical sterilants. For example, systems and methods disclosed herein may provide for full (e.g., 100%) sterilization of medical products using VHP, followed by full (e.g., 100%) removal of VHP from sterilized products. Systems and methods disclosed herein may, e.g., increase efficiency, safety, and efficacy of sterilization, and/or decrease sterilization cycle time. While aspects of the present disclosure may be described with respect to the use of VHP in terminal sterilization of PFS, the present disclosure contemplates using the techniques and systems herein for movement of VHP and other chemical sterilants in other contexts as well (e.g., sterilization of other products, cleaning areas, addition/removal of vaporized chemical to any environment, etc.).

The present disclosure also contemplates performance of "moist chemical sterilization," by which chemical sterilization may be achieved in the presence of water vapor. Comparison of "moist chemical sterilization" to "chemical sterilization" may be analogous, in some cases, to comparison of "moist heat sterilization" to "heat sterilization." In some instances, moist chemical sterilization may be a more effective and efficient means of achieving sterilization than chemical sterilization technology that currently exists, in the same way that "moist heat sterilization" is considered to be, in some cases, more effective and efficient than only "heat sterilization."

"Moist chemical sterilization" may take place when environmental conditions of relatively high chemical concentration, high water vapor concentration, and high pressure (e.g., above 400 millibar) act in concert to force the chemical and water vapor to behave as a binary mixture. In order to achieve the desired relatively high chemical concentration, high water vapor concentration, and high pressure, the area to be sterilized may be saturated with a combination of water vapor and sterilizing chemical (e.g., VHP), forcing vapor to condense on surfaces of the load. Most commercially available hydrogen peroxide is available and sold as aqueous liquid mixtures in varying concentrations (e.g., 3%, 15%, 35%, 59%), and thus, vaporizing hydrogen peroxide will generally simultaneously include vaporizing water.

Referring now to the figures, FIG. 1A depicts in schematic form an exemplary sterilization system 100 for use in methods of the present disclosure. It is to be understood that sterilization system 100 is merely exemplary, and methods disclosed herein may be used in many other systems, environments, and/or parts thereof. Sterilization system 100 includes a sterilization chamber 102, surrounded by a temperature control jacket 104. Sterilization chamber 102 has an interior cavity, including an upper interior 101 and a lower interior 103. Sterilization chamber 102 is configured to house a sterilization load (e.g., a load including one or more products 105) for sterilization. An inlet conduit 134, fluidly connected to sterilization chamber 102, is configured to allow various fluids to enter sterilization chamber 102. The inlet conduit 134 may be connected to one or more distribution manifolds (e.g., diffusion plates, spray balls, or other structure configured to distribute a gas throughout the chamber). In the examples shown in FIGS. 1A and 1B, a first distribution manifold 107*a* is located near upper interior 101 and a second distribution manifold 107*b* is located near lower interior 103. Placement of distribution manifolds 107*a*,107*b* on opposing sides of sterilization chamber 102 may promote even distribution of sterilant, air, or other introduced material.

Inlet conduit 134 may connect to both first distribution manifold 107*a* and second distribution manifold 107*b*. In some embodiments, second distribution manifold 107*b* is connected to a different inlet conduit than first distribution manifold 107*a*.

A second inlet conduit 135 is also fluidly connected to sterilization chamber 102, also to allow fluids to enter sterilization chamber 102 via an inlet 109. For example, dry air from dry air supply 130 may be introduced into sterilization chamber 102 via inlet 109.

A blower 106 is fluidly connected to sterilization chamber 102 via a blower exit conduit 108. A blower circulation conduit 118 fluidly connects blower 106 to move fluids from blower exit conduit 108 either towards an exhaust 116, or back towards sterilization chamber 102 via inlet conduit 134. In some embodiments, blow exit conduit 108 may include, or be coupled to, a condenser 147. Condenser 147 may include a desiccate wheel or other structure configured to remove water from the fluid passing through blower exit conduit 108. An exhaust valve 120 is located between blower circulation conduit 118 and exhaust 116, and selectively closes or opens a connection between blower circulation conduit 118 and exhaust 116. A recirculation valve 119 is located between blower circulation conduit 118 and inlet conduit 134, and selectively closes or opens a connection between blower 106 (e.g., via blower circulation conduit 118) and inlet conduit 134.

Blower 106 may circulate air at a rate greater than 500 cubic feet per minute (cfm). In some embodiments, the rate of air circulation maintained by blower 106 may be less than 1000 cfm. If blower 106 is moving too much fluid, sterilant will be displaced near distribution manifolds 107*a*, 107*b*, decreasing the sterilization efficiency.

A vacuum pump 110 may be fluidly connected to sterilization chamber 102, via a vacuum conduit 112. Vacuum conduit 112 may include, or be connected to, a catalytic converter 115. A vacuum valve 113 located between sterilization chamber 102 and vacuum conduit 112, may selectively allow, partially allows, or block, flow from sterilization chamber 102 (e.g., through catalytic converter 115) to vacuum pump 110. A vacuum exhaust conduit 114 fluidly connects vacuum pump 110 to exhaust 116.

Sterilization system 100 may include several supplies of air and/or vapor from which fluid may be introduced into sterilization chamber 102 via inlet conduit 134 or inlet conduit 135. A dry makeup air supply 127 may be configured to supply dry makeup air to sterilization chamber 102 via inlet conduit 134. In some embodiments, dry makeup air supply 127 is compressed dry air. A dry air valve 144 may be coupled to the fluid connection between dry makeup air supply 127 and inlet conduit 134. The dry air valve 144 may selectively allow, partially allow, or block, flow of dry makeup air from dry makeup air supply 127 to sterilization chamber 102 via inlet conduit 134.

A moist makeup air supply 117 may be configured to supply moist makeup air (e.g., air comprising more humidity than dry makeup air from dry makeup air supply 127) to sterilization chamber 102, via inlet conduit 134. A moist air valve 124 may be coupled to the fluid connection between moist makeup air supply 117 and inlet conduit 134. The moist air valve 124 may selectively allow, partially allow, or block, flow of moist makeup air from moist makeup air supply 117 to sterilization chamber 102 via inlet conduit 134.

Moist makeup air supply 117, for example, may be any supply of air (e.g., room air, or compressed air) or other fluid external from the rest of sterilization system 100. In some embodiments, moist makeup air supply 117 may be a supply of “room air” surrounding sterilization system 100, which may have gone through an indoor filtration system. In some embodiments, moist makeup air supply 117 may include more water vapor than “room air.” In some embodiments, moist makeup air supply 117 may be a supply of filtered outdoor air.

A VHP injector 132, fluidly connected to inlet conduit 134, is configured to inject VHP to sterilization chamber 102 via inlet conduit 134. A VHP injector valve 128 is coupled to the fluid connection between VHP injector 132 and inlet conduit 134, and selectively allows, partially allows, or blocks flow of VHP from VHP injector 132 to sterilization chamber 102 via inlet conduit 134.

VHP injector 132 may include a supply of VHP, or VHP and vaporized water, and may be configured to inject VHP or a combination of VHP and vaporized water into sterilization chamber 102 via, e.g., inlet conduit 134. VHP injector 132 may be configured to inject vapor into sterilization chamber 102 (or inlet conduit 134) at an adjustable concentration.

Depending on the position of dry air valve 144, moist air valve 124, and VHP injector valve 128: dry makeup air from dry makeup air supply 127, moist makeup air from moist makeup air supply 117, VHP from VHP injector 132, or a combination thereof, may enter sterilization chamber 102 via inlet conduit 134. For example, during pre-conditioning, moist air valve 124 may be in a position such that moist makeup air from moist makeup air supply 117 is blocked from entering inlet conduit 134, VHP injector valve 128 may be in a position such that VHP from VHP injector 132 is blocked from entering inlet conduit 134, and dry air valve 144 may be in a position such that dry makeup air flows from dry makeup air supply 127 to sterilization chamber 102, via inlet conduit 134. In such a configuration, only dry makeup air flows to the sterilization chamber 102, allowing for faster pre-conditioning.

In another configuration, moist air valve 124 may be in a position such that moist makeup air flows from moist makeup air supply 117 to sterilization chamber 102 (i.e., via inlet conduit 134), VHP injector valve 128 may be in a position such that VHP flows from VHP injector 132 to sterilization chamber 102 (i.e., via inlet conduit 134), and dry air valve 144 may be in a position such that dry makeup air from dry makeup air supply 127 is blocked from entering inlet conduit 134. In such a configuration, moist makeup air may function as a binding media to carry VHP into sterilization chamber. Dry makeup air or a combination of dry makeup air and moist makeup air may also be used as binding media. Moist makeup air may be more effective as binding media than dry makeup air. Humidity (e.g., water) from the moist makeup air used as binding media may be removed from sterilization chamber 102 (e.g., via condenser 147) after VHP has been introduced.

An auxiliary dry air supply 130 fluidly connected to inlet conduit 135 may be configured to supply dry air to sterilization chamber 102 via inlet conduit 135. An auxiliary supply valve 126 is coupled to the fluid connection between auxiliary dry air supply 130 and inlet conduit 135, and is configured to selectively allow, partially allow, or block flow of dry air from auxiliary dry air supply 130 to sterilization chamber 102 via inlet conduit 135.

Dry makeup air supply 127 and auxiliary dry air supply 130 may have the same composition or different compositions. Either or both dry air supplies 127, 130 may be a supply of air having a relatively low humidity, such that it may be used to dry sterilization chamber 102 (e.g., a portion of sterilization chamber 102) and/or one or more of blower exit conduit 108, vacuum conduit 112, vacuum exhaust conduit 114, blower circulation conduit 118, and inlet conduit. For example, in some embodiments, air in either or both dry air supplies 127, 130 may include a dew point of, e.g., −10 degrees Celsius or less, −40 degrees Celsius or less, or anywhere between −10 degrees Celsius and −40 degrees Celsius. In some embodiments, either or both dry air supplies 127, 130 may be a supply of hygienic dry air, such as air that has been sterilized or otherwise filtered to at least 0.2 microns. In some embodiments, either or both dry air supplies 127, 130 may be a sealed supply of air. In some embodiments, either or both dry air supplies 127, 130 may be a supply of compressed air.

Sterilization system 100 may be configured to run sterilization cycles within sterilization chamber 102 at a variety of temperatures and pressures, and for a variety of time durations and/or time intervals. In some embodiments, the temperature(s), pressure(s), and time interval(s) at which sterilization system 100 may run sterilization cycles may be selectively and individually modified and customized. Moreover, temperature(s), pressure(s), and time intervals(s) may be adjusted during sterilization cycles, e.g., to effect improved distribution, migration, and/or removal of sterilants.

Sterilization system 100 may be configured to control the environment in the interior of sterilization chamber 102, including temperature, pressure, humidity, atmosphere, intake of fluids, and exit of fluids. Mechanisms for controlling temperature include: temperature modulation of input fluid streams and/or recirculating fluid streams, temperature modulation of portions of the sterilization chamber itself, and temperature modulation of other components of the system 100 (e.g., intake conduit 134, blower exit conduit 108, vacuum pump 110, temperature control jacket 104, blower circulation conduit 118, blower 106, recirculation valve 119, moist makeup air supply 117, dry makeup air supply 127, VHP injector 132, moist air valve 124, dry air valve 144, VHP injector valve 128, distribution manifolds 107*a*, 107*b*). Sterilization chamber 102 (e.g., a portion of sterilization chamber 102, such as, upper interior 101 or lower interior 103) may include, or be fluidly connected to one or more pistons 150 or diaphragm that may be actuated, inflated, deflated, or otherwise altered, to modulate the pressure of sterilization chamber 102 without introduction or removal of matter. The one or more pistons 150 or diaphragms may be configured to create pressure waves or generate low frequency pulses. These pressure waves and pulses may be used to affect (e.g., promote) condensation of sterilant on a surface of the load.

Further, sterilization system 100 may include any suitable number and location of sensors configured to sense, e.g., temperature, pressure, flow, chemical concentration, or other parameters throughout sterilization system 100, including in sterilization chamber 102, temperature control jacket 104, blower 106, vacuum pump 110, and/or any of conduits 108, 112, 114, 118, and 134. Such sensors may be configured to transmit sensed data to, e.g., controller 140 and/or a human-machine interface.

Sterilization chamber 102 may be a sealable chamber defining an interior, including upper interior 101 and lower interior 103. Sterilization chamber 102 may be openable into an open configuration, such that one or more items, e.g., products 105, may be placed inside as a part of a load for sterilization, and may be removed subsequent to sterilization. In some embodiments, sterilization chamber 102 may have an operating orientation, e.g., such that upper interior 101 is located above lower interior 103, and such that matter may fall (e.g., under the forces of gravity) from the vicinity of upper interior 101 towards lower interior 103. Sterilization chamber 102 may have one or more delivery apparatus to which one or more of inlet conduit 134 and inlet conduit 135 may be connected. As depicted in FIG. 1, for example, distribution manifolds 107*a*, 107*b* are two such delivery apparatuses. Distribution manifolds 107*a*, 107*b* may be configured to disperse gas, vapor, or liquid into sterilization chamber 102 in a given configuration, such as a stream or an even spray across sterilization chamber 102. For example, distribution manifold 107*a* may distribute gas, vapor, or liquid across upper interior 101 and distribution manifold 107*b* may distribute gas, vapor, or liquid across lower interior 103. Inlet 109 is another such delivery apparatus. Inlet 109 may also be configured to disperse gas, vapor, or liquid into sterilization chamber 102 in a given configuration, such as a stream, or an even spray across upper interior 101, or another portion of sterilization chamber 102.

In some embodiments, a distribution manifold (e.g., distribution manifold 107*a*) may be configured to disperse gas, vapor, or liquid into sterilization chamber 102 in one configuration, such as an even spray, and inlet 109 may be configured to disperse gas or vapor into sterilization chamber 102 in a different configuration, such as in a stream. In some embodiments, there may be no inlet 109, and both inlet conduits 134 and 135 may be connected to one or more distribution manifolds 107*a*, 107*b*.

Temperature control jacket 104 may be any material surrounding sterilization chamber 102, that is configured or effective to afford temperature control to the environment inside sterilization chamber 102. In some embodiments, for example, temperature control jacket 104 may be a water jacket surrounding sterilization chamber 102. In such embodiments, a temperature and/or a flow of water or other liquid through temperature control jacket 104 may be controlled by, e.g. controller 140.

Products 105 may be any item or items in a load suitable for sterilization using sterilization system 100. In some embodiments, products 105 may be medical products in primary packaging, secondary packaging, or both. In some embodiments, products 105 may be medical products having moving parts or parts otherwise sensitive to deep vacuum environments, such as environments having pressure of less than about 100 millibars. In some embodiments, products 105 may be, e.g., containers filled with a volume of formulated drug substance. For example, products 105 may be vials or PFS. In some embodiments, products 105 may include or may be covered by semi-permeable packaging, such as a semi-permeable membrane, through which vapor or gas may pass. In further embodiments, products 105 may be or include medical products sensitive to high temperatures, e.g., above 30° C. Such medical products may include, for example, formulated drug substances or other compositions that may be sensitive to high temperatures, such as proteins (e.g., antibodies or enzymes), fragments thereof, any antigen-binding molecules, nucleic acids, blood, blood components, vaccines, allergenics, gene therapy medicaments, tissues, other biologics, etc. For example, products 105 may be packaged PFS containing a formulated drug substance that includes an antibody or an adeno-associated virus (AAV). In some embodiments, products 105 may include drug products including a large molecule, e.g., a molecular weight of 30 kDA or greater. In some embodiments, products 105 may include ingredients such as, e.g., aflibercept, alirocumab, abicipar pegol, bevacizumab, brolucizumab, conbercept, dupilumab, evolocumab, tocilizumab, certolizumab, abatacept, rituximab, infliximab, ranibizumab, sarilumab, adalimumab, anakinra, trastuzumab, pegfilgrastim, interferon beta-la, insulin glargine [rDNA origin], epoetin alpha, darbepoetin, filigrastim, golimumab, etanercept, antigen-binding fragments of any of the above, or combinations of such binding domains, such as a bispecific antibody to VEGF or angiopoietin-2, among others.

In some embodiments, products 105 may include therapeutic products for ophthalmic diseases, including for the treatment of patients with Neovascular (Wet) Age-related Macular Degeneration (AMD), Macular Edema following Retinal Vein Occlusion (RVO), Diabetic Macular Edema (DME), and Diabetic Retinopathy (DR). In particular, large molecule and small molecule antagonists of VEGF and/or ANG-2, such as aflibercept, ranibizumab, bevacizumab, conbercept, OPT-302, RTH258 (brolocizumab), abicipar pegol (a pegylated designed ankyrin repeating protein (DARPin)), RG7716, or fragments thereof and in any concentration may be include in products 105. In some embodiments, products 105 may be products for cosmetic applications or medical dermatology, such as treatment or diagnosis of allergic responses.

Blower 106 may be, for example, a blower having the capacity to forcibly draw vapor and gas from lower interior 103 of sterilization chamber 102 through blower exit conduit 108, optionally through condenser 147, and to reintroduce said vapor and gas back to upper interior 101 of sterilization chamber 102 via inlet conduit 134 (or, alternatively, to draw such vapor and gas through exhaust valve 120 and catalytic converter 121, to exhaust 116). In some embodiments, blower 106 may be external to sterilization chamber 102, as shown in FIG. 1. In other embodiments, blower 106 may be disposed within sterilization chamber 102. In some embodiments, blower 106 may be configured to draw vapor and gas from lower interior 103 of sterilization chamber 102 and reintroduce said vapor and gas back to upper interior 101 with sufficient force to create a flow of vapor and gas from upper interior 101 to lower interior 103 of sterilization chamber 102. This flow may be termed a "turbulent flow." In some embodiments, the force with which blower 106 may operate may be adjustable (via, for example, controller 140), such that a more turbulent (e.g., more forceful), or less turbulent, flow of vapor and gas within sterilization chamber 102 may be generated. In some embodiments, blower 106 may be configured to generate a stronger force to draw vapor and gas than, e.g., vacuum pump 110.

Vacuum pump 110 may be a vacuum pump having the capacity to draw gas from the interior (e.g., lower interior 103) of sterilization chamber 102, via vacuum conduit 112 and catalytic converter 115, and towards exhaust 116, thereby creating a vacuum within sterilization chamber 102 and/or a closed system containing sterilization chamber 102 and, e.g., blower 106. Vacuum pump 110 may be fluidly connected to exhaust 116 via, e.g., vacuum exhaust conduit 114. In some embodiments, exhausts from vacuum pump 110 and blower 106 may be separated instead of being combined into one.

In some embodiments, vacuum-type functions may also or alternately be performed by, e.g., blower 106, which may selectively circulate vapor and gas out of and into sterilization chamber 102 or out of sterilization chamber 102, through exhaust valve 120, and towards exhaust 116. Exhaust valve 120 may be selectively opened or closed so as to permit or prevent flow of gas or vapor from blower circulation conduit 118 towards exhaust 116 or towards inlet conduit 134 for reintroduction into sterilization chamber 102. Exhaust valve 120 may be manually controlled, or may be controlled by, e.g., controller 140.

Catalytic converter 115, catalytic converter 121, or both may be, for example, any catalytic converters known in the art suitable for converting toxic gaseous or vaporized fluids circulated within sterilization system 100, e.g., during a sterilization cycle, to less toxic gases or vapors. For example, catalytic converters 115, 121 may be configured to convert VHP into water vapor, oxygen, and/or other non-toxic fluids.

A controller 140 is connected to one or more other components of sterilization system 100, such as sterilization chamber 102, temperature control jacket 104, blower 106, VHP injector 132, moist makeup air supply 117, dry makeup air supply 127, auxiliary dry air supply 130, vacuum pump 110, piston 150, catalytic converters 115, 121, condenser 147, distribution manifolds 107, **107*b*, conduits 112, 108, 118, 134, 135, valves 113, 119, 120, 124, 126, 144, and/or any other components of sterilization system 100. Some or all aspects of sterilization system 100 may be controllable by, e.g., controller 140. For example, controller 140 may be in communication with one or more valves 113, 119, 120, 124, 126, 144, and may be configured to control, adjust, and/or monitor the position of the one or more valves 113, 119, 120, 124, 126, 144. In addition or alternatively, the one or more valves 113, 119, 120, 124, 126, 144** may be manually operated.

Controller 140 may be, for example, an analog or digital controller configured to alter aspects of the environment of sterilization chamber 102 such as an internal temperature or pressure of sterilization chamber 102 and/or one or more of blower 106, vacuum pump 110, air supply 117, dry air supply 130, VHP injector 132, exhaust 116, one or more of valves 113, 119, 120, 124, 126, and 128, one or more of catalytic converters 115, 121, one or more of conduits 108, 112, 114, 116, 118, and 134, and any and/or other aspects of sterilization system 100. In some embodiments, sterilization system 100 may be controllable by multiple controllers 140. In other embodiments, sterilization system may only have one controller 140. In some embodiments, controller 140 may be a digital controller, such as a programmable logic controller.

In some embodiments, controller 140 may be pre-programmed to execute one or more sterilization, aeration, drying, and/or cleaning cycles using sterilization system 100. In some embodiments, sterilization system 100 may be controllable by a controller having one or more human machine interface ("HMI") elements, which may be configured to allow a user to input or alter desired parameters for a cycle, which may be executable by a controller on or operably coupled to sterilization system 100. Thus, in some embodiments, HMI elements may be used to program a customized cycle for execution by sterilization system 100. For example, in some embodiments, sterilization system 100 may be controllable by a controller connected to, e.g., a computer, tablet, or handheld device having a display. Such a display may include, for example, options to select or alter a desired temperature, pressure, time, amount of VHP intake, amount of dry air, compressed air, or room air intake, etc., for one or more steps of a cycle.

Figure 1B:
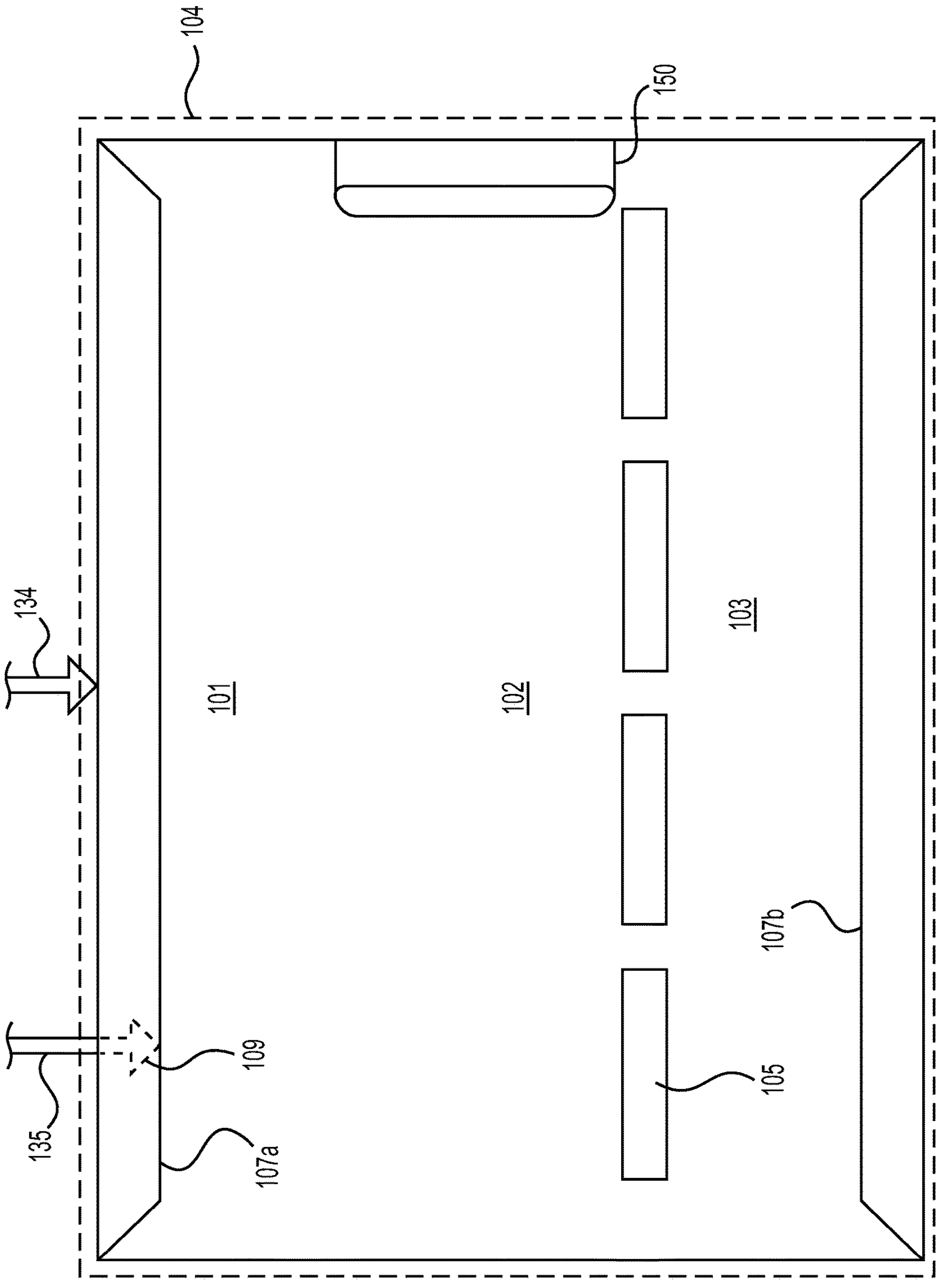
FIG. 1B is a schematic drawing showing an expanded view of a portion of the system shown in FIG. 1A.

FIG. 1B depicts an expanded view of sterilization chamber 102. Sterilization chamber 102 may serve as an exemplary environment in which many aspects of the present disclosure may be applicable. It is to be understood, however, that sterilization chamber 102 is merely exemplary, and that aspects of the present disclosure may be applicable in many other environments.

Variations in temperature, pressure, humidity, and air/fluid flow may characterize different portions of sterilization chamber 102. For example, temperature control jacket 104 may be configured to control a temperature within sterilization chamber 102, but may have a more immediate effect on a periphery of sterilization chamber 102 than on a more central part of its interior. As has been described previously, temperature control jacket 104 may more immediately affect the temperature of products 105 (i.e., a load) closer to the periphery of sterilization chamber 102 than to the middle of sterilization chamber 102, causing products 105 closer to the periphery to be, e.g., warmer than products 105 in the middle.

As another example, distribution manifolds **107*a*, 107*b* and/or inlet 109 may have surface temperatures differing from an average interior temperature of sterilization chamber 102 (e.g., they may be cooler or warmer than an average interior temperature of sterilization chamber 102). Additionally, during operation of system 100, distribution manifolds 107*a*, 107*b*, inlet 109, a diaphragm (not pictured), and/or piston 150 may create localized areas of relatively higher pressure around themselves as they inject fluid into sterilization chamber 102 or create a pressure wave. This may cause greater condensation of fluids in areas closer to the source of the pressure wave as compared to areas farther away. For example, sterilant dispersed from one of the distribution manifolds 107*a*, 107*b* may be more likely to condense on products 105 located closer to distribution manifold 107*a*, 107*b* than products 105** that are farther away.

As has been described previously, products 105 may include one or more semi-permeable membranes through which vapor or gas may flow, such as a cover on packaging for a medical device or drug product. Semi-permeable membranes may, in some cases, not allow liquid to pass through them. In some embodiments, sterilization of areas on both sides of the semi-permeable membrane is desired.

FIGS. 2A, 2B, 3A, 3B, 4, and 5 depict flow diagrams of phases and steps in methods for sterilization according to the present disclosure. As will be recognized by one of ordinary skill in the art, some phases and/or steps may be omitted, combined, and/or performed out of order while remaining consistent with the present disclosure. In some embodiments, the phases and/or steps may be performed using, e.g., sterilization system 100 or a variation of sterilization system 100. Additionally or alternatively, the phases and/or steps may be applicable in other environments in which manipulation of vaporized sterilant is desirable. It will be recognized that the customizable and controllable aspects of sterilization system 100 may be used in order to carry out phases and steps described below. For example, in some embodiments, controller 140 may be employed to direct, adjust, or modify temperature, pressure, timings, etc. in a series of sterilization steps, setpoints, and phases performable by sterilization system 100. Additionally, although the phases and steps described below are recited in relation to sterilization system 100, one of ordinary skill in the art will understand that these phases and steps may be performed by another sterilization system, or another system having the capacity to carry out the steps.

Figure 2A:
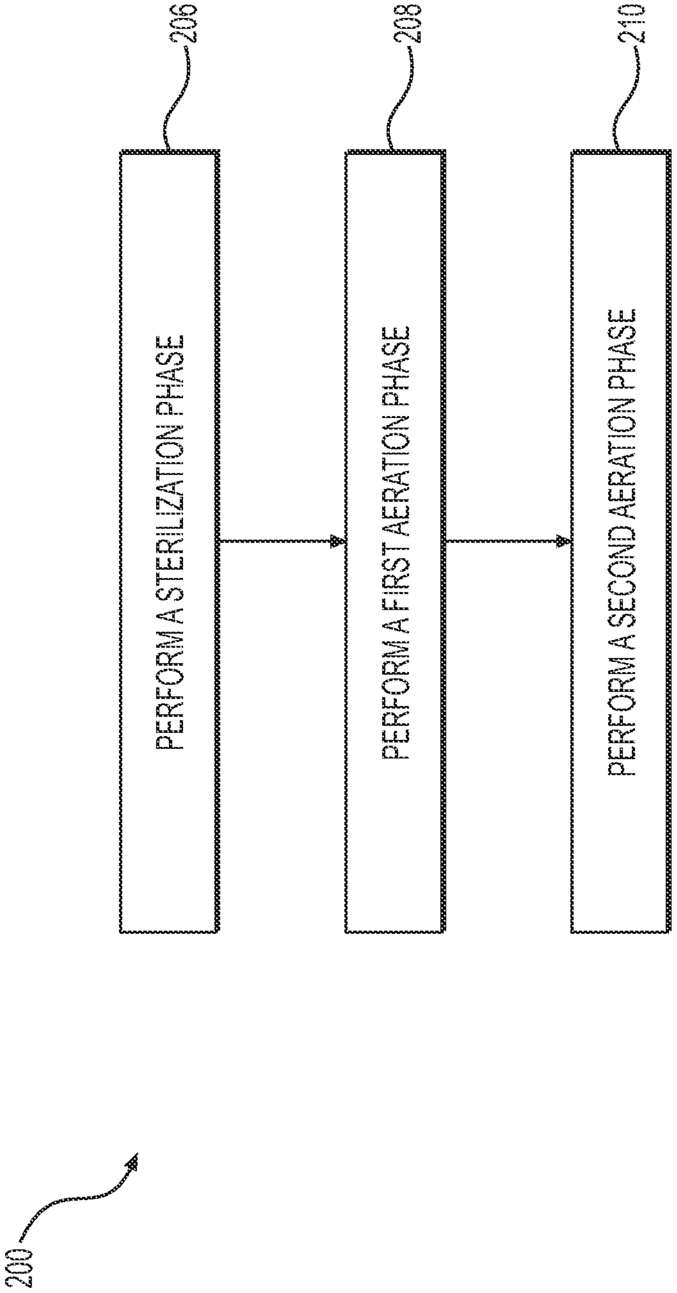
FIGS. 2A and 2B are flow diagrams of steps in an exemplary method of sterilizing medical products using vaporized chemicals.

FIG. 2A depicts a flow diagram of a series of steps in a method 200 for sterilization in a sterilization system, such as sterilization system 100. According to step 206, a sterilization phase may be performed. According to step 208, a first aeration phase may be performed. According to step 210, a second aeration phase may be performed.

Prior to performance of the steps of method 200, a sterilization load, such as products 105, may be placed within a sterilization chamber, such as sterilization chamber 102, of a sterilization system, such as sterilization system 100. A closed-system sterilization environment—including, for example, sterilization chamber 102, blower exit conduit 108, blower 106, blower circulation conduit 118, inlet conduit 134, condenser 147, and any elements connecting these components—may then be sealed. In some cases, a leak test may be performed on the closed-system sterilization environment. The leak test may include, for example, creating a vacuum through the closed system. The vacuum may be created by, e.g., expelling gas and vapor from the closed system using vacuum pump 110. During the leak test, blower 106 may be in operation, so as to circulate any remaining air through the closed system and create a homogenous environment. The leak test may be performed in this manner in part to verify that a suitable vacuum may be held within the closed system.

In some embodiments, the sterilization system (e.g., sterilization system 100) may be preconditioned. Preconditioning may include, for example, increasing the temperature of the closed system to temperatures intended to be maintained during a sterilization phase (e.g., between about 25° C. and about 50° C.). In some embodiments, preconditioning may be performed for longer than is performed in standard chemical sterilization procedures, which may allow more time for any temperature differences between the environment in the closed system (including, e.g., areas of a sterilization chamber such as sterilization chamber 102) to decrease. Alternately or additionally, preconditioning may include, for example, pairing a temperature of a temperature control jacket (e.g., temperature control jacket 104) with a temperature of an inlet, such as distribution manifold 107*a*, distribution manifold 107*b*, and/or inlet 109, prior to or for the duration of method 200. By "pairing" the temperature of the temperature control jacket with the temperature of an inlet, it is meant that the temperature control jacket is programmed to maintain the same or a similar temperature as a surface temperature of an inlet inside the sterilization chamber. This may be advantageous because inlets (e.g., distribution manifolds 107*a*, 107*b* and/or inlet 109) may generally be cooler than other parts of the sterilization chamber, due to the temperature of, e.g., sterilant, compressed air, or other fluid traveling through them. Additionally, as the temperature control jacket warms the sterilization chamber 102, the periphery of the chamber (e.g., a portion of the sterilization chamber 102 closest to the temperature control jacket) may be warmer than the middle of the sterilization chamber (e.g., farthest from the temperature control jacket). Thus, pairing the temperature control jacket with the temperature of an inlet may reduce temperature differences across the sterilization chamber. In some embodiments, the temperature control jacket may be paired by, e.g., setting the temperature control jacket to a known temperature of an inlet during a sterilization cycle. In some embodiments, the temperature control jacket may be paired by, e.g., experimentally determining a temperature of an inlet during one or more sterilization cycles and setting the temperature control jacket to that temperature. In other embodiments, a digital thermometer may be disposed in contact with or near an inlet (e.g., a distribution manifold 107*a*, 107*b*, or inlet 109), which may relay temperature information to a controller (e.g., controller 140). For example one or more thermometers or temperature sensors may transmit temperature information to the controller 140 when prompted, periodically, continuously, or dynamically (e.g., periodically during the sterilization cycle, based on monitored conditions of the chamber).

The controller 140 may, in turn, set the temperature control jacket to the temperature sensed at or near the inlet (e.g., distribution manifolds 107*a*, 107*b*, or inlet 109). As surface temperatures of distribution manifolds 107*a*, 107*b*, and inlet 109 may in general be cooler than an average internal temperature of sterilization chamber 102, pairing the temperature of the temperature control jacket 104 with the temperatures of an inlet (e.g., distribution manifolds 107*a*, 107*b*, or inlet 109) may rectify some differences in temperature existing throughout the sterilization chamber, which may, in turn, aid in distribution of sterilant throughout the sterilization chamber.

It is also contemplated that, in some embodiments, maintaining a temperature differential between the sterilization load and the surrounding closed system, creating "cold spots" [via] may have advantages. For example, controlled condensation of vaporized sterilizing chemical (e.g., VHP) on "cold spots" of the load may concentrate the sterilizing chemical on the load and lead to more efficient diffusion of the chemical into the load, thus decreasing the overall amount of sterilizing chemical needed in the sterilization chamber 102 to achieve effective sterilization. In such embodiments, it may be advantageous to reduce a time for preconditioning, or to eliminate preconditioning entirely.

According to step 206, a sterilization phase may be performed. The sterilization phase may include, for example, initiating circulation of fluid through the sterilization system, achieving a vacuum level, injecting vaporized chemical into the sterilization chamber, maintaining a post-injection hold, injecting gas into the sterilization chamber to transition to a shallower vacuum, and maintaining a post-transition hold. The sterilization phase according to step 206 may be repeated multiple times, using similar or different vacuum levels, volumes of vaporized chemicals, and/or hold times. Sterilization phases according to step 206 are depicted in further detail in FIGS. 3A and 3B.

According to step 208, a first aeration phase may be performed. The first aeration phase may include, for example, achieving a vacuum level, holding the vacuum level, breaking the vacuum level, and aerating and exhausting the system. The first aeration phase may be performed multiple times. A first aeration phase according to step 208 is depicted in further detail in FIG. 4.

According to step 210, a second aeration phase may be performed. The second aeration phase may include, for example, achieving a vacuum level, holding the vacuum level, and breaking the vacuum level. The second aeration phase may be performed multiple times. A second aeration phase according to step 210 is depicted in further detail in FIG. 5.

Step 208 and/or step 210 may be performed multiple times. Additionally, while in some embodiments, step 208 may be performed before step 210, in alternative embodiments, step 210 may be performed before step 208. In some embodiments, step 208 or step 210 may be eliminated entirely.

Figure 2B:
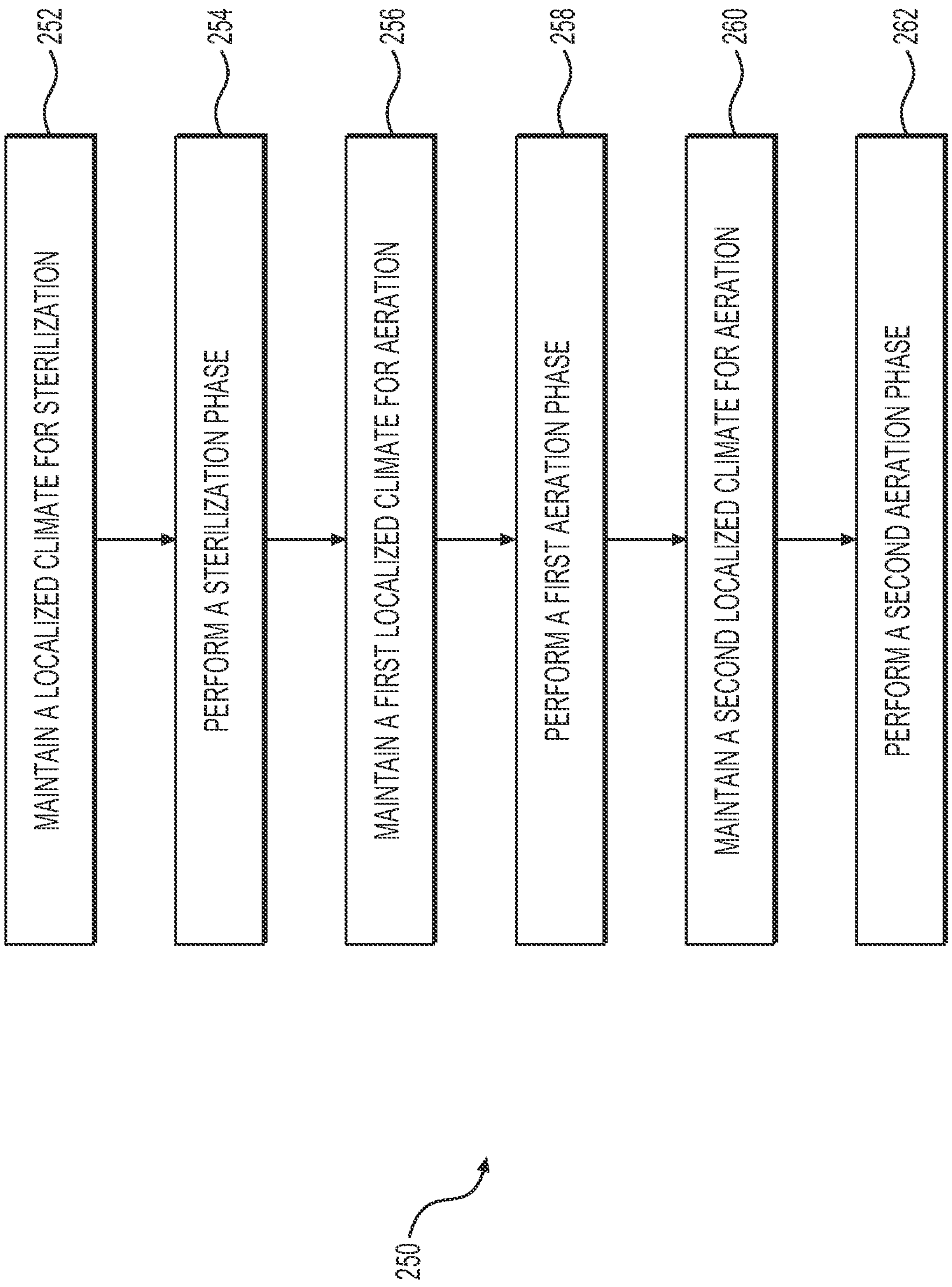

FIG. 2B depicts a flow diagram of a series of steps in a method 250 for sterilization in a sterilization system, such as sterilization system 100. According to step 252, a localized climate for sterilization may be maintained. According to step 254, a sterilization phase may be performed. According to step 256, a first localized climate for aeration may be maintained. According to step 258, a first aeration phase may be performed. According to step 260, a second localized climate for aeration may be maintained. According to step 262, a second aeration phase may be performed.

Prior to performance of the steps of method 250, a sterilization load may be placed within a sterilization chamber, which may be sealed, a leak test may be performed, and the sterilization system may be preconditioned, as described above with respect to method 200. Sterilization phase 254, first aeration phase 258, and second aeration phase 262 may be performed in any manner suitable for sterilization phase 206, first aeration phase 208, and second aeration phase 210, respectively. Step 258 and/or step 262 may be performed multiple times. Additionally, while in some embodiments, step 258 may be performed before step 262, in alternative embodiments, step 258 may be performed before step 262. In some embodiments, step 258 or step 262 may be eliminated entirely.

Each of steps 254, 258 and 262 may be preceded by the step of maintaining a localized climate. Maintaining a localized climate may generally refer to ensuring that one or more areas within a sterilization system (e.g., sterilization system 100) exhibit conditions (e.g., temperature, pressure, water vapor concentration, sterilant concentration, etc.) suitable for upcoming steps in a sterilization method. Maintenance of consistent or targeted localized climates may aid in robust sterilization and aeration efficacy. Localized climates may attract or repel sterilant to one or more specific localities within a system. If controlled, such localized climates may assist in achieving a desired level of sterilization. For example, inlets, and/or carts supporting the sterilization load may be heated to prevent condensation of sterilant. The load itself (e.g., packaging) may be kept at a temperature cooler than the carts to attract VHP or promote adhesion and condensation. Larger loads may also be used to reduce peak load temperature.

Furthermore, maintaining localized climates may aid in distributing sterilant to, or removing sterilant from, more difficult localities within a sterilization system, thus reducing the amount of "overkill" needed to sterilize or aerate those localities. Attracting sterilant to a locality that has previously proven to struggle passing sterilization standards (e.g., biological indicator metrics) may normalize sterilization of that zone without the need to add more sterilant. Similarly, removing sterilant from a locality that has previously been difficult to aerate may reduce overall aeration and drying times in the methods herein.

As depicted in FIG. 2B, a localized climate for sterilization may be maintained, e.g., step 252. This may include attracting sterilant to an area within a system using, e.g., differences in temperature. In some embodiments, this may be accomplished by changing a temperature of one or more localities to reduce the temperature of localities to which sterilant should move. For example, the periphery of a sterilization chamber may be warmer than the middle of the chamber, due to heating elements located around the periphery of the chamber (e.g., temperature control jacket 104 of system 100). Maintaining a localized climate for sterilization at the periphery of a sterilization chamber may thus include decreasing the temperature of the periphery of the sterilization chamber by, e.g., decreasing a target temperature of a heating element (e.g., temperature control jacket 104). Maintenance of a localized climate for sterilization according to step 252 may continue throughout the performance of the sterilization phase, according to step 254.

A first localized climate for aeration may be maintained according to step 256, and a second localized climate for aeration may be maintained according to step 260. Each of the first localized climate for aeration and the second localized climate for aeration may include, e.g., raising a temperature of a locality within a sterilization system, reducing a humidity of a locality within a sterilization system, etc. Each of the first localized climate and the second localized climate may be maintained during the first aeration phase 258 and the second aeration phase 262, respectively.

Figure 3A:
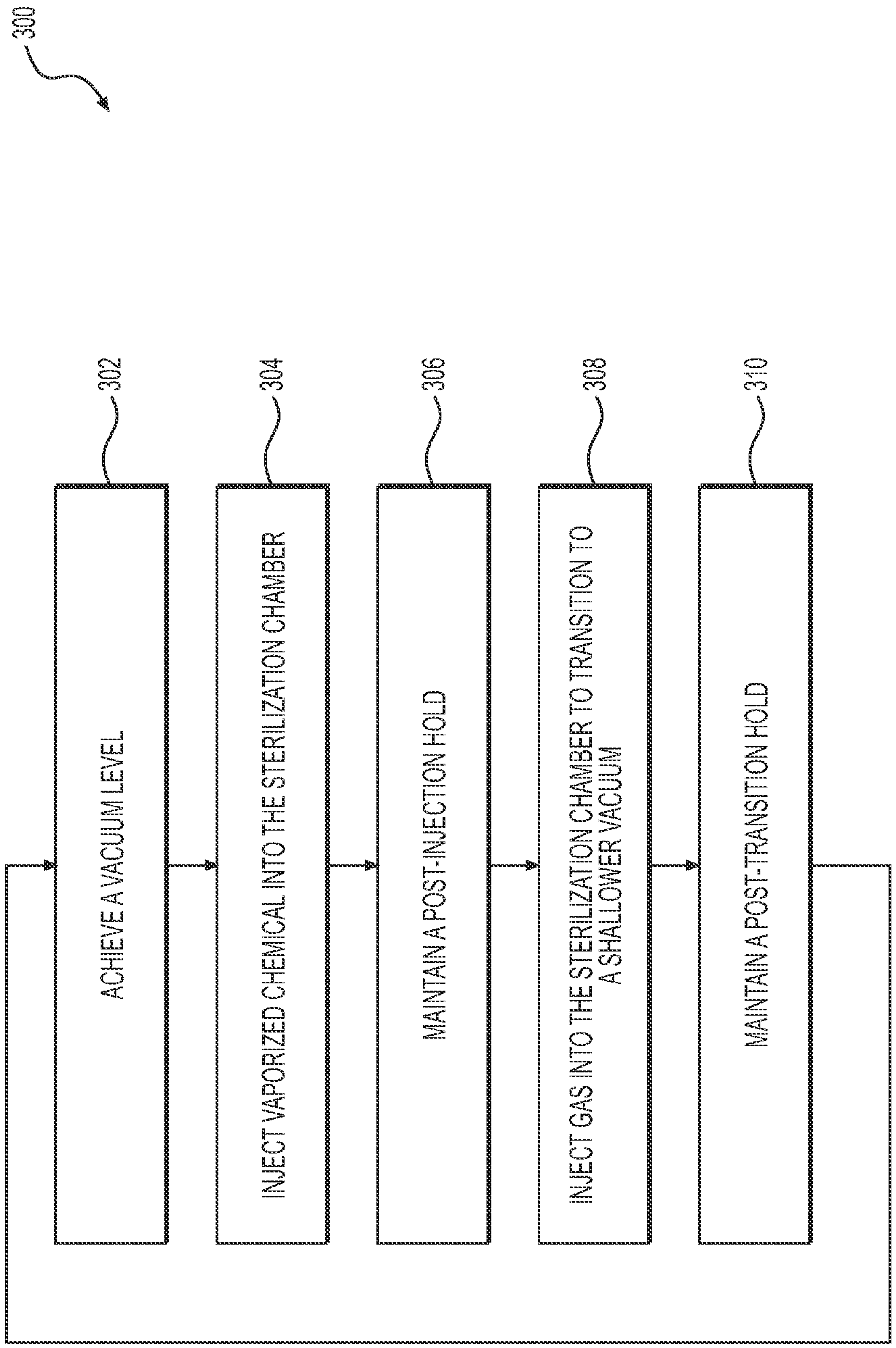
FIGS. 3A and 3B are flow diagrams of steps in an exemplary method of performing a sterilization phase.

FIG. 3A is a flow diagram of a sterilization phase 300, such as, for example, the sterilization phase described step 206 of sterilization method 200 or step 254 of method 250. Prior to sterilization phase 300, a sterilization load (e.g., products 105) may be introduced into sterilization chamber 102. According to step 302, a vacuum level may be achieved. According to step 304, vaporized chemical may be injected into the sterilization chamber. According to step 306, a post-injection hold may be maintained. According to step 308, gas may be injected into the sterilization chamber to transition to a shallower vacuum. According to step 310, a post-injection hold may be maintained. Sterilization phase 300 may be repeated multiple times, such as between 2 and 15 times, between 2 and 12 times, between 2 and 10 times, between 2 and 8 times, between 2 and 6 times, between 2 and 5 times, or between 2 and 4 times, such as twice, 3 times, 4 times, 5 times, 6 times, 7 times, or 8 times. A single iteration of a sterilization phase (e.g., sterilization phase 300) may be referred to as a "pulse."

As a part of sterilization phase 300, a turbulent flow may be initiated and maintained in sterilization system 100.

According to step 302, a vacuum level may be achieved within sterilization chamber 102 of sterilization system 100. The vacuum level may be, for example, between about 400 millibars and about 700 millibars, such as between about 450 millibars and about 650 millibars, or between about 450 millibars and about 550 millibars. For example, the vacuum may be about 450 millibars, about 500 millibars, about 550 millibars, or about 600 millibars. This vacuum may promote a higher concentration of sterilizing chemical on the sterilization load, extending the amount of time at which the closed system is kept at a deeper vacuum increases exposure of the sterilization load to the sterilizing chemical.

According to step 304, vaporized chemical may be injected into the sterilization chamber. In some embodiments, the vaporized chemical may include VHP. In some embodiments, the vaporized sterilization chemical may be a vaporized aqueous hydrogen peroxide solution, having a concentration of, for example, between about 5% and about 75% hydrogen peroxide by weight. In some embodiments, the vaporized chemical may be a vaporized aqueous hydrogen peroxide solution having a concentration of, for example, between about 10% and about 65% hydrogen peroxide by weight, between about 15% and about 60% hydrogen peroxide by weight, between about 30% and about 60% hydrogen peroxide by weight, or between about 45% and about 60% hydrogen peroxide by weight. In some embodiments, the vaporized chemical may be a vaporized aqueous hydrogen peroxide having a concentration of about 35% hydrogen peroxide (and 65% water) by weight. In further embodiments, the vaporized chemical may be a vaporized aqueous hydrogen peroxide having a concentration of about 59% hydrogen peroxide (and 41% water) by weight.

In some embodiments, an injected supply of VHP may be, for example, between about 50 g and about 700 g of aqueous VHP. For example, the injected supply of VHP may be between about 50 g and about 600 g, between about 100 g and about 600 g, between about 300 g and about 550 g, or between about 450 g and about 550 g. For example, the injected supply of VHP may be about 100 g, about 200 g, about 300 g, about 400 g, about 450 g, about 475 g, about 500 g, about 525 g, about 550 g, about 600 g, or about 650 g. In some embodiments, an injected supply of VHP may be quantified based on the volume or amount of load to be sterilized inside sterilization chamber 102. For example, if a number of drug products, such as pre-filled syringes, are to be sterilized in sterilization chamber 102, an injected supply of VHP may be between about 0.01 and about 0.15 grams of VHP per unit of the drug product inside sterilization chamber 102, such as between about 0.01 and about 0.10 grams of VHP, such as about 0.015 grams, 0.02 grams, 0.025 grams, 0.03 grams, 0.04 grams, 0.05 grams, 0.06 grams, 0.07 grams, 0.08 grams, 0.09 grams, 0.1 grams, or 0.11 grams per drug product. In other embodiments, an injected supply of VHP may be quantified based on the volume of the sterilization environment, such as the interior of sterilization chamber 102. For example, an injected supply of VHP may be between about 0.2 and 3.0 grams per cubic foot of volume in a sterilization chamber. For example, an injected supply of VHP may be between about 0.2 and about 2.0 grams per cubic foot, such as about 0.25 grams, about 0.50 grams, about 0.75 grams, about 1.0 gram, about 1.2 grams, about 1.4 grams, about 1.5 grams, about 1.6 grams, about 1.8 grams, or about 2.0 grams per cubic foot. In some embodiments, an injected supply of VHP may be based on a quantity of VHP injected into the sterilization chamber in a previous iteration of sterilization phase 300. For example, a first quantity of VHP may be injected into the sterilization chamber in a first iteration of sterilization phase 300. A second quantity of VHP, less than the first quantity, may be injected into the sterilization chamber in a second iteration of sterilization phase 300, based on the quantity injected in the first iteration. A third quantity of VHP, less than the second quantity, may be injected into the sterilization chamber in a third iteration of sterilization phase 300, based on the combined quantities injected in the first and second iterations.

In some embodiments, an injected supply of VHP may be based on a combination of the quantity of VHP in the sterilization chamber already, and a desired increase in pressure caused by the injection of additional VHP into the sterilization chamber. A desired increase in pressure caused by the injection of VHP into the sterilization chamber may be inversely related to an amount of hydrogen peroxide already present in the sterilization chamber. Advantageously, lower increases in pressure as the amount of VHP in the sterilization chamber increases may help in reducing unwanted condensation of VHP, which may be caused by excessive rises in pressure. Unwanted condensation of VHP may result in reduced sterilization efficiency and reduced aeration efficacy.

According to step 306, a post-injection hold may be maintained. During the post-injection hold, turbulent flow is maintained through the closed system including sterilization chamber 102 and blower 106. No fluids are added or removed from the closed system in which the turbulent flow is maintained. The time for which a post-injection hold is maintained (or the "post-injection hold time") may be selected so as to allow the vaporized sterilization chemical adequate time to contact the load, without allowing the vaporized sterilization chemical to condense. In some embodiments, the post-injection hold time may be between about 2 minutes and about 20 minutes. In some embodiments, the post-injection hold time may be at least about 5 minutes, at least about 10 minutes, or at least about 15 minutes. In some embodiments, the post-injection hold time may be between about 5 minutes and about 20 minutes, between about 8 minutes and about 20 minutes, between about 10 minutes and about 20 minutes, or between about 10 minutes and about 15 minutes. In such a manner, the need for adding excess VHP into the system to ensure its contact with the sterilization load may be avoided.

According to step 308, gas may be injected into the sterilization chamber to transition to a shallower vacuum (i.e., a higher pressure) in the sterilization chamber. The gas may be any suitable gas that can break or lessen the vacuum in sterilization chamber 102. In some embodiments, the gas may be a dry gas, such as a gas containing nitrogen (e.g., commercially available supplies of only nitrogen or primarily nitrogen), or air having a dew point of, for example, −10° C. or colder. The use of a dry gas may be selected to allow for ample air exchange and reduction in humidity within a sterilization chamber, to further avoid unnecessary condensation. In some embodiments, gas may be injected from dry air supply 130. The gas may be injected in a volume to achieve a pressure between about 500 millibars and about 1100 millibars, such as between about 550 millibars and about 1000 millibars, between about 600 millibars and about 1000 millibars, between about 700 millibars and about 900 millibars, or between about 750 millibars and about 850 millibars. For example, the second post-injection pressure may be about 700 millibars, about 750 millibars, about 800 millibars, about 850 millibars, or about 900 millibars. In cases where a sterilization load includes semi-permeable membranes through which it is desired that sterilant pass, the increase in pressure caused by step 308 may serve to help migrate the sterilant through such semi-permeable membranes.

According to step 310, a post-transition hold may be maintained. During the post-transition hold, the pressure achieved during step 308 may be maintained for, for example, at least about 5 minutes, at least about 10 minutes, or at least about 15 minutes. In some embodiments, the second post-injection pressure may be maintained for between about 5 minutes and about 20 minutes, between about 8 minutes and about 20 minutes, between about 10 minutes and about 20 minutes, or between about 10 minutes and about 15 minutes.

In some embodiments, the number of times that sterilization phase 300 may be repeated (e.g., the number of pulses) may be inversely proportional to the time that the post-injection hold is maintained in each repetition. For example, if the time that the post-injection hold is maintained is short (e.g., 10 minutes), then steps 210 through 216 may be repeated a greater number of times. In some embodiments, the post-injection hold is maintained for a longer period of time (e.g., 15-20 minutes), to increase the time during which the sterilization load is exposed to the sterilizing chemical in each repetition of sterilization phase 300. In further embodiments, the number of times that sterilization phase 300 may be repeated may depend on a total desired amount of VHP for the sterilization process. In some embodiments, for example, injection of a total amount of at least 200 g of VHP may be desired. For example, in some embodiments, injection of a total amount of at least 250 g may be desired. In some embodiments, injection of a total amount of between about 200 g and about 700 g of VHP may be desired. In some embodiments, the number of times that the sterilization phase 300 may be repeated may depend on a combination of factors to ensure thorough permeation of VHP through a sterilization load, and to ensure enough contact time between the hydrogen peroxide and the load to permit sterilization.

Figure 3B:
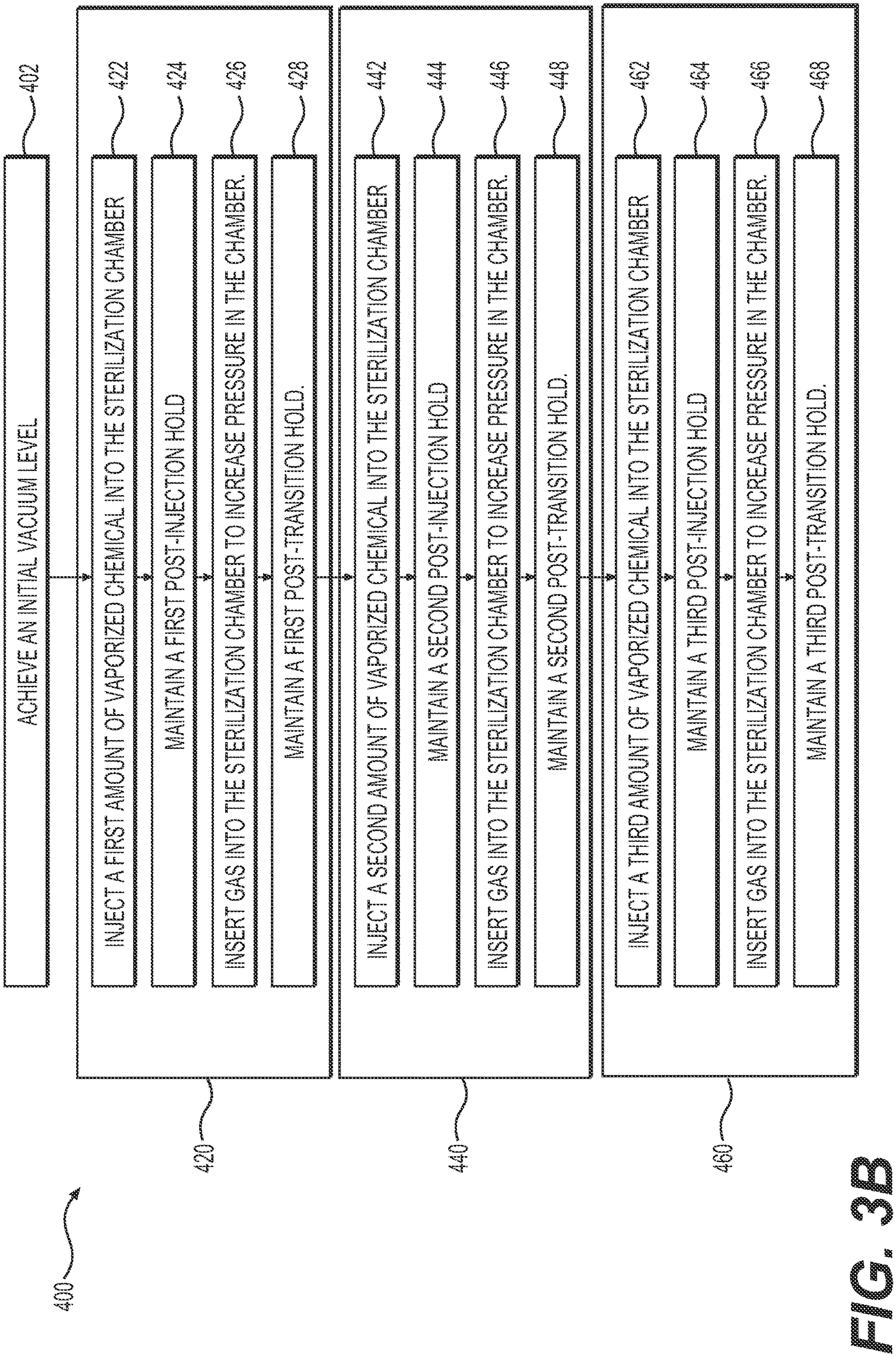

FIG. 3B is a flow diagram of a sterilization phase 400 that includes multiple sterilization pulses 420, 440, 460, each of which may include the injection of different amounts of VHP into the sterilization chamber, may include different hold times and pressure changes, and may be performed once or multiple times. According to step 402, an initial vacuum level may be achieved. During pulse 420, a first amount of vaporized chemical may be injected into the sterilization chamber (step 422), a first post-injection hold may be maintained (step 424), gas may be injected into the sterilization chamber to increase pressure in the chamber (step 426), and a first post-transition hold may be maintained (step 428). During pulse 440, a second amount of vaporized chemical may be injected into the sterilization chamber (step 422), a second post-injection hold may be maintained (step 424), gas may be injected into the sterilization chamber to increase pressure in the chamber (step 426), and a second post-transition hold may be maintained (step 428). During pulse 460, a third amount of vaporized chemical may be injected into the sterilization chamber (step 422), a third post-injection hold may be maintained (step 424), gas may be injected into the sterilization chamber to increase pressure in the chamber (step 426), and a third post-transition hold may be maintained (step 428).

As described previously, the pressure increase caused by each sterilization pulse (pulses 420, 440, 460) may be reflective of the sterilization chamber's existing concentration of sterilant and water (e.g., hydrogen peroxide). When the existing concentration is lower (or zero), such as prior to pulse 420, greater increases in pressure may be used to maximize the speed at which sterilant is introduced to the load. Thus, a first amount of vaporized chemical introduced according to step 422 may be greater than a second or third amount of vaporized chemical introduced according to steps 442 or 462.

In cases in which a semi-permeable membrane is desired to be traversed by sterilant (e.g., a Tyvek membrane covering a medical device or product), a delay in transport of some sterilants (e.g., hydrogen peroxide) across the membrane has been observed. Additionally, in some sterilization cycles, hydrogen peroxide concentration in areas obstructed by a semi-permeable membrane has been observed to be generally lower than (or "dampened") in areas not obstructed by a semi-permeable membrane. Water does not exhibit such delayed transport or dampening. As a result, sterilant strength and efficacy (and particularly, hydrogen peroxide strength and efficacy) in areas obstructed by a semi-permeable membrane may be decreased. The third amount of vaporized chemical introduced according to step 462 may specifically aid in overcoming this transport delay and dampened sterilant concentration. The third amount of vaporized chemical may be less than the first amount of vaporized chemical introduced according to step 422 or the second amount of vaporized chemical introduced according to step 424, to avoid causing aggressive increases in pressure and over-condensation which may prevent migration of sterilant across semi-permeable membranes.

Given the principles described above, in some embodiments, the first amount of sterilant injected according to step 422 may be greater than the second amount of sterilant injected according to step 442, and the second amount of sterilant injected according to step 442 may be greater than the third amount of sterilant according to step 462. For example, the first amount of sterilant may be a bolus (e.g., a large amount) to establish a lethal concentration within the sterilization chamber, the second amount (e.g., a medium amount) may be chosen to maintain the concentration and satisfy hold time requirements, and the third amount (e.g., a small amount) may be chosen to overcome sterilant transport delay and damping across semi-permeable membranes.

For example, a large amount may include 15 grams of 35 wt. % $H_2O_2$ per cubic meter of sterilization chamber volume, a medium amount may include 7.5 grams of 35 wt. % $H_2O_2$ per cubic meter of sterilization chamber volume, and a small amount may be 0.5 grams of 35 wt. % $H_2O_2$ per cubic meter of sterilization chamber volume.

A time for each post-injection hold 424, 444, 464 may be dependent on a volume of vaporized sterilant within the sterilization chamber prior to the post-injection hold, as well as the pressure within the sterilization chamber prior to the post-injection hold. In some embodiments, each post-injection hold 424, 444, 464 may be shorter than the time required for condensation of vaporized sterilant within the sterilization chamber. This may allow for more sterilant to remain in vapor form when gas is injected into the sterilization chamber according to steps 426, 446, 466. For example, each post-injection hold 424, 444, 464 may have a duration of ten minutes or less, such as, for example, 8 minutes or less, 6 minutes or less, 4 minutes or less, 3 minutes or less, or less than 3 minutes.

The time for each post-transition hold 428, 448, 468 may be sufficient to expose surfaces within the sterilization chamber to the sterilant, to effectively sterilize such surfaces. For example, each post-transition hold 428, 448, 468 may have a duration of ten minutes or less, such as, for example, 8 minutes or less, 6 minutes or less, 4 minutes or less, 3 minutes or less, or less than 3 minutes. In some embodiments, a post-transition hold may cease after about half of the peak VHP concentration is reached.

As previously mentioned, each of pulses 420, 440, and 460 may be performed one time or multiple times. In some embodiments, pulse 420 may be performed once, and pulses

440 and 460 may each be performed multiple times. For example, pulse 420 may be repeated once or twice, pulse 440 may be repeated once or twice, and pulse 460 may be repeated 2-10 times. In some embodiments, either pulse 440 or pulse 460 may be eliminated from sterilization phase 400. For sterilization loads including more semi-permeable membranes or materials resistant to VHP saturation, more pulses 420 including a large bolus of sterilant may be used.

During a sterilization phase, such as, for example, sterilization phase 206, sterilization phase 254, sterilization phase 300, and/or sterilization phase 400, it may be beneficial to regulate the speed with which pressure changes are accomplished such that decreases in pressure are slower than increases in pressure. For example, steps 304, 308, 422, 426, 442, 446, 462, and 466, which include or result in raising pressure within a sterilization chamber (e.g., adding fluid, breaking vacuum, or via a diaphragm or piston 150 within sterilization chamber 102), may include increasing pressure within a sterilization chamber more quickly than pressure is decreased in steps 302 or 402, which include achieving a vacuum level. This may encourage permeation of sterilant throughout the sterilization chamber and the load, including portions of the load enclosed within a semi-permeable membrane.

Figure 4:
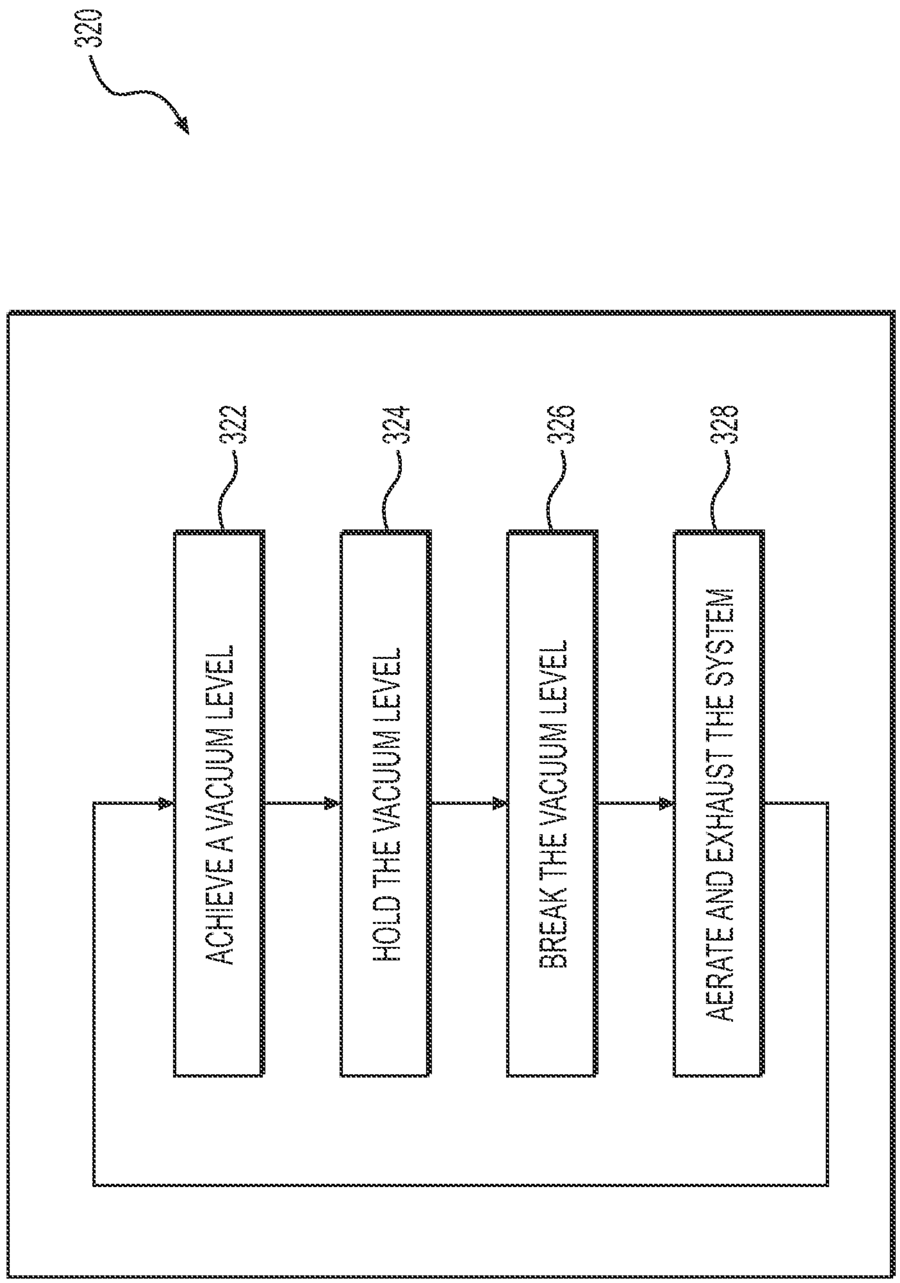
FIG. 4 is a flow diagram of steps in an exemplary method of performing an aeration phase.

FIG. 4 is a flow diagram of a first aeration phase 320 that may be performed as step 208 of sterilization method 200, after performing one or more repetitions of sterilization phase according to step 206. According to step 322, a vacuum level may be achieved. According to step 324, the vacuum level may be held. According to step 326, the vacuum level may be broken. According to step 328, the sterilization system (e.g., sterilization system 100) may be aerated and exhausted.

According to step 322, a vacuum level may be achieved in sterilization chamber 102, while also injecting dry gas into sterilization chamber 102 near upper interior 101 of sterilization chamber 102, such as via distribution manifold 107*a* or inlet 109 and/or near lower interior 103 of sterilization chamber 102 via distribution manifold 107*b*. Dry gas may assist in allowing for air exchange without promoting condensation of sterilant. The dry gas may include, for example, oxygen and/or nitrogen. The dry gas may have a dew point of, for example, −10° C. or lower. The dry gas may be injected from, e.g., auxiliary dry air supply 130 or dry makeup air supply 127. While dry gas is being injected into sterilization chamber 102, a vacuum may be pulled by, e.g., vacuum pump 110 via vacuum conduit 112, catalytic converter 115, and vacuum exhaust conduit 114. The vacuum may be pulled at a greater rate than the rate of injection of dry gas, such that a vacuum level is gradually achieved. The vacuum level may be, for example, between about 500 millibars and about 850 millibars, such as between about 500 millibars and about 800 millibars, between about 550 millibars and about 750 millibars, or between about 600 millibars and about 700 millibars. For example, the vacuum level may be 500 millibars, 550 millibars, 600 millibars, 650 millibars, or 700 millibars. Injection of the dry gas near upper interior 101 of sterilization chamber 102 while achieving a desired vacuum level reduces condensation of VHP and water vapor at upper interior 101 of the chamber, and promotes the movement of denser molecules in sterilization chamber towards the lower interior (e.g., lower interior 103) of sterilization chamber 102, and to some extent out of sterilization system 100 through vacuum exhaust conduit 114.

According to step 324, injection of dry gas may be stopped and the vacuum level may be held for, e.g., between about 1 minute and about 20 minutes, such as between about 2 min and about 20 min, between about 5 min and about 20 min, between about 5 min and about 15 min, or between about 5 min and about 10 min. For example, the vacuum level may be maintained for about 2, 5, 8, 10, or 15 minutes. Holding the vacuum level may continue to promote settling of denser molecules (e.g., sterilization chemical molecules) down towards the lower interior 103 of sterilization chamber 102, and away from the sterilization load.

According to step 326, the vacuum level may be broken by the addition of more dry gas near upper interior 101 of sterilization chamber 102, via, for example, distribution manifold 107*a* or inlet 109 or dry gas near lower interior 103 of sterilization chamber 102 via distribution manifold 107*b*. A volume of dry gas sufficient to achieve a higher pressure may be added. The higher pressure may be, for example, between 50 and 200 millibars higher than the vacuum level achieved in step 322. The addition of more dry gas may continue to force sterilization chemicals to settle to the lower interior 101 of sterilization chamber 102, thus moving them away from the sterilization load and positioning them for removal via vacuum conduit 112 or blower exit conduit 108.

According to step 328, the sterilization system (e.g., sterilization system 100) may be aerated and exhausted. During this step, blower 106 may be turned on while recirculation valve 119 is closed and exhaust valve 120 is opened, such that blower 106 pulls fluid from within sterilization chamber 102 and expels it through exhaust 116 via catalytic converter 121. Because blower exit conduit 108 is connected to sterilization chamber 102 at lower interior 103 of sterilization chamber 102, denser fluids that have settled to lower interior 103 (such as sterilizing chemicals) may be removed by this step. Air (e.g., from moist makeup air supply 117 or dry makeup air supply 127) may be concurrently allowed to vent into sterilization chamber 102, such that the pressure in sterilization chamber 102 returns to, or near, atmospheric pressure.

First aeration phase 320 may be repeated, for example, between 1 and 35 times, such as 2, 5, 10, 15, 17, 19, 22, 25, 27, 29, 30, 32, or 35 times. Repetition of first aeration phase 320 may ensure that the majority of sterilization chemical (e.g., VHP) is removed from sterilization system 100.

Figure 5:
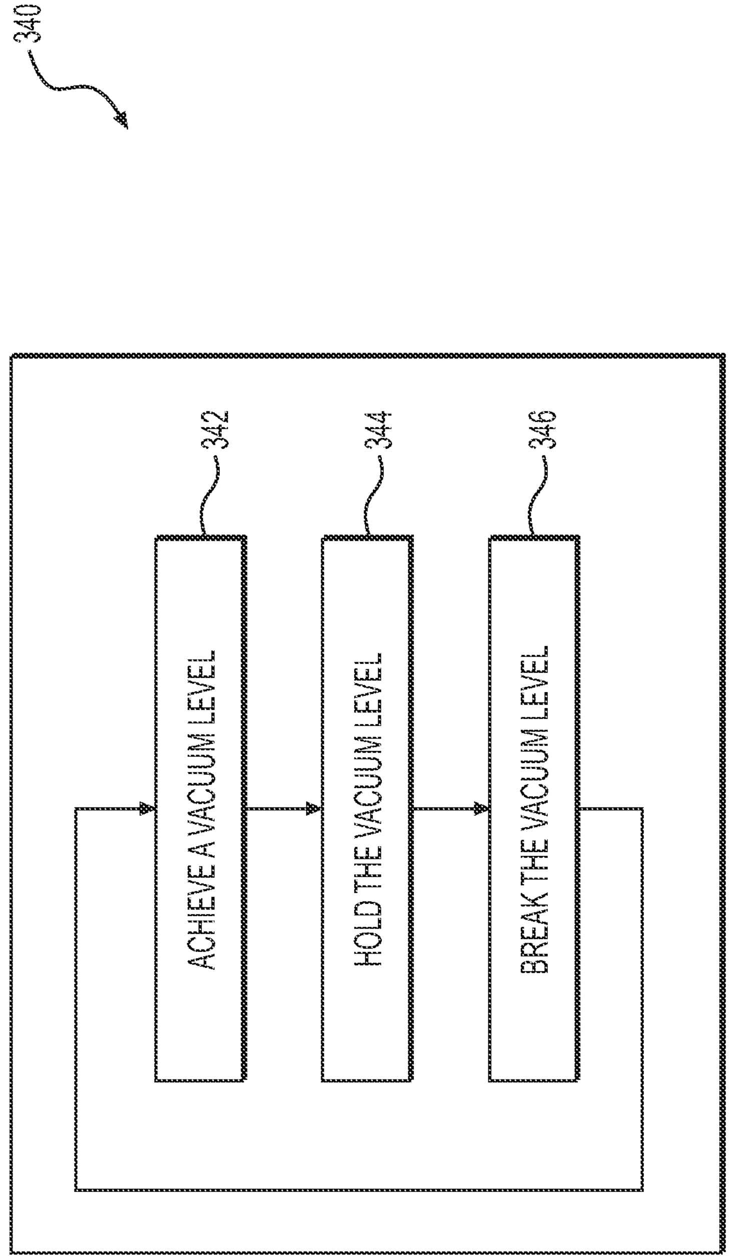
FIG. 5 is a flow diagram of steps in an exemplary method of performing another aeration phase.

FIG. 5 is a flow diagram of a second aeration phase 340 that may be performed as step 210 of sterilization method 200. According to step 342, a vacuum level may be achieved. According to step 344, a vacuum level may be held. According to step 346, the vacuum level may be broken.

According to step 342, a vacuum level may be achieved in sterilization chamber 102. Like with the first aeration phase, the vacuum level achieved in this phase may be, for example, between about 500 millibars and about 850 millibars, such as between about 500 millibars and about 800 millibars, between about 550 millibars and about 750 millibars, or between about 600 millibars and about 700 millibars. For example, the vacuum level may be 500 millibars, 550 millibars, 600 millibars, 650 millibars, or 700 millibars. Achieving a vacuum level may promote removing of moisture from sterilization chamber 102 and thus the sterilization load. Thus, the sterilization load may be dried.

According to step 344, the vacuum level may be held for, e.g., between about 1 minute and about 20 minutes, such as between about 2 min and about 20 min, between about 5 min and about 20 min, between about 5 min and about 15 min, or between about 5 min and about 10 min. For example, the vacuum level may be maintained for about 2, 5, 8, 10, or 15 minutes. Holding the vacuum level may continue to promote removal of moisture from sterilization chamber 102, and thus the sterilization load. Thus, the sterilization load may be further dried. In some embodiments, step 344 may be omitted.

According to step 346, the vacuum level in sterilization chamber 102 may be broken, or raised to a higher pressure, by the addition of dry gas from, e.g., auxiliary dry air supply 130 and/or dry makeup air supply 127.

Second aeration phase 340 may be repeated, for example, between 1 and 50 times, such as 2, 5, 10, 15, 20, 25, 30, 35, 38, 40, 42, 45, 47, 49, or 50 times. Repetition of second aeration phase 340 may ensure drying of sterilization chamber 102 and the sterilization load.

As has been previously described, second aeration phase 340 may be performed either before or after first aeration phase 320. First aeration phase 320 may ensure, for example, that the concentration of sterilizing chemical (e.g., VHP) in sterilization chamber 102 is relatively low, and second aeration phase 340 may ensure that the sterilization load is dried, and may also remove residual sterilizing chemical remaining in sterilization chamber 102 after first aeration phase 320. In cases where second aeration phase 340 is performed after first aeration phase 320, first aeration phase may ensure that the concentration of sterilization chemical (e.g., VHP) in sterilization chamber 102 is relatively low so that when sterilization chamber 102 and the sterilization load are dried in second aeration phase 340, there is little remaining need to remove residual sterilization chemical from the sterilization system 100.

In some embodiments, before performing first aeration phase 320 or second aeration phase 340, it may be desirable to achieve and/or maintain a localized climate suitable for aeration, as previously described with respect to steps 258 and 262 of sterilization method 250.

In some embodiments, before performing first aeration phase 320 or second aeration phase 340, pressure increases to atmospheric pressure may be avoided while the concentration of sterilant in the sterilization chamber is at or near a saturation point (e.g., after a sterilization phase is complete). Immediate increases to atmospheric pressure when a sterilization chamber is saturated or nearly saturated with sterilant may cause unnecessary condensation of sterilant and, subsequently, less efficacious aeration.

Prior to or during first aeration phase 320 or second aeration phase 340, repetitive inflection of pressure changes (e.g., evacuation and pressurization) may be advantageous to cause physical movement of packaging components, such as envelopes, covers, and membranes. Physical movement of parts of the load post-sterilization may aid in dislodging sterilant that has adhered to the load, thus promoting effective aeration.

Additionally, prior to or during first aeration phase 320 or second aeration phase 340, a temperature in the sterilization chamber or sterilization system may be increased. This may increase aeration efficacy.

Further, during an aeration phase (e.g., aeration phases 208, 210 258, 262, 320, 340), it may be beneficial to modulate the speed with which pressure changes are accomplished such that increases in pressure are slower than decreases in pressure. For example, steps 322, 328, and 342, which include achieving a vacuum level and aerating/exhausting a system, may include decreasing pressure within a sterilization chamber more quickly than pressure is increased in steps 326 and 346, which include breaking a vacuum level. This may encourage removal of sterilant from the sterilization chamber and the load.

In some embodiments, any or all of the above-described steps and phases may be executed automatically by a sterilization system (e.g., sterilization system 100) as directed by, e.g., controller 140, which may be programmed or otherwise configured in advance by e.g., a user. The methods of sterilization disclosed herein may be qualified as "limited overkill" sterilization methods, in that they may ensure sterilization of a load of, e.g., PFS while minimizing impact of the sterilization method on the product.

Multiple sterilization and aeration phases have been described herein. It is to be understood that characteristics, methods, or steps of any one sterilization phase may be applied to any other sterilization method described herein. Likewise, characteristics, methods, or steps of any one aeration phase described herein may be applied to any other aeration phase.

EXAMPLES

The following examples are intended to illustrate the present disclosure without being limiting in nature. It is understood that the present disclosure encompasses additional aspects and embodiments consistent with the foregoing description and following examples.

Example 1

In one example, a sterilization load including 24 biological indicators was loaded in a sterilization chamber, and a sterilization method was performed. The sterilization method included a leak test, a preconditioning phase, sterilization phase with one sterilization pulse, and two aeration phases. The exact parameters for the sterilization method are summarized in Table 1.

TABLE 1

| Phase | Parameter | Value |
|---|---|---|
| Leak Test | Vacuum Level | 500 mbar |
| Leak Test | Stabilization Time | 2 minutes |
| Leak Test | Leak Test Time | 5 minutes |
| Leak Test | Acceptable Total Leak | 13 mbar |
| Pre-conditioning | Pulse Quantity | 12 |
| Pre-conditioning | Vacuum Level | 500 mbar |
| Pre-conditioning | Vacuum Break Point | 700 mbar |
| Pre-conditioning | Jacket and Doors Temperature | 28° C. |
| Pre-conditioning | Vaporizer Temperature | 110° C. |
| Sterilization | Pulse Quantity | 1 |
| Sterilization | Vacuum Level | 500 mbar |
| Sterilization | $H_2O_2$ (59 wt. % solution) Injection Amount | 150 g/pulse |
| Sterilization | Injection Cycle Duration | 4500 milliseconds |
| Sterilization | Post-Injection Hold Time | 2 minutes |
| Sterilization | Transition Pressure Point | 940 mbar |
| Sterilization | Post-transition Hold Time | 7 minutes |
| First Aeration | Pulse Quantity | 10 |
| First Aeration | Vacuum Level | 500 mbar |
| First Aeration | Vacuum Break Point | 899 mbar |
| First Aeration | Exhaust Time | 0 minutes |
| First Aeration | Recirculate During Vacuum | Yes |
| Second Aeration | Pulse Quantity | 10 |
| Second Aeration | Vacuum Level | 500 |
| Second Aeration | Vacuum Break Point | 900 |
| Second Aeration | Exhaust Time | 10 |
| Second Aeration | Recirculate During Vacuum | No |

Figure 6:
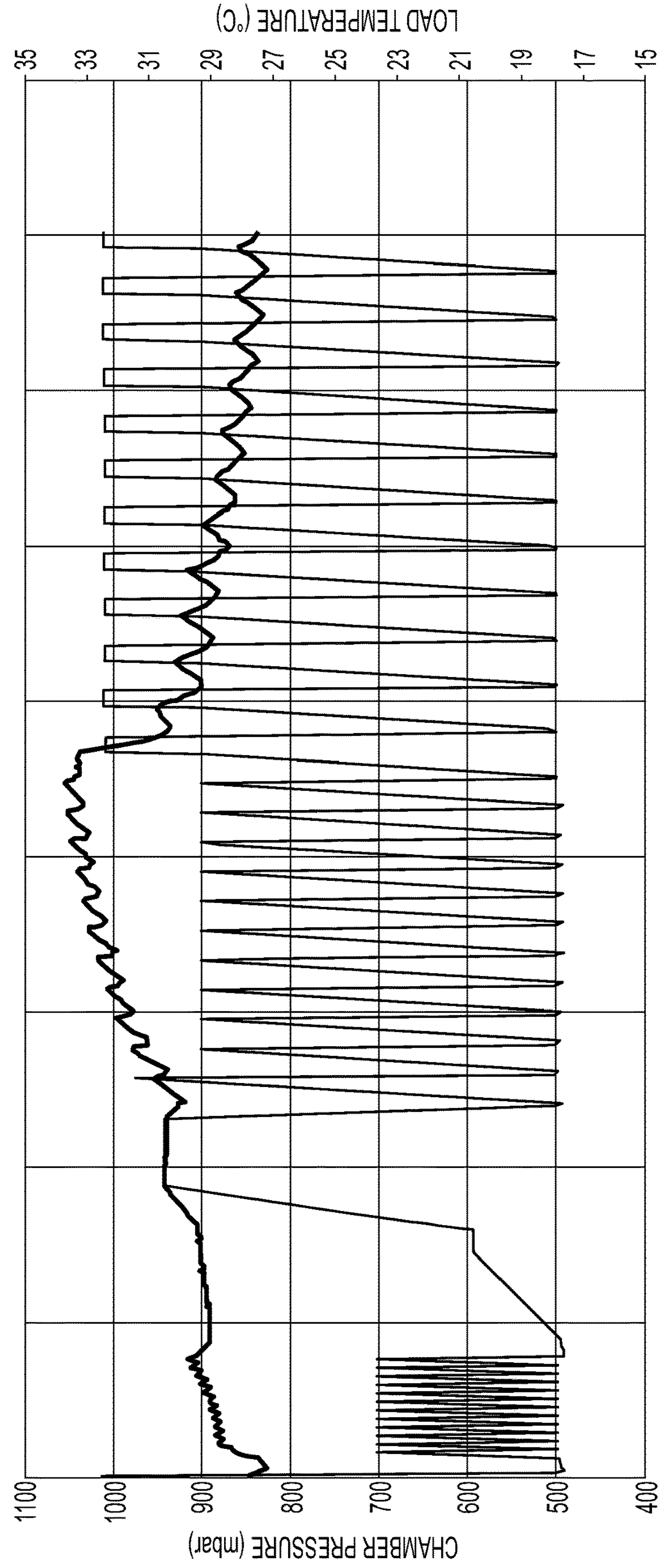
FIGS. 6, 7, 8A, 8B, 9A, and 9B show sterilization chamber pressure and load temperatures during exemplary sterilization methods.

The pressure of the sterilization chamber and the temperature of the load, during the sterilization method of Example 1, were measured and are shown in FIG. 6.

Example 2

In another example, a sterilization load including 20 biological indicators was loaded in a sterilization chamber, and a sterilization method was performed. The sterilization method included a leak test, a preconditioning phase, and a sterilization phase with two sterilization pulses. The exact parameters for the sterilization method are summarized in Table 2. The temperature of the sterilization load was monitored to ensure that it did not exceed 33° C.

TABLE 2

| Phase | Parameter | Value |
|---|---|---|
| Leak Test | Vacuum Level | 500 mbar |
| Leak Test | Stabilization Time | 2 minutes |
| Leak Test | Leak Test Time | 5 minutes |
| Leak Test | Acceptable Total Leak | 13 mbar |
| Pre-conditioning | Pulse Quantity | 12 |
| Pre-conditioning | Vacuum Level | 500 mbar |
| Pre-conditioning | Vacuum Break Point | 700 mbar |
| Pre-conditioning | Jacket and Doors Temperature | 28° C. |
| Pre-conditioning | Vaporizer Temperature | 110° C. |
| Sterilization | Pulse Quantity | 2 |
| Sterilization | Vacuum Level | 500 mbar |
| Sterilization | $H_2O_2$ (59 wt. % solution) Injection Amount | 150 g/pulse |
| Sterilization | Injection Cycle Duration | 4500 milliseconds |
| Sterilization | Post-Injection Hold Time | 2 minutes |
| Sterilization | Transition Pressure Point | 940 mbar |
| Sterilization | Post-transition Hold Time | 7 minutes |

Figure 7:
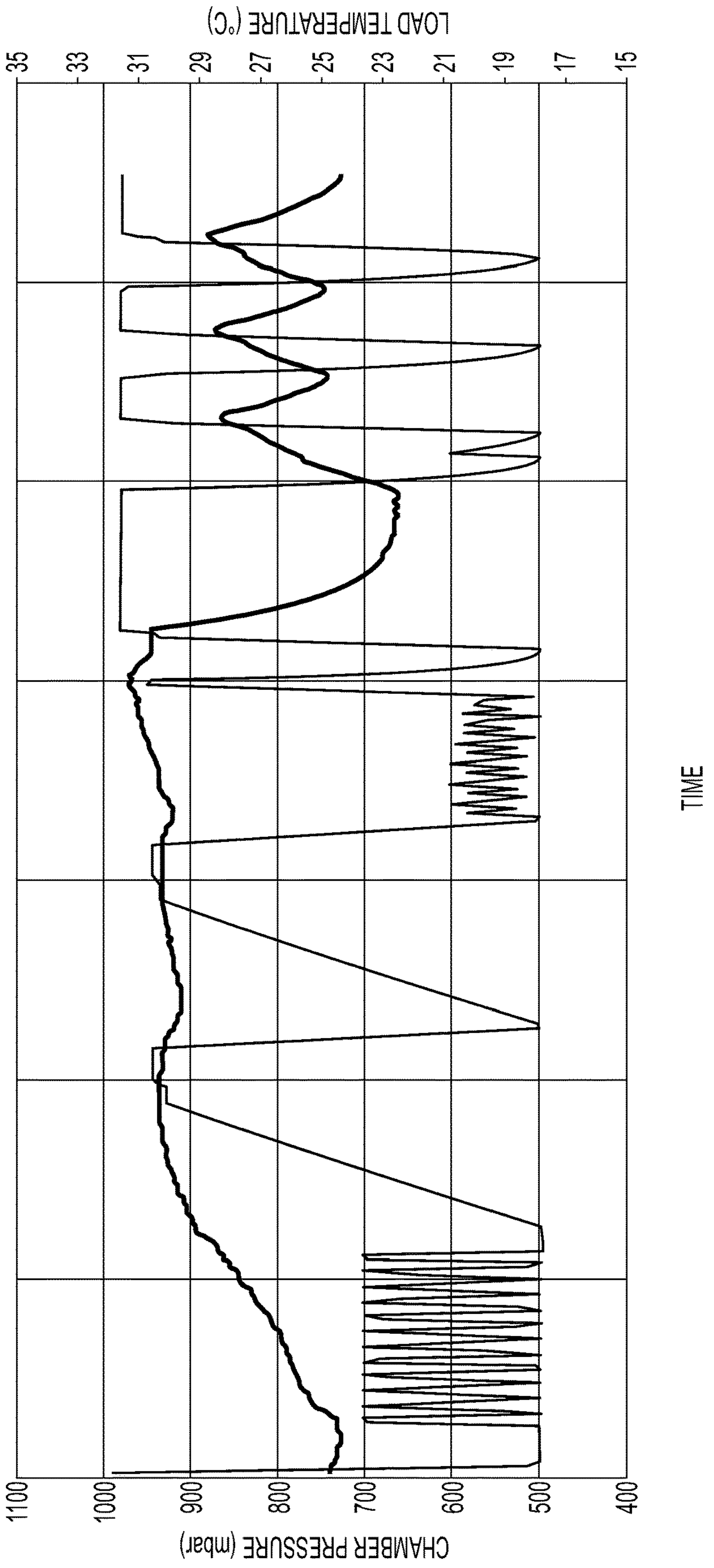

The pressure of the sterilization chamber and the temperature of the load, during the sterilization method of Example 2, were measured and are shown in FIG. 7.

Example 3

A sterilization load including 24 biological indicators was loaded in a sterilization chamber, and a sterilization method was performed. The sterilization method included a leak test, a preconditioning phase, sterilization phase with two sterilization pulses, and two aeration phases. The exact parameters for the sterilization method are summarized in Table 3.

TABLE 3

| Phase | Parameter | Value |
|---|---|---|
| Leak Test | Vacuum Level | 500 mbar |
| Leak Test | Stabilization Time | 2 minutes |
| Leak Test | Leak Test Time | 5 minutes |
| Leak Test | Acceptable Total Leak | 13 mbar |
| Pre-conditioning | Pulse Quantity | 12 |
| Pre-conditioning | Vacuum Level | 500 mbar |
| Pre-conditioning | Vacuum Break Point | 700 mbar |
| Pre-conditioning | Jacket and Doors Temperature | 28° C. |
| Pre-conditioning | Vaporizer Temperature | 110° C. |
| Sterilization | Pulse Quantity | 2 |
| Sterilization | Vacuum Level | 500 mbar |
| Sterilization | $H_2O_2$ (59 wt. % solution) Injection Amount | 150 g/pulse |
| Sterilization | Injection Cycle Duration | 4500 milliseconds |
| Sterilization | Post-Injection Hold Time | 2 minutes |
| Sterilization | Transition Pressure Point | 940 mbar |
| Sterilization | Post-transition Hold Time | 7 minutes |
| First Aeration | Pulse Quantity | 10 |
| First Aeration | Vacuum Level | 500 mbar |
| First Aeration | Vacuum Break Point | 899 mbar |
| First Aeration | Exhaust Time | 0 minutes |
| First Aeration | Recirculate During Vacuum | Yes |
| Second Aeration | Pulse Quantity | 10 |
| Second Aeration | Vacuum Level | 500 |
| Second Aeration | Vacuum Break Point | 900 |
| Second Aeration | Exhaust Time | 10 |
| Second Aeration | Recirculate During Vacuum | No |

Figure 8A:
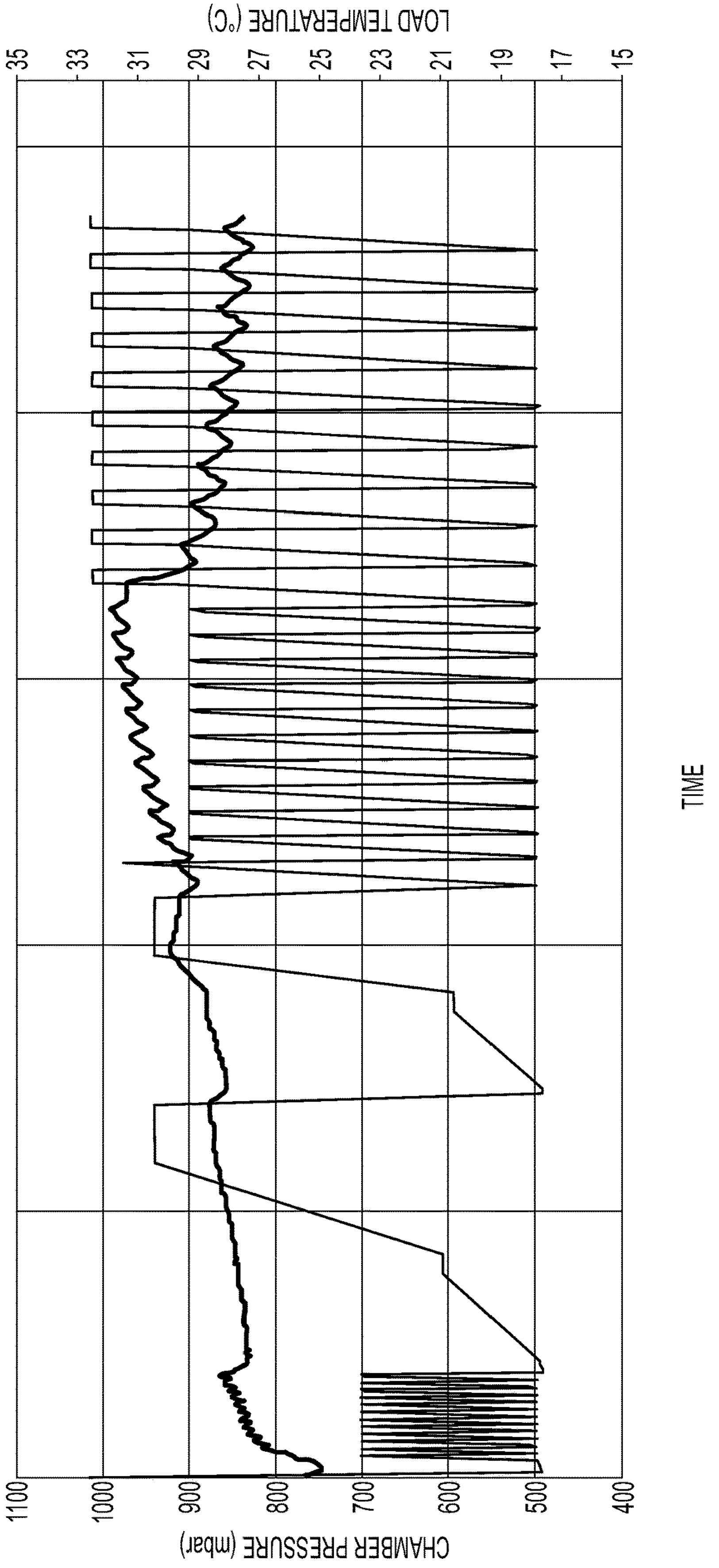

The pressure of the sterilization chamber and the temperature of the load, during the sterilization method of Example 3, were measured and are shown in FIG. 8A.

Example 4

A sterilization load including 24 biological indicators was loaded in a sterilization chamber, and a sterilization method was performed. The sterilization method included a leak test, a preconditioning phase, sterilization phase with two sterilization pulses, and two aeration phases. The exact parameters for the sterilization method are summarized in Table 4.

TABLE 4

| Phase | Parameter | Value |
|---|---|---|
| Leak Test | Vacuum Level | 500 mbar |
| Leak Test | Stabilization Time | 2 minutes |
| Leak Test | Leak Test Time | 5 minutes |
| Leak Test | Acceptable Total Leak | 13 mbar |
| Pre-conditioning | Pulse Quantity | 12 |
| Pre-conditioning | Vacuum Level | 500 mbar |
| Pre-conditioning | Vacuum Break Point | 700 mbar |
| Pre-conditioning | Jacket and Doors Temperature | 28° C. |
| Pre-conditioning | Vaporizer Temperature | 110° C. |
| Sterilization | Pulse Quantity | 2 |
| Sterilization | Vacuum Level | 500 mbar |
| Sterilization | $H_2O_2$ (59 wt. % solution) Injection Amount | 150 g/pulse |
| Sterilization | Injection Cycle Duration | 4500 milliseconds |
| Sterilization | Post-Injection Hold Time | 2 minutes |
| Sterilization | Transition Pressure Point | 940 mbar |
| Sterilization | Post-transition Hold Time | 7 minutes |
| First Aeration | Pulse Quantity | 10 |
| First Aeration | Vacuum Level | 500 mbar |
| First Aeration | Vacuum Break Point | 899 mbar |
| First Aeration | Exhaust Time | 0 minutes |
| First Aeration | Recirculate During Vacuum | Yes |
| Second Aeration | Pulse Quantity | 12 |
| Second Aeration | Vacuum Level | 500 |
| Second Aeration | Vacuum Break Point | 900 |
| Second Aeration | Exhaust Time | 10 |
| Second Aeration | Recirculate During Vacuum | No |

Figure 8B:
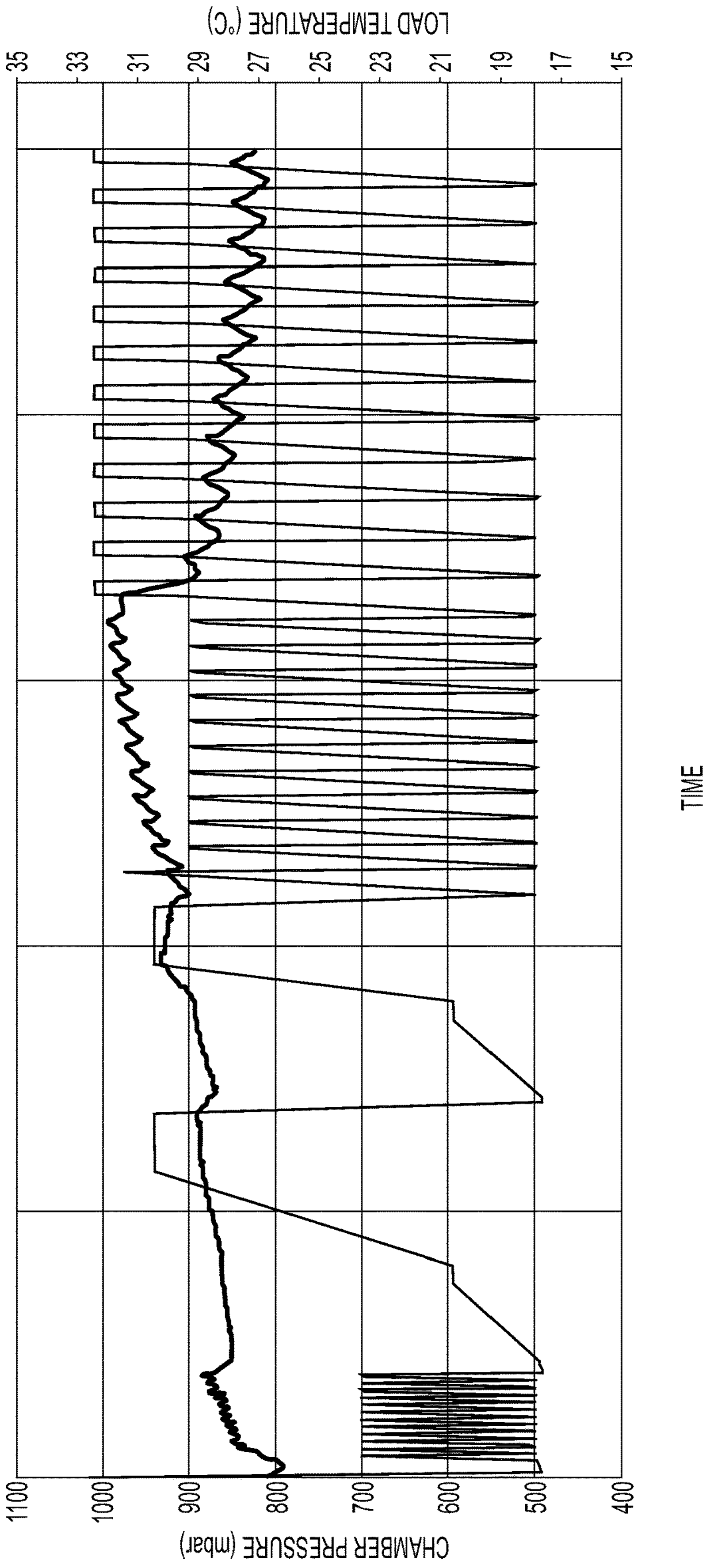

The pressure of the sterilization chamber and the temperature of the load, during the sterilization method of Example 4, were measured and are shown in FIG. 8B.

Example 5

A sterilization load including 24 biological indicators was loaded in a sterilization chamber, and a sterilization method was performed. The sterilization method included a leak test, a preconditioning phase, sterilization phase with three sterilization pulses, and two aeration phases. The exact parameters for the sterilization method are summarized in Table 5.

TABLE 5

| Phase | Parameter | Value |
|---|---|---|
| Leak Test | Vacuum Level | 500 mbar |
| Leak Test | Stabilization Time | 2 minutes |
| Leak Test | Leak Test Time | 5 minutes |
| Leak Test | Acceptable Total Leak | 13 mbar |
| Pre-conditioning | Pulse Quantity | 12 |
| Pre-conditioning | Vacuum Level | 500 mbar |
| Pre-conditioning | Vacuum Break Point | 700 mbar |
| Pre-conditioning | Jacket and Doors Temperature | 28° C. |
| Pre-conditioning | Vaporizer Temperature | 110° C. |

TABLE 5-continued

| Phase | Parameter | Value |
|---|---|---|
| Sterilization | Pulse Quantity | 3 |
| Sterilization | Vacuum Level | 500 mbar |
| Sterilization | $H_2O_2$ (59 wt. % solution) Injection Amount | 150 g/pulse |
| Sterilization | Injection Cycle Duration | 4500 milliseconds |
| Sterilization | Post-Injection Hold Time | 2 minutes |
| Sterilization | Transition Pressure Point | 940 mbar |
| Sterilization | Post-transition Hold Time | 7 minutes |
| First Aeration | Pulse Quantity | 10 |
| First Aeration | Vacuum Level | 500 mbar |
| First Aeration | Vacuum Break Point | 899 mbar |
| First Aeration | Exhaust Time | 0 minutes |
| First Aeration | Recirculate During Vacuum | Yes |
| Second Aeration | Pulse Quantity | 9 |
| Second Aeration | Vacuum Level | 500 |
| Second Aeration | Vacuum Break Point | 900 |
| Second Aeration | Exhaust Time | 10 |
| Second Aeration | Recirculate During Vacuum | No |

Figure 9A:
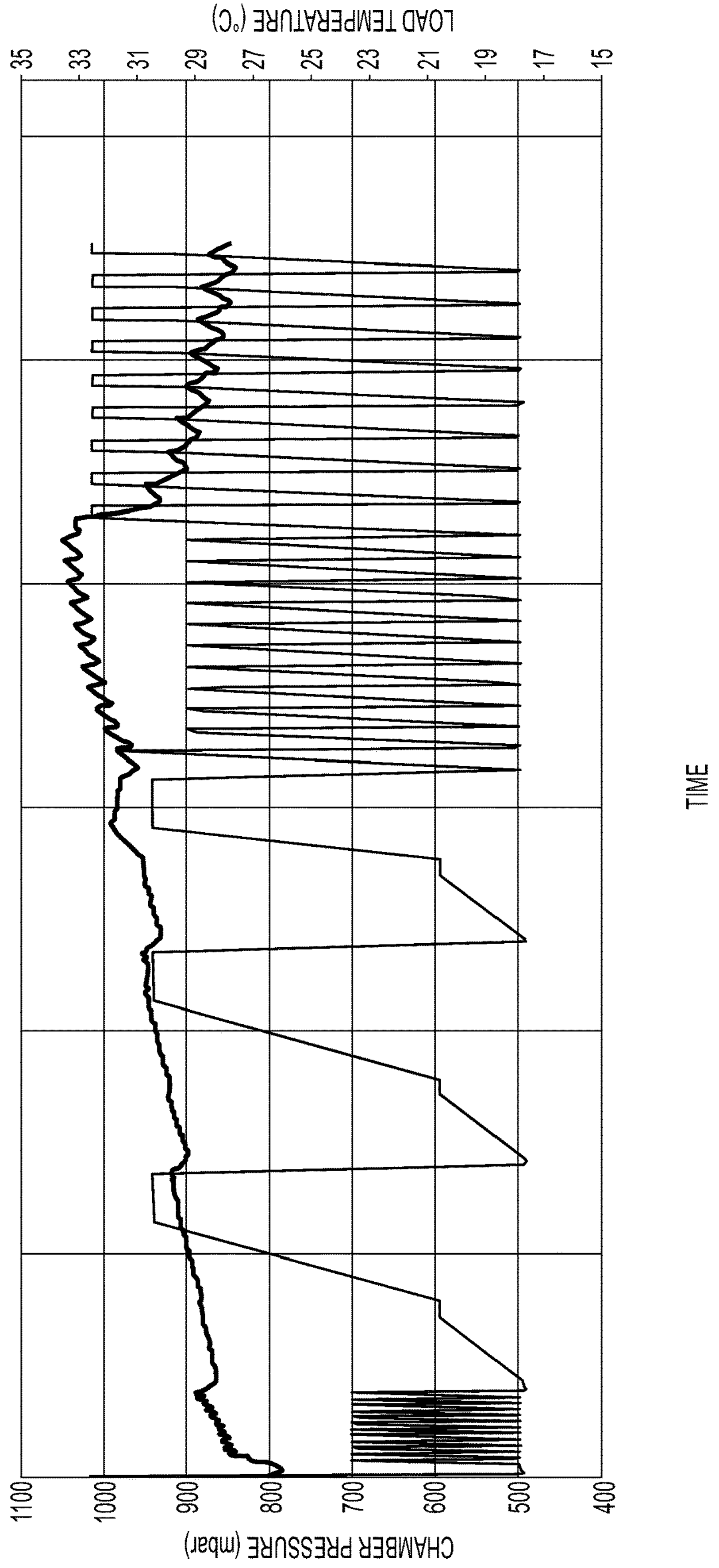

The pressure of the sterilization chamber and the temperature of the load, during the sterilization method of Example 5, were measured and are shown in FIG. 9A.

Example 6

A sterilization load including 24 biological indicators was loaded in a sterilization chamber, and a sterilization method was performed. The sterilization method included a leak test, a preconditioning phase, sterilization phase with three sterilization pulses, and two aeration phases. The exact parameters for the sterilization method are summarized in Table 6.

TABLE 6

| Phase | Parameter | Value |
|---|---|---|
| Leak Test | Vacuum Level | 500 mbar |
| Leak Test | Stabilization Time | 2 minutes |
| Leak Test | Leak Test Time | 5 minutes |
| Leak Test | Acceptable Total Leak | 13 mbar |
| Pre-conditioning | Pulse Quantity | 12 |
| Pre-conditioning | Vacuum Level | 500 mbar |
| Pre-conditioning | Vacuum Break Point | 700 mbar |
| Pre-conditioning | Jacket and Doors Temperature | 28° C. |
| Pre-conditioning | Vaporizer Temperature | 110° C. |
| Sterilization | Pulse Quantity | 3 |
| Sterilization | Vacuum Level | 500 mbar |
| Sterilization | $H_2O_2$ (59 wt. % solution) Injection Amount | 150 g/pulse |
| Sterilization | Injection Cycle Duration | 4500 milliseconds |
| Sterilization | Post-Injection Hold Time | 2 minutes |
| Sterilization | Transition Pressure Point | 940 mbar |
| Sterilization | Post-transition Hold Time | 7 minutes |
| First Aeration | Pulse Quantity | 10 |
| First Aeration | Vacuum Level | 500 mbar |
| First Aeration | Vacuum Break Point | 899 mbar |

TABLE 6-continued

| Phase | Parameter | Value |
|---|---|---|
| First Aeration | Exhaust Time | 0 minutes |
| First Aeration | Recirculate During Vacuum | Yes |
| Second Aeration | Pulse Quantity | 12 |
| Second Aeration | Vacuum Level | 500 |
| Second Aeration | Vacuum Break Point | 900 |
| Second Aeration | Exhaust Time | 10 |
| Second Aeration | Recirculate During Vacuum | No |

Figure 9B:
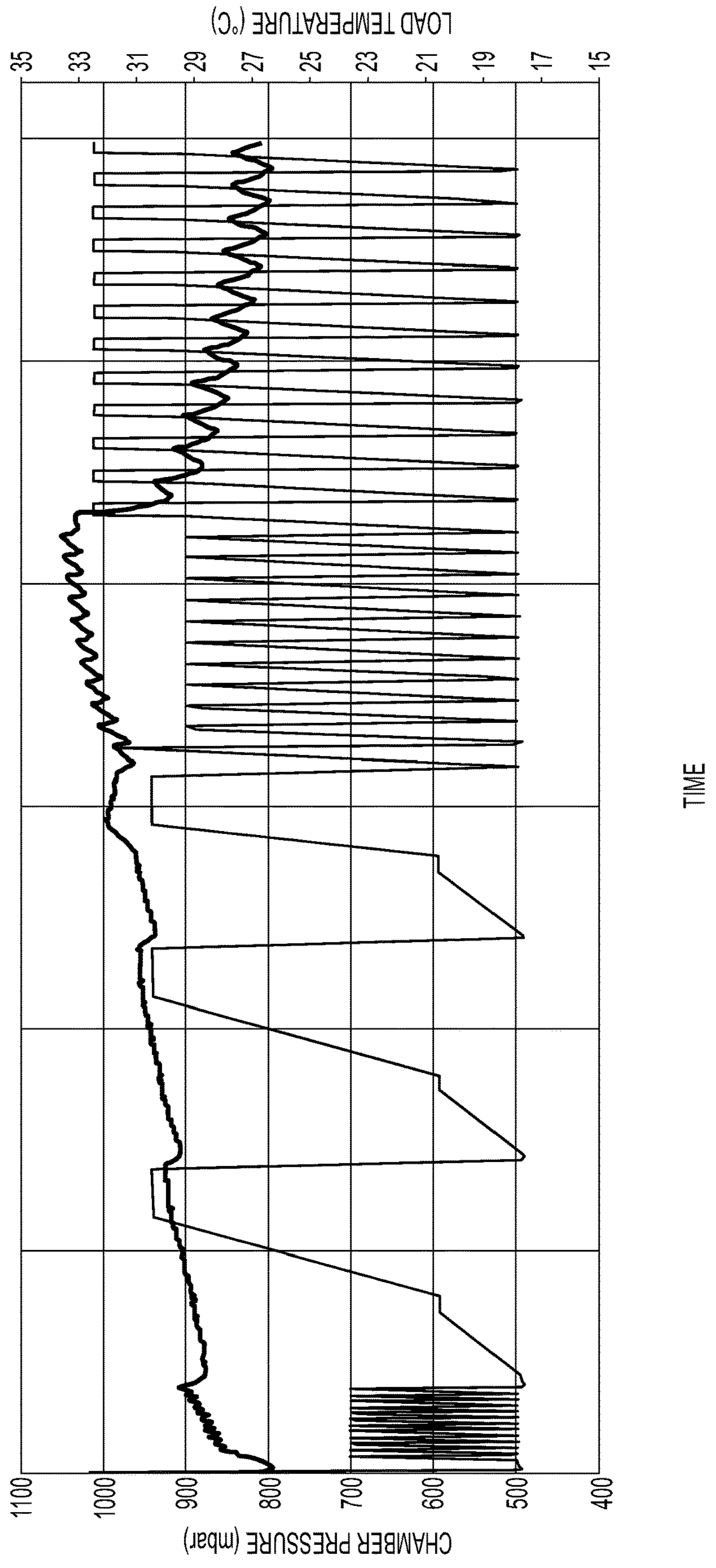

The pressure of the sterilization chamber and the temperature of the load, during the sterilization method of Example 6, were measured and are shown in FIG. 9B.

The efficacy and sterilizing efficiency of the sterilization protocols from Examples 1-6 were evaluated with chemical indicators, biological indicators, temperature loggers, humidity loggers, VHP monitors, and a handheld Drager VHP monitoring device. A summary of these results are shown in Table 7.

TABLE 7

| Sterilization Method | Sterilization Time (hours:minutes) | $H_2O_2$ Used (g of 57 wt. % solution) | Max. Load Temperature (° C.) | Total Time (hours:minutes) | Minimum Chamber Pressure (mbar) | BI Growth |
|---|---|---|---|---|---|---|
| Example 1 | 00:24 | 153.3 | 33.7 | 9:17 | 488 | 24/24 |
| Example 2 | 00:47 | 301.0 | 31.3 | 3:45 | 495 | 1/24 |
| Example 3 | 00:57 | 298.9 | 31.9 | 9:01 | 488 | 0/120 |
| Example 4 | 00:57 | 300.03 | 32.0 | 9:50 | 489 | 0/24 |
| Example 5 | 1:28 | 451.7 | 33.6 | 9:05 | 488 | N/A |
| Example 6 | 1:28 | 451.2 | 33.6 | 10:23 | 488 | 0/24 |

As shown in Table 7, sterilization methods including multiple sterilization pulses prevented biological indicators from growing. Although not shown in Table 7, each exemplary sterilization method also resulted in less than 1.0 part per million of residual VHP. Based on the data observed from the exemplary sterilization methods, it was determined that effective sterilization could be achieved with cycle temperatures less than 35° C., at a vacuum pressure greater than 480 mbar, with at least 300 g of 57 wt. % $H_2O_2$ solution, and a sterilization time of an hour. This is a more efficient sterilization protocol than previous methodologies, which required at least 500 g of 57 wt. % $H_2O_2$ solution, and a sterilization time of at least 2 hours and 15 minutes. The more efficient protocol means that more load (e.g., more pre-filled syringes containing medicament) per hour may be sterilized, as compared to methods known in the art.

The above description and examples are illustrative, and not intended to be restrictive. For example, and as has been described, the above-described embodiments (and/or aspects thereof) may be used in combination with each other.

What is claimed is:

1. A sterilization method comprising:

pre-conditioning a sterilization apparatus including a sterilization chamber comprising a sterilization load, wherein pre-conditioning the sterilization apparatus includes increasing a temperature of a portion of the sterilization apparatus to a temperature greater than a maximum temperature of the sterilization load, wherein the portion of the sterilization apparatus includes an inlet and a conduit connecting a vaporized hydrogen peroxide (VHP) injector to the inlet;

executing a sterilization phase, wherein the sterilization phase includes a plurality of sterilization pulses, wherein each sterilization pulse includes introducing vaporized hydrogen peroxide into the sterilization chamber via the inlet, and a temperature of the sterilization chamber is less than or equal to the maximum temperature of the sterilization load throughout the sterilization phase; and executing an aeration phase, wherein the aeration phase includes a plurality of aeration pulses, wherein the plurality of aeration pulses includes:

a primary aeration pulse comprising:

achieving a first vacuum pressure within the sterilization chamber, wherein the first vacuum pressure is 500 to 800 millibar; and after a first vacuum hold, increasing the pressure of the sterilization chamber to a pressure greater than 700 millibar; and a secondary aeration pulse comprising:

achieving a second vacuum pressure within the sterilization chamber, wherein the second vacuum pressure is less than 650 millibar; and after a second vacuum hold, adding air to the sterilization chamber while exhausting the sterilization apparatus.

2. The sterilization method of claim 1, wherein the plurality of aeration pulses includes a first primary aeration pulse, followed by a first secondary aeration pulse, followed by a second primary aeration pulse, followed by a second secondary aeration pulse.

3. The sterilization method of claim 1, wherein the sterilization load includes a semi-permeable envelope.

4. The sterilization method of claim 1, wherein each sterilization pulse comprises:

achieving a sterilization pressure within the sterilization chamber; and when the sterilization chamber is at the sterilization pressure, adding vaporized hydrogen peroxide to the sterilization chamber.

5. The sterilization method of claim 4, wherein the sterilization pressure is less than or equal to 650 millibars.

6. The sterilization method of claim 1, further comprising:

after the sterilization phase and prior to the aeration phase, adding a dry air to the sterilization chamber.

7. The sterilization method of claim 1, wherein the sterilization chamber includes a piston or diaphragm configured to adjust the pressure of the sterilization chamber, and the method further comprises:

after the sterilization phase, creating a low frequency pressure wave with the piston or diaphragm.

8. The sterilization method of claim 7, wherein the low frequency pressure wave moves liquid hydrogen peroxide in contact with the sterilization load.

9. A sterilization method comprising:

pre-conditioning a sterilization apparatus including a sterilization chamber comprising a sterilization load, wherein pre-conditioning the sterilization apparatus includes increasing a temperature of a portion of the sterilization apparatus to a temperature greater than a maximum temperature of the sterilization load, wherein the portion of the sterilization apparatus includes an inlet and a conduit connecting a vaporized hydrogen peroxide (VHP) injector to the inlet; and executing a sterilization phase, wherein a temperature of the sterilization chamber is less than or equal to the maximum temperature of the sterilization load throughout the sterilization phase, the sterilization phase includes first, second, and third sterilization pulses, and wherein each sterilization pulse includes:

achieving a sterilization pressure within the sterilization chamber; and when the sterilization chamber is at the sterilization pressure, adding an amount of vaporized hydrogen peroxide to the sterilization chamber via the inlet; and executing an aeration phase comprising:

achieving a vacuum pressure within the sterilization chamber, wherein the vacuum pressure is less than 650 millibar; and after a vacuum hold, adding air to the sterilization chamber while exhausting the sterilization apparatus;

wherein the amount of vaporized hydrogen peroxide added to the sterilization chamber during the first sterilization pulse is sufficient to establish a lethal concentration of hydrogen peroxide in the chamber;

the amount of vaporized hydrogen peroxide added to the sterilization chamber during the second sterilization pulse is less than the amount of vaporized hydrogen peroxide added to the sterilization chamber during the first sterilization pulse; and the amount of vaporized hydrogen peroxide added to the sterilization chamber during the second sterilization pulse is less than the amount of vaporized hydrogen peroxide added to the sterilization chamber during the third sterilization pulse.

10. The method of claim 9, wherein the first sterilization pulse is repeated at least once before the second sterilization pulse.

11. The method of claim 9, wherein the third sterilization pulse is repeated at least twice.

12. The method of claim 9, wherein the amount of vaporized hydrogen peroxide added to the sterilization chamber during the first sterilization pulse includes at least 0.1 moles of hydrogen peroxide per cubic meter of volume of the sterilization chamber.

13. The method of claim 9, wherein each sterilization pulse further includes:

(i) adding gas into the sterilization chamber to increase the pressure to a hold pressure, wherein the hold pressure is greater than 700 millibar; and (ii) decreasing the pressure of the sterilization chamber to the sterilization pressure.

14. The method of claim 13, wherein step (i) takes more time than step (ii).

15. The method of claim 14, wherein each sterilization pulse further comprises:

before step (i), maintaining the pressure of the sterilization chamber for a first hold time;

after step (ii), maintaining the pressure of the sterilization chamber for a second hold time;

wherein the second hold time is longer than the first hold time.

16. The method of claim 9, wherein the sterilization chamber includes a distribution manifold, an inlet, and a chamber wall, and the method further comprises:

during the first, second, and third sterilization pulses, maintaining a temperature of the chamber wall to be approximately the same as a temperature of the inlet or a temperature of the distribution manifold.

17. A sterilization method comprising:

pre-conditioning a sterilization apparatus including a sterilization chamber comprising a sterilization load, wherein pre-conditioning the sterilization apparatus includes increasing a temperature of a portion of the sterilization apparatus to a temperature greater than a maximum temperature of the sterilization load, wherein the portion of the sterilization apparatus includes an inlet and a conduit connecting a vaporized hydrogen peroxide (VHP) injector to the inlet; and a first sterilization pulse including adding a first amount of vaporized hydrogen peroxide to the sterilization chamber via the inlet, wherein the first amount is sufficient to establish a lethal concentration of hydrogen peroxide in the sterilization chamber;

a plurality of second sterilization pulses, wherein each second sterilization pulse includes adding a second amount of vaporized hydrogen peroxide to the sterilization chamber via the inlet, wherein the second amount is less than the first amount; and a plurality of third sterilization pulses, wherein each third sterilization pulse includes adding a third amount of vaporized hydrogen peroxide to the sterilization chamber via the inlet, wherein the third amount is less than the second amount;

wherein, throughout the sterilization method, a temperature of the sterilization chamber is less than or equal to the maximum temperature of the sterilization load throughout the sterilization phase.

18. The method of claim 17, wherein the sterilization chamber comprises a load, and the load includes a semi-permeable material defining an interior of the load and an exterior of the load; and wherein after the plurality of third sterilization pulses, a concentration of hydrogen peroxide in the interior of the load is approximately equal to a concentration of hydrogen peroxide in the exterior of the load.

19. The method of claim 17, further comprising executing an aeration pulse including:

(i) lowering the pressure of the sterilization chamber to a first aeration pressure, wherein the first aeration pressure is less than 650 millibar; and (ii) increasing the pressure of the sterilization chamber to a second aeration pressure, wherein the second aeration pressure is greater than 700 millibar;

wherein a rate of pressure change in step (ii) is at least 100 millibar per minute faster than a rate of pressure change in step (i).

20. The method of claim 19, further comprising, prior to the aeration phase, removing moisture from the sterilization chamber by passing the contents of the sterilization chamber through a condenser.

21. A method for sterilizing a syringe, the method comprising:

placing the syringe inside a sterilization chamber; and subjecting the syringe to the sterilization method of claim 1.

22. The method of claim 1, wherein pre-conditioning the sterilization apparatus includes increasing the temperature of the portion of the sterilization apparatus to at least 110° C.

23. A method for sterilizing a syringe, the method comprising:

placing the syringe inside a sterilization chamber; and subjecting the syringe to the sterilization method of claim 17.

* * * * *